US011766394B2

(12) United States Patent
Herrlein et al.

(10) Patent No.: US 11,766,394 B2
(45) Date of Patent: Sep. 26, 2023

(54) MULTICOMPONENT COMPOSITION (MICHAEL ADDITION)

(71) Applicant: HFC Prestige International Holding Switzerland S.a.r.l, Petit-Lancy (CH)

(72) Inventors: Mathias Kurt Herrlein, Kronberg (DE); Matija Crne, Wiesbaden (DE); Corinne Mohr, Lorsch (DE); Graham Neil McKelvey, Schwalbach (DE); Simon Paul Godfrey, Oberursel (DE); Axel Meyer, Frankfurt am Main (DE); Petra Braun, Hessen (DE); Malte Afflerbach, Darmstadt (DE); Andrej Gross, Schwalbach am Taunus (DE); Michael A. Brook, Ancaster (CA); Yan Wang, Parsippany, NJ (US)

(73) Assignee: Wella International Operations Switzerland Sarl, Petit-Laney (CH)

( * ) Notice: Subject to any disclaimer, the term of this patent is extended or adjusted under 35 U.S.C. 154(b) by 325 days.

(21) Appl. No.: 15/733,805

(22) PCT Filed: Jul. 5, 2019

(86) PCT No.: PCT/EP2019/068186
§ 371 (c)(1),
(2) Date: Nov. 30, 2020

(87) PCT Pub. No.: WO2020/008073
PCT Pub. Date: Jan. 9, 2020

(65) Prior Publication Data
US 2022/0117877 A1 Apr. 21, 2022

Related U.S. Application Data

(60) Provisional application No. 62/769,239, filed on Nov. 19, 2018, provisional application No. 62/740,027, filed on Oct. 2, 2018, provisional application No. 62/739,592, filed on Oct. 1, 2018, provisional application No. 62/739,672, filed on Oct. 1, 2018.

(30) Foreign Application Priority Data

Mar. 27, 2019 (WO) ................ PCT/EP2019/057813
Mar. 27, 2019 (WO) ................ PCT/EP2019/057814

(51) Int. Cl.
| A61Q 5/12 | (2006.01) |
| A61K 8/895 | (2006.01) |
| A61K 8/36 | (2006.01) |
| A61K 8/41 | (2006.01) |
| A61K 8/58 | (2006.01) |
| A61K 8/73 | (2006.01) |
| A61K 8/86 | (2006.01) |
| A61K 8/898 | (2006.01) |
| A61Q 5/06 | (2006.01) |

(52) U.S. Cl.
CPC ................ *A61K 8/895* (2013.01); *A61K 8/36* (2013.01); *A61K 8/41* (2013.01); *A61K 8/585* (2013.01); *A61K 8/73* (2013.01); *A61K 8/86* (2013.01); *A61K 8/898* (2013.01); *A61Q 5/065* (2013.01); *A61Q 5/12* (2013.01); *A61K 2800/412* (2013.01); *A61K 2800/43* (2013.01); *A61K 2800/594* (2013.01); *A61K 2800/882* (2013.01); *A61K 2800/884* (2013.01); *A61K 2800/95* (2013.01)

(58) Field of Classification Search
None
See application file for complete search history.

(56) References Cited

U.S. PATENT DOCUMENTS

| 4,559,057 A | 12/1985 | Bogaty et al. |
| 5,258,481 A | 11/1993 | Hesselmans et al. |
| 5,567,428 A | 10/1996 | Hugehes |
| 5,990,479 A | 11/1999 | Weiss et al. |
| 6,225,198 B1 | 5/2001 | Alivisatos et al. |
| 6,451,747 B1 | 9/2002 | Decoster |
| 6,492,484 B2 | 12/2002 | Misumi et al. |

(Continued)

FOREIGN PATENT DOCUMENTS

| CN | 111432887 A | 7/2020 |
| CN | 111432888 A | 7/2020 |

(Continued)

OTHER PUBLICATIONS

International Search Report issued in connection with PCT Application No. PCT/EP2019/057811 dated Sep. 4, 2019.
European Search Report received for EP Patent Application No. 17195273.2, Extended European Search Report dated Jan. 11, 2018.
International Search Report and written opinion received in PCT Patent Application No. PCT/EP2021/057812, dated Jan. 7, 2019.
Campiglio Chiara Emma et al., "Coss-Linking Strategies for Electrospun Gelatin Scaffolds", Materials, vol. 1, No. 15, Aug. 4, 2019.
International Search Report and written opinion received in PCT Patent Application No. PCT/EP2021/067924, dated Nov. 26, 2021.

(Continued)

*Primary Examiner* — Jyothsna A Venkat
(74) *Attorney, Agent, or Firm* — Dennemeyer & Associates LLC; Victoria Friedman

(57) ABSTRACT

The instant disclosure generally relates to a multicomponent composition for coating mammalian or synthetic keratin material and textiles, the composition comprising a first and second components and a third component. The first and second components comprise first and second compounds respectively. Any one or more of the first, second and third components may also comprise pigment microparticles. The first, second and third compounds meld together on keratin material and textiles and especially on hair to form a coating that can be formulated to provide temporary coverage or provide permanent coverage. The multicomponent composition formed and set in situ as a solid linked coating ranges from ready removability to substantially permanent lastingness.

10 Claims, 18 Drawing Sheets

(56) References Cited

U.S. PATENT DOCUMENTS

| | | |
|---|---|---|
| 9,546,301 B2 | 1/2017 | Derksen et al. |
| 10,011,677 B2 | 7/2018 | Yamashita et al. |
| 10,959,919 B2 | 3/2021 | Dahne et al. |
| 10,973,754 B2 | 4/2021 | Herrlein et al. |
| 11,324,688 B2 | 5/2022 | Herrlein et al. |
| 11,478,415 B2 | 10/2022 | Herrlein et al. |
| 2003/0203978 A1 | 10/2003 | Obrien et al. |
| 2004/0010863 A1 | 1/2004 | Gawtrey et al. |
| 2005/0226838 A1 | 10/2005 | Krause et al. |
| 2006/0041026 A1 | 2/2006 | Mahr et al. |
| 2007/0134180 A1 | 6/2007 | Simard et al. |
| 2008/0108740 A1 | 5/2008 | Evers |
| 2008/0184496 A1 | 8/2008 | Brun et al. |
| 2009/0233062 A1 | 9/2009 | Nakamura et al. |
| 2010/0083446 A1 | 4/2010 | Brun et al. |
| 2010/0088036 A1 | 4/2010 | Goddard-Clark et al. |
| 2011/0061179 A1 | 3/2011 | Cremer et al. |
| 2011/0083284 A1 | 4/2011 | Suddaby et al. |
| 2014/0242281 A1 | 8/2014 | Swarup et al. |
| 2014/0336093 A1 | 11/2014 | Koellnberger |
| 2015/0174051 A1 | 6/2015 | Teboul |
| 2016/0120284 A1 | 5/2016 | Crne et al. |
| 2016/0120285 A1 | 5/2016 | Crne et al. |
| 2016/0175212 A1 | 6/2016 | Zhou et al. |
| 2016/0235655 A1 | 8/2016 | Herrlein et al. |
| 2016/0271049 A1 | 9/2016 | Schulze et al. |
| 2017/0001045 A1 | 1/2017 | Aubert et al. |
| 2017/0158888 A1 | 6/2017 | Kang et al. |
| 2017/0189312 A1 | 7/2017 | Van Nguyen et al. |
| 2017/0189314 A1 | 7/2017 | Elsen-wahrer et al. |
| 2018/0105718 A1 | 4/2018 | Swarup et al. |
| 2018/0263353 A1 | 9/2018 | Crne et al. |
| 2018/0263354 A1 | 9/2018 | Crne et al. |
| 2021/0220251 A1 | 7/2021 | Speckbacher et al. |
| 2021/0401713 A1 | 12/2021 | Herrlein et al. |
| 2022/0054392 A1 | 2/2022 | Herrlein et al. |

FOREIGN PATENT DOCUMENTS

| | | |
|---|---|---|
| DE | 19913625 A1 | 9/2000 |
| DE | 102006011271 A1 | 9/2007 |
| EP | 132960 A2 | 2/1985 |
| EP | 1184426 A2 | 3/2002 |
| EP | 1600148 A1 | 11/2005 |
| EP | 1600149 A1 | 11/2005 |
| EP | 1825883 A1 | 8/2007 |
| EP | 3015134 A1 | 5/2016 |
| EP | 3015135 A1 | 5/2016 |
| EP | 3058934 A1 | 8/2016 |
| EP | 3058989 A1 | 8/2016 |
| EP | 3397346 A1 | 11/2018 |
| FR | 2899795 A1 | 10/2007 |
| FR | 2992559 A1 | 1/2014 |
| JP | S 50-034400 A | 4/1975 |
| JP | S 60-105608 A | 6/1985 |
| JP | 2005-350460 A | 12/2005 |
| JP | 2007-084510 A | 4/2007 |
| JP | 2008-502613 A | 1/2008 |
| JP | 2009-520002 A | 5/2009 |
| JP | 2010-530842 A | 9/2010 |
| JP | 2012-515219 A | 7/2012 |
| JP | 2012-530841 A | 12/2012 |
| JP | 2015-521646 A | 7/2015 |
| JP | 2017-533224 A | 11/2017 |
| KR | 20190028636 A | 3/2019 |
| WO | 2005065632 A1 | 7/2005 |
| WO | WO-2007071706 A2 | 6/2007 |
| WO | WO-2009073759 A1 | 6/2009 |
| WO | WO-2011128255 A1 | 10/2011 |
| WO | WO-2015097308 A1 | 7/2015 |
| WO | WO-2016066747 A1 | 5/2016 |
| WO | WO-2017108599 A1 | 6/2017 |
| WO | WO-2017117543 A1 | 7/2017 |
| WO | 2017189585 A1 | 11/2017 |
| WO | WO-2017220781 A1 | 12/2017 |
| WO | WO-2018039314 A1 | 3/2018 |
| WO | WO-2018130912 A1 | 7/2018 |
| WO | WO-2018185345 A1 | 10/2018 |
| WO | 2018234530 A1 | 12/2018 |
| WO | 2019071204 A1 | 4/2019 |
| WO | 2019071207 A1 | 4/2019 |
| WO | WO-2019211050 A1 | 11/2019 |
| WO | WO-2020007511 A1 | 1/2020 |
| WO | WO-2020008073 A2 | 1/2020 |
| WO | WO-2020008074 A1 | 1/2020 |
| WO | 2020035362 A1 | 2/2020 |
| WO | WO-2020008073 A3 | 3/2020 |
| WO | WO-2020114647 A1 | 6/2020 |
| WO | 2021032837 A1 | 2/2021 |
| WO | 2021032873 A1 | 2/2021 |

OTHER PUBLICATIONS

International Search Report and written opinion received in PCT Patent Application No. PCT/EP2021/067925, dated Nov. 22, 2021.
International Search Report and written opinion received in PCT Patent Application No. PCT/EP2021/067928, dated Dec. 22, 2021.
International Search Report and Written Opinion received for PCT Patent Application No. PCT/US2018/054717, dated Dec. 20, 2018.
International Search Report and Written Opinion received for PCT Patent Application No. PCT/US2018/054724, dated Feb. 26, 2019.
International Search Report and Written Opinion received for PCT Patent Application No. PCT/US2019/057812, dated Jan. 7, 2019.
International Search Report and Written Opinion received for PCT Patent Application No. PCT/EP2019/057811, dated Sep. 4, 2019.
International Search Report and written opinion received in PCT Patent Application No. PCT/EP2021/067927, dated Dec. 6, 2021.
International Search Report and written opinion received in PCT Patent Application No. PCT/EP2021/067926, dated Dec. 7, 2021.
Cansu et al, "Atmospheric Pressure Plasma Jet Treatment of Human Hair Fibers", Journal of Bio- and Tribo-Corrosion, vol. 1:7, No. 1, Feb. 4, 2015.
Zheng et al, "Adhesion of aqueous polyurethane adhesive to human hair", International Journal of Adhesion and Adhesives, Elsevier, Amsterdam, NL, vol. 48, Sep. 30, 2013, pp. 14-19.
Shima et al, "The effect of nitrogen plasma on the skin and hair follicles : a possible promising future for the treatment of alopecia", Archives of Dermatological Research, Springer Berlin Heidelberg, Berlin/Heidelberg, vol. 312, No. 5, Dec. 6, 2019 , pp. 361-371.
Shao et al.: "Surface Treatment of Wool to Achieve Hydrophilic Fibre and the Effect on Subsequent Dyeing and Protease Treatment", Advanced Materials Research; ISSN 1662-8985; Eco-Dyeing, Finishing and Green Chemistry : Selected, Peer Reviewed Papers From the 2011 International Conference on Eco-Dyeing, Finishing and Green Chemistry (EDFGC 2011), Jun. 8-12, 2011, Hangzhou, China, vol. 441, Jan. 1, 2012 (Jan. 1, 2012), pp. 249-254.
"U.S. Appl. No. 17/052,431, Preliminary Amendment filed Nov. 2, 2020".
"International Application Serial No. PCT/EP2019/057813, International Search Report dated Jul. 11, 2019", 5 pgs.
"International Application Serial No. PCT/EP2019/057813, Written Opinion dated Jul. 11, 2019", 9 pgs.
"International Application Serial No. PCT/EP2019/057814, International Preliminary Report on Patentability dated Nov. 12, 2020", 19 pgs.
"International Application Serial No. PCT/EP2019/057814, International Search Report dated Sep. 16, 2019", 8 pgs.
"International Application Serial No. PCT/EP2019/057814, Invitation to Pay Additional Fees dated Jul. 26, 2019", 10 pgs.
"International Application Serial No. PCT/EP2019/057814, Written Opinion dated Sep. 16, 2019", 17 pgs.
"International Application Serial No. PCT/EP2019/068186, International Search Report dated Feb. 3, 2020", 7 pgs.
"International Application Serial No. PCT/EP2019/068186, Invitation to Pay Additional Fees dated Dec. 2, 2019", 14 pgs.
"International Application Serial No. PCT/EP2019/068186, Written Opinion dated Feb. 3, 2020", 12 pgs.

(56) References Cited

OTHER PUBLICATIONS

"International Application Serial No. PCT/EP2019/068187, International Search Report dated Dec. 4, 2019", 5 pgs.
"International Application Serial No. PCT/EP2019/068187, Written Opinion dated Dec. 4, 2019", 12 pgs.
"International Application Serial No. PCT/EP2019/076647, International Search Report dated Jan. 9, 2020", 7 pgs.
"International Application Serial No. PCT/EP2019/076647, Written Opinion dated Jan. 9, 2020", 13 pgs.
Bordes, C, et al., "Determination of poly(epsilon-caprolactone) solubility parameters: Application to solvent substitution in a microencapsulation process", International journal of pharmaceutics, 383(1-2), (Jan. 4, 2010), 236-243.

MULTICOMPONENT COMPOSITION (MICHAEL ADDITION)

CROSS-REFERENCE TO RELATED APPLICATION

This patent application is a U.S. National Stage Filing under 35 U.S.C. 371 from International Application No. PCT/EP2019/068186, filed on Jul. 5, 2019, and published as WO 2020/008073 on Jan. 9, 2020, which application claims the benefit of priority to U.S. Application Ser. No. 62/694,808, filed Jul. 6, 2018, U.S. Application Ser. No. 62/739,592, filed Oct. 1, 2018, U.S. Application Ser. No. 62/739,672, filed Oct. 1, 2018, U.S. Application Ser. No. 62/740,027, filed Oct. 2, 2018, U.S. Application Ser. No. 62/769,239, filed Nov. 19, 2018, PCT Application Serial No. PCT/EP2019/057814, filed Mar. 27, 2019, and PCT Application Serial No. PCT/EP2019/057813, all of which are incorporated by reference herein in their entirety.

BACKGROUND

Treatments to mammalian or synthetic keratin material are known. Mammalian keratin material (natural hair) is structured as a cuticle or outer surface layer, a cortex which is an internal layer containing melanin or coating bodies and keratin bundles, and sometimes a central core termed the medulla. Typical dye treatments focus on changes of the cortex. Typical hair styling and conditioning treatments focus on structure and lubricity but cannot accomplish both at the same time. Another treatment focuses on addition of pigments to the surfaces of hair strands. Typical treatment for surface coating attaches pigment particles with glue-like material. Of particular note, for all of these treatments is their ability to after the appearance of the hair, for example by changing the coating or reflective properties of hair or by changing the tactile properties of hair and skin or by changing the dimensional and/or adherent properties of the hair, skin, eyelashes and/or treatment itself.

For dye treatments the alteration of appearance can be achieved through treating hair with a formulation containing dye molecules (so call direct dyes) which diffuse into or are absorbed on and sometimes through the cuticles of the hair fibers. Alternatively, so called oxidative dyes may be employed wherein the dye precursors diffuse into the hair and then react to form coating species within the hair including within the cortex of the hair. Often the oxidative dye products are designed to also lighten the hair, decolorizing some of the melanin within the cortex to enable a wider range of coatings to be achieved. Over time the coating imparted to the hair is removed during washing. This can happen rapidly for so called direct dyes and leads to a shod term change in hair appearance, typically lasting for a few washes. The so called oxidative dyes may last considerably longer, and indeed removing the coating can be hard to achieve, even after a considerable number of washes. When oxidative dyes are eventually removed by washing out, the melanin has also been decolorized by bleaching so that it will not return to its original coating but to a lighter coating. Unfortunately, the process of decolorizing hair leads not only to a lightening of the hair but also to a change in the perceived tone of the hair, leading to what is often described as an off tone or brassy result where the hair looks more orange than untreated hair of a similar lightness.

One disadvantage of the known oxidative dye technologies in this area is that the methods involve applying coating compositions for an extended period of time to enable the coating to develop within the hair. These compositions in some cases may also lead to some temporary scalp irritation. Together, the extended waiting time and potential irritation, prevents the hair coating process for some users from being a pleasant or a so-called wellness experience. Such coating compositions may also alter the hair structure itself, leading to oxidation of the hair surface, and partial degradation of the keratinous proteins from which the hair structure is constructed. With repeated coatings, these changes in hair structure become more pronounced and can be felt as poor hair condition. The coating obtained when coatings with such a composition is also hard to predict, and even highly experienced users can still be surprised with the actual results that are obtained for a given product. Yet another drawback known to such coating technologies is that, once the coating is on and within the hair, the dye based coating material is difficult to remove and/or cannot be completely removed. Another drawback for the dye based approach is that the application of hair coating materials can yield uneven results as adherence to the surface and/or penetration of hair coating materials into the hair can vary with hair type for example for a consumer differing coating results may be visible between hair roots and hair tips. This can lead to an unnatural looking result. Some desired differences may still be visible due to the non-uniformity in coating of the underlying hair, for example subtle difference in strand to strand levels of pheomelanin and eumelanin in a consumer may yield slightly different coating results, even when the same coating pigments or dyes are applied to a consumer. While some strand to strand variation is needed to provide natural looking hair, too much or too little can again lead to an unnatural looking coating result. Due to the number of factors that determine the final hair coating result for example, the length of application time, the underlying hair coating, the hair changes from root to tip, it's hard for even experienced users to accurately predict the final coating result and look. There is therefore a need for compositions and methods that not only make the multicomponent experience a beauty/wellness experience, but also address, among other things, the foregoing drawbacks of known technologies.

Disadvantages of typical conditioning and styling treatments involve sticky, adherent coatings that tend toward moisture absorption (deliquescence) increasing weight on the hair. These treatments also change the tactile properties of keratin material such as hair and skin to make them feel slick, rough, stiff, and generally unappealing. These treatments also are not long lasting and can be removed by combing or wet brushing as well as simple washing. While it is desirable in many circumstances to be able to easily remove such coatings on keratin materials, such as removal of make-up from skin, in other circumstances it is not, such as a hair style. Moreover, with readily removed treatments, spurious removal, such as by rain, can occur. The result is unsightly.

As mentioned at the outset, alternative multicomponent techniques have also been investigated. One such approach has involved coating hair strands with coating pigment particles. This approach has proved difficult at best as it is fraught with particle agglomeration and clumping, stickiness, matted hair strands and ready removal by washing. The attachment techniques often leave clumps of particles on the hair strands and the glue-like material used for attachment is often sticky and can glue strands together. Moreover, the pigment particles typically do not distribute appropriately, leave an artificial appearance and are not user friendly. The coating effect is also typically very short lived and is removed within a couple of hair washes.

It is therefore an object to develop a multicomponent composition and technique that do not result in harm to hair protein, are user friendly, provide appropriate coating and luster, and leave the hair manageable, free flowing and capable of moving naturally. Additional objects include development of a multicomponent composition and technique that may be manipulated to provide an easily removable coating, a semi-permanent coating or a very long lasting to essentially permanent coating.

SUMMARY

These and other objects are accomplished by aspects of the composition and method of use of the present invention. According to aspects of the invention, the multicomponent composition, method and coated substrate material embodiments such as keratin material, for example hair of any sort, nails, skin, hair extensions and other substrate material including but not limited to textiles and paper provide a surface coating of substrate material, textiles and paper (hereinafter substrate material). Preferred in regard to substrate material is the subcategory keratin material, especially hair of all kinds including scalp, eyelash and eyebrow hair, nails and most especially preferred is scalp hair. For hair of all kinds, the coating that may be substantially uniform to significantly varied, may give hair strands an appearance of lower or higher chroma, shiny or reflective nature. These aspects provide coating fastness during a series of washes with shampoo or soap yet with appropriate formulations can be readily removed to leave the natural shade of the hair. The coating fastness may be tailored to be temporary to more permanent in longevity. These aspects significantly lessen and/or avoid treatment of hair that may cause breakage of keratin protein intermolecular bonds.

An aspect of the invention concerning the multicomponent composition provides embodiments comprising first and second components, each comprising a functional compound. The first component comprises a linear, branched, cyclic, cage, dendritic, star or fullerene-like first compound with two or more of one half of a pair of in situ functional groups. The second component also comprises a second linear, branched, cyclic, cage, dendritic, star or fullerene-like compound with the other half of a pair of in situ functional groups. Generally, other than the pair of in situ functional groups, the first and second compounds may comprise the same linear, branched, dendritic, cyclic, star or fullerene-like organic compound or the same linear, branched, cyclic, cage or dendritic silicone compound or different linear, branched, cyclic, cage, dendritic, star or fullerene-like organic compound or linear, branched, cage, cyclic or dendritic silicone compounds. The first and second compounds may also be grafted or block copolymers of organic and silicone segments. Preferred configurations of the first and second compounds are the linear and branched arrangements of the backbones, chains and frames of the small molecules, monomer group, oligomer and polymer. Especially preferred configurations of the first and second compounds are the linear arrangements. The organic and silicone compounds may be small molecules such as saturated organic groups or siloxane groups, aromatic organic groups, monomeric groups, oligomers or polymers. The first organic or silicone compound carries as a functional group an $\alpha$, $\beta$ unsaturated carboxyl group such as for example olefinoyloxy group. The first compound carries at least 2 functional groups which may be attached through optional connecting units to the organic or silicone chain, backbone, side chain or small molecule frame. The second organic or silicone compound carries as a functional group an amine and/or a nitrogen with the amine being a pendant amine group and the nitrogen being a nitrogen as part of the frame, chain, backbone and/or side chain. The second compound carries at least 2 functional groups which may be attached through optional linking groups to the organic or silicone chain, backbone, side chain or small molecule frame and/or may be contained within the frame, chain, backbone and/or side chain.

Embodiments of the multicomponent composition also provide a third component comprising a base compound. The base compound comprises a small molecule, a dimer, trimer, oligomer or polymer of organic or silicone construction which carries one or more pendant and/or terminal third functional groups which are amine groups preferably, the base compound is an oligomer or polymer with pendant amine groups and backbone or chain nitrogen groups. More preferably, the base compound is a polyolefinic imine produced from a C2 to C20 aziridine, such as polyethylene imine, polypropylene imine or polyoctylene imine. The third functional groups of the base compound interact with the first and second functional groups as well as other moieties of the first and second compounds through covalent, ionic, entanglement, dipolar, electronic and/or electrostatic linking or any combination thereof to meld together the first compound, the second compound and the base compound. The third component is typically and usually adapted to be combined with the keratin material as a pretreatment prior to sequential, simultaneous or mixed application of the first and second components.

Embodiments of the multicomponent composition also optionally provide a fourth component comprising an agent, such as a catalyst, an accelerator, a curing agent, an enhancer, a reaction retarder and/or an inorganic complexer, for efficiently and preferably gently facilitating the melding together of the first, second and third components.

One or both or all of the first, second and third components may also further comprise pigment particles (also synonymously described herein as pigment microparticles) and both typically comprise a medium. The pigment particles may comprise irregular shapes of at least one pigment coating and have at least one dimension of less than one micron.

It has been discovered that the interactive character of the first and second components applied to the keratin material and to the broader substrate material delivers good remanence and desirable qualities to the keratin material such as hair coated with the composition, and optionally as well as preferably, hair coated with the composition containing pigment particles. It has further been discovered that pretreatment with the third component designed to interact with the first and second components unexpectedly delivers significantly increased remanence. Although the unexpected significant remanence as well as other desirable qualities are achieved irrespective of the specific nature of the compounds, these properties are especially surprising when covalent and hydrogen bonding properties among the compounds and the third component are incorporated. The in situ linkable combination of the pretreatment base compound with the two compounds achieves unexpected, remarkable remanence.

Embodiments of the first and second compounds include reactive n, p unsaturated carboxyl units and amine/nitrogen units that may be paired together to enable in situ linking of the first and second compounds. The third compound (base compound) interacts as described above with the first and second compounds to enhance the adhesion to the substrate. The functional groups of these compounds are complementarily reactive and are arranged with the compounds so as to provide an in situ combination and form cross linked compounds, preferably having a net or star like configuration.

The combination of first, second and third compounds may be utilized as a coating on keratin material such as on hair, nails, eyebrows, eyelashes, skin and substrate material extending to organic or synthetic textiles. Examples include hairstyling, clear nail coating and/or protection, textile coating for protection, strength and durability. Preferably, the utilization as a coating is directed to keratin material such as hair, nails, eyebrows and eyelashes. More preferably utilization as a coating is directed to hair of the scalp.

Each of the first, second and third compounds or any combination thereof may also be combined with pigment microparticles to provide a colored coating on keratin material or textiles. Embodiments of the pigment microparticles used on the multicomponent composition described herein may comprise organic pigment microparticles, which imparts coating to the hair, having a given D50[vol], and pigment microparticles, for providing light scattering properties to the coated hair, having a D50[vol] which is larger than the D50[vol] value of the organic pigment microparticles. Embodiments may also include microparticle metal flakes and/or transition metal oxides (such as Zr, Tu, Ti) such as titanium dioxide for light reflection to add shine to the desired coating or to make the hair appear to be lighter than the starting hair coating.

Embodiments of the method for applying the multicomponent composition to substrate material, preferably keratin material, focus on the reactive features of the first, second and third functional groups. Embodiments of the method utilize first the first and second components. The first and second components of the multicomponent composition may be mixed together before application to the substrate material, preferably keratin material, may be applied separately and simultaneously to the substrate material, preferably keratin material, or may be applied sequentially to the substrate material, preferably keratin material. Upon the combination of the first and second components, the first and second compounds interact through their complementary functional groups by covalent, ionic, entanglement, dipolar, electronic and/or electrostatic linking to form a wash resistant coating with optional pigment microparticles on the substrate material, preferably keratin material. Prior to sequential, simultaneous or mixed application of the first and second components to the substrate material, preferably keratin material, the third component is applied as a pretreatment of the substrate material. A fourth component may be combined with the first and second components during their application to accelerate, decelerate, catalyze, cure, aid and/or otherwise promote or retard the in situ linking among the constituents of the first, second and third components as well as with the substrate material, preferably keratin material. For embodiments incorporating the first, second and third components, it is believed that the combination of first, second and third functional groups enables the covalent, ionic, entanglement, dipolar, electronic and/or electrostatic linking or any combination thereof among the first and second compounds, the base compound and the substrate material, preferably keratin material. These embodiments enable linkage of all substances together to make them resistant to removal by ordinary means. Indeed, this combination with the pretreatment melding the components together as a highly remanent coating on substrate material, preferably keratin material. The embedded pigment microparticles are distributed in and throughout the coating.

In addition to the first and second compounds, base compound, agent and optional pigment microparticles of the first, second, third and optional fourth components, the multicomponent composition may optionally contain additional ingredients helpful and beneficial to the substrate material and/or its coating. These additional ingredients include but are not limited to one or more of dispersants, surface treatment agents for the pigment microparticles, plasticizers, conditioners, suspending agents, thickening agents, adjuvants, moisturizers, surfactants, fatty substances, waxes, fatty amides and soluble organic dyes of coatings different from those of the pigment microparticles.

An aspect of the invention concerning the wash-fastness or remanence of the coating on the substrate material, preferably keratin material, and especially on hair strands, comprises the ability of the coating to resist dissolution by ordinary cleaning of the substrate material such as hair. Ordinary cleaning may involve washing with soap and water, washing with an aqueous dilution of shampoo and washing with water.

Another aspect of the invention comprises the ability to adjust the composition and technique for application to provide a temporary coating that is easily removable by a single shampoo or washing. Combined with the foregoing technique and composition for providing a highly remanent coating, the invention provides a complete keratin material coating technique ranging from a readily removable to a permanent coating of keratin fiber, preferably of hair.

The number and placement of the complementary functional groups, average molecular size of the first and second compounds, dilution with inert materials and optional inclusion of shampoo loving substituents within the first and second compounds is capable of producing a coating for keratin material that is facilely removable with simple shampooing. Because of the ability to vary the character of the coating from significantly remanent and permanent to facilely removable, the developments according to the invention enable a wide range of coating properties suitable for temporary and permanent purposes.

An aspect of the invention concerning removal of the coating on the substrate material, such as on hair strands, comprises application of a medium of a trigger formulation designed to remove the coating. The trigger formulation embodiments of the invention comprise media with strongly solvating surfactant, media with fluoride compounds, with fluoride salts, and/or media with base or acid and/or ionic media, and combinations of such media. Embodiments of the base include organic and inorganic compounds that provide a stronger basic medium than does a dilute aqueous mixture of soap or a shampoo containing an anionic surfactant. Embodiments of the acid include organic and inorganic compounds that provide a strong acidic medium. Additionally, mildly abrasive particles may also be added to the composition to help with the removal of the coating, for example silicas. Examples of removal compositions include those with monoethanolamine, sodium hydroxide, sodium fluoride, phosphate based anionic surfactants such as crodafos, and sulfate based surfactants such as lauryl sulfate. Additionally, basic gas producing materials such as sodium carbonate may be added to the removal composition to basify and to break up and lift coating fragments by carbon dioxide production.

An additional aspect of the invention concerns the application of the multicomponent composition to substrate material such as keratin material including brows, lashes, nails and skin as well as to hair on the scalp. Additionally, the multicomponent composition may be applied to animal hair or fur or synthetic materials. The multicomponent composition may be applied to these kinds of keratin materials with appropriate adjustments of the composition parameters within the parameters described for hair on the scalp. Typically, the eyebrow hair may be treated with the multicomponent composition using parameters similar to or the same as those of the multicomponent composition for hair on the scalp. The hair of eyelashes typically can be similarly treated with the multicomponent composition for eyebrows and the viscosity adjusted to provide a somewhat more viscous composition for application to the eye lashes. For nails and skin, the parameter, of the multicomponent composition may have a higher solids content and higher number of first, second and third functional groups for in in situ linking than the parameters for the hair and viscosity may be adjusted to provide embodiments that will not readily drip or otherwise flow off the nail or skin surface to which the multicomponent composition is applied. The multicomponent composition for nails and skin will preferably have higher in situ linking to provide a durable coating or covering on the keratin nail and skin substrate.

DEFINITIONS

Figure 1:
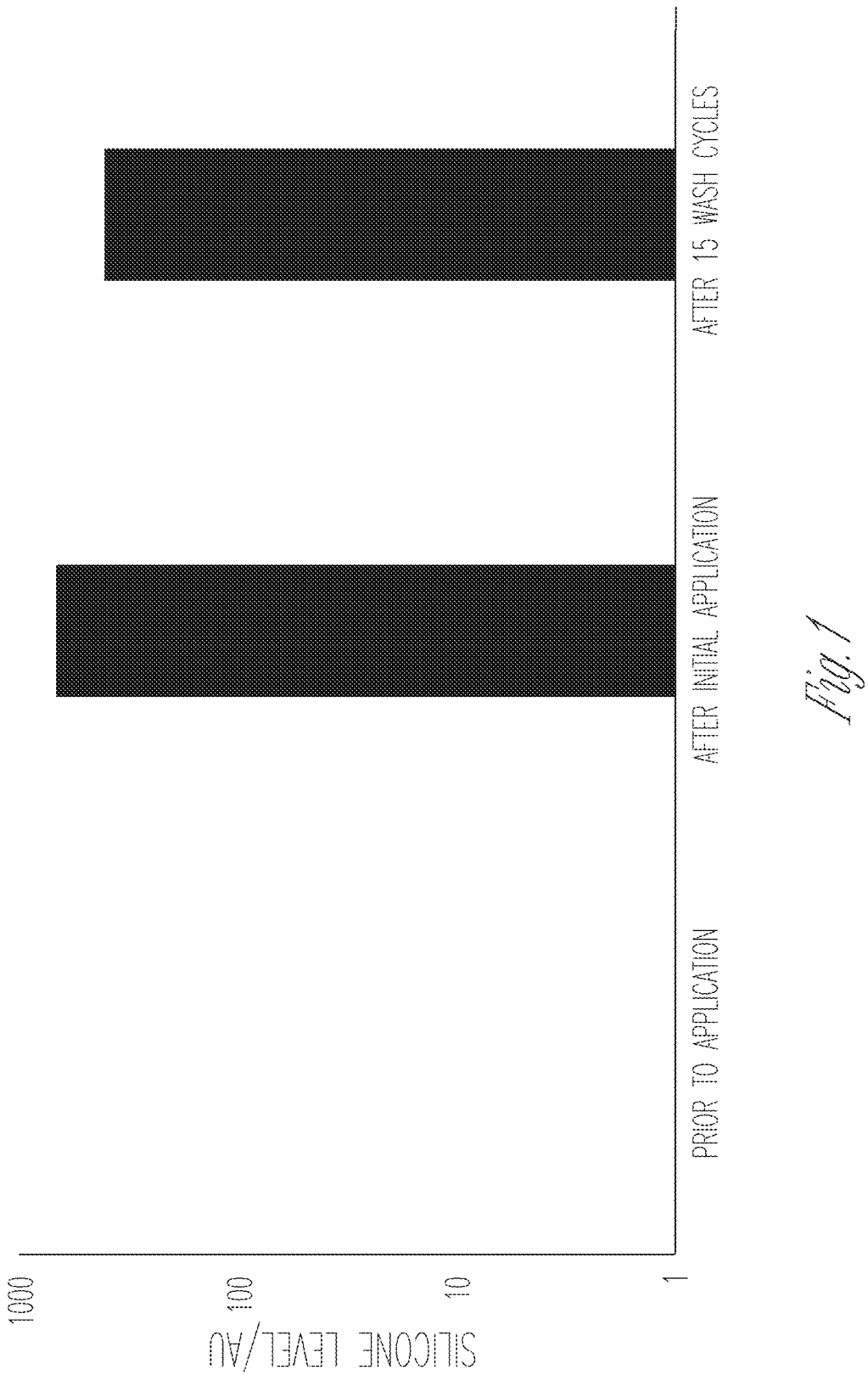
FIG. 1. Graph showing the level of silicone measured on hair prior, after application of the multicomponent composition and subsequent 15 washing cycles.

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise The term "may" in the context of this application means "is permitted to" or "is able to" and is a synonym for the term "can." The term "may" as used herein does not mean possibility or chance.

The term and/or in the context of this application means one or the other or both. For example, an aqueous solution of A and/or B means an aqueous solution of A alone, an aqueous solution of B alone and an aqueous solution of a combination of A and B.

The molecular weight of a polymer or oligomer used according to the invention may be measured by a weight average molecular weight, and the distribution of molecules of different molecular weights of a polymer or oligomer used according to the invention is determined by its polydispersity index. Molecular weight is expressed as daltons (D), kiloDaltons (KDa) and megaDaltons, which is million daltons or (MDa). The acronym $M_W$ stands for weight average molecular weight, $M_n$ is the number average molecular weight of a given polymer. Polydispersity is a unit-less number and indicates the breadth of the distribution of the polymer molecular weights and is defined as the $M_w/M_n$.

The term "about" is understood to mean±10 percent of the recited number, numbers or range of numbers.

The term "about 0 wt %" is understood to mean that no substance, compound or material to which zero (0) refers is present, up to a negligible but detectable amount is present, assuming that the detectability can be determined on a parts per million basis.

In addition, where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4. Similarly, values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

Substrate material is an all-encompassing class of substances and things that can be coated with embodiments of the present composition. Substrate material includes the subclass keratin material as well as non-keratin substances such as textiles, paper and any non-keratin material or thing that is to be coated with a compositional embodiment according to the present invention. Keratin material is a subclass of substrate material and includes human scalp hair, eyebrows, eyelashes, skin, nails, animal hair, natural keratin material as defined below and synthetic and semisynthetic hair and hair extensions. Synthetic and semisynthetic hair means material constructed of natural and/or synthetic polymer fibers, filaments, threads or sheets and the like and provides a material that has tactile, surface chemistry and visual appearance similar to natural keratin material such as natural hair. Keratin fiber is a subclass of keratin material and includes hair of all kinds and nails but does not include skin.

Hair and hair strands mean natural or synthetic keratin material, lair, hair strands and keratin material are used interchangeably in this document. Natural keratin material includes those from mammals and/or on mammals including human, primate, ruminant, camelid, equine, rodent and neovison including but not limited to cow, sheep, deer, goat, buffalo, lama, alpaca, camel, guanaco, vicuna, horse, antelope, moose, elk, rat, mouse, beaver, rabbit, mink, monkey, ape and similar species. Natural keratin material may include hair, fur or nails. Synthetic fibers include polyamides, polyacrylic and polyester fibers, especially polyamide fibers which are used for artificial hair implantation.

As used herein, the terms "covalent, coordinate, electrostatic, ionic, dipolar and entanglement or entwining interactions" mean a chemical relationship between two atoms or two groups of atoms. The interaction includes a covalent bond between the atoms such as the covalent bond between the two carbons of ethane. The interaction includes a coordinate bond between two or more atoms such as the coordinate bond between oxygen and sulfur of the sulfate anion ($SO_4^{-2}$) or a complex of zinc and EDTA. The interaction includes an electrostatic or ionic interaction between two charged atoms or particles such as the interaction between sodium and chloride of salt or between ammonium and acetate of ammonium acetate. Dipolar interaction includes hydrogen bonding such as the interaction between water and the hydroxyl of methyl alcohol. The interaction includes entanglement or entwining which is lipophilic interaction or mechanical/physical twisting together such as is present in the molecules of polyethylene.

As used herein, the term "transfer resistance" generally refers to the quality exhibited by compositions that are not readily removed by contact with another material, such as, for example, an item of clothing or the skin. Transfer resistance can be evaluated by any method known in the art for evaluating such transfer. For example, transfer resistance of a composition can be evaluated by the amount of product transferred from a wearer to any other substrate after the expiration of a certain amount of time following application of the composition to the hair. The amount of composition transferred to the substrate can then be evaluated and compared. For example, a composition can be transfer resistant if a majority of the product is left on the wearer's hair. Preferably little or no composition is transferred to the substrate from the hair.

As used herein, the term "minimally alters the keratin material or fibers, upon application" generally means that after removal of the composition coating on the keratin material such as hair, the keratin material is returned to a substantially unaltered state. The state of the keratin material such as hair can be assessed for example using ATR FT-IR for oxidative damage as described later or through tensile testing methods known to those skilled in the art for assessing fiber strength for example using equipment such as those designed and sold by Dia-Stron™.

As used herein, the term "setting" means converting the multicomponent composition to a solid coating through the application of means designed to remove or otherwise separate the medium from the other constituents of the multicomponent composition so as to leave a solid coating of the organic polymer, in situ linking material and base compound and other optional ingredients of the composition.

"Aliphatic substituent, group or component" refers to any organic group that is non-aromatic. Included are acyclic and cyclic organic compounds composed of carbon, hydrogen and optionally of oxygen, nitrogen, sulfur and other heteroatoms. This term encompasses all of the following organic groups except the following defined aromatic and heteroaromatic groups. Examples of such groups include but are not limited to alkyl, alkenyl, alkynyl, corresponding groups with heteroatoms, cyclic analogs, heterocyclic analogs, branched, dendritic, star or fullerene-like and linear versions and such groups optionally substituted with functional groups, as these groups and others meeting this definition of "aliphatic" are defined below.

"Aromatic substituent, group or component" refers to any and all aromatic groups including but not limited to aryl, aralkyl, heteroalkylaryl, heteroalkylheteroaryl and heteroaryl groups. The term "aromatic" is general in that it encompasses all compounds containing aryl groups optionally substituted with functional groups (all carbon aromatic groups) and all compounds containing heteroaryl groups optionally substituted with functional groups (carbon-heteroatom aromatic groups), as these groups and others meeting this definition of "aromatic" are defined below.

As used herein, the term "optionally" means that the corresponding substituent or thing mayor may not be present. It includes both possibilities.

"Alkyl" refers to a straight or branched, dendritic, star or fullerene-like or cyclic hydrocarbon chain group consisting solely of carbon and hydrogen atoms, unless otherwise specifically described as having additional heteroatoms or heterogroups. The alkyl group contains no unsaturation, having from one to twenty four carbon atoms (e.g., $C_1$-$C_{24}$ alkyl). Whenever it appears herein, a numerical range such as for example but not limited to "1 to 24" refers to each integer in the given range; e.g., "1 to 24 carbon atoms" means that the alkyl group may consist of 1 carbon atom, 2 carbon atoms, 3 carbon atoms, etc., up to and including 24 carbon atoms, although the present definition also covers the occurrence of the term "alkyl" where no numerical range is designated. In some embodiments, it is a $C_1$-$C_4$ alkyl group. In other instances it is a $C_1$-$C_6$ alkyl group and instill other instances it is a $C_1$-$C_{24}$ alkyl group Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like.

"Alkylenyl" refers to a straight or branched, dendritic, star or fullerene-like divalent hydrocarbon chain consisting solely of carbon and hydrogen atoms, unless otherwise specifically described as having additional heteroatoms or heterogroups. The alkylenyl group contains no unsaturation has a valence bond at either end of the chain and has a numerical range of carbon atoms of 1 to 24, which numerical range includes each integer in the range. An example of a divalent hydrocarbon chain designated as an alkylenyl group is —$CH_2$—$CH_2$—$CH_2$—$CH_2$— which is butylenyl.

"Cycloalkyl" is a subcategory of "alkyl" and refers to a monocyclic or polycyclic group that contains only carbon and hydrogen, and may be saturated, or partially unsaturated. Cycloalkyl groups include groups having from 3 to 24 ring atoms (i.e., $C_3$-$C_{24}$ cycloalkyl). Whenever it appears herein, a numerical range such as but not limited to "3 to 24" refers to each integer in the given range; e.g., "3 to 24 carbon atoms" means that the cycloalkyl group may consist of 3 carbon atoms, etc., up to and including 24 carbon atoms. In some embodiments, it is a $C_3$-$C_8$ cycloalkyl group. In some embodiments, it is a $C_3$-$C_5$ cycloalkyl group. Illustrative examples of cycloalkyl groups include but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

"Alkoxy" refers to the group —O-alkyl, including from 1 to 24 carbon atoms of a straight, branched, dendritic, star or fullerene-like, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl is an alkyl group which encompasses both straight and branched, dendritic, star or fullerene-like chain alkyls of from 1 to 4 carbon atoms.

"Amino" or "amine" refers to an —$N(R^a)_2$ group, where each $R^a$ is independently hydrogen or linear, branched, dendritic, star or fullerene-like or cyclic alkyl of 1 to 6 carbons. When an —$N(R^a)_2$ group has two $R^a$ groups other than hydrogen, they can be combined with the nitrogen atom to form a 4-, 5-, 6-, or 7-membered ring.

"Aryl" refers to a conjugated pi ring or multiple rings with six to twenty two ring atoms. The aryl group has at least one ring having a conjugated pi electron system which is carbocyclic (e.g., phenyl, fluorenyl, naphthyl and anthracenyl). Included are partially saturated aryl rings such as tetrahydro naphthyl.

"Heteroalkyl" "heteroalkenyl" and "heteroalkynyl" include optionally substituted alkyl, alkenyl and alkynyl groups and which have one or more skeletal chain atoms selected from an atom other than carbon, e.g., oxygen, nitrogen, sulfur, phosphorus or combinations thereof. A numerical range may be given, e.g. $C_1$-$C_{24}$ heteroalkyl which refers to the chain length in total, which in this example may be as long as 24 atoms long. For example, a —$CH_2OCH_2CH_3$ group is referred to as a "$C_4$" heteroalkyl, which includes the heteroatom center in the atom chain length description. Connection to the rest of the molecule may be through either a heteroatom or a carbon in the heteroalkyl chain.

"Heteroaryl" or heteroaromatic refers to a 5, 6 or 10-membered aromatic group (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system or a conjugated ring system such as cyclopentadienyl optionally with a bridging atom providing conjugation such as pyrrole or ferrocenyl. Whenever it appears herein, a numerical range refers to each integer in the given range. An N-containing "heteroaromatic" or "heteroaryl" moiety refers to an aromatic group in which at least one of the skeletal atoms of the ring is a nitrogen atom. The polycyclic heteroaryl group may be monocyclic or non-monocyclic. The heteroatom(s) in the heteroaryl group is optionally oxidized. One or more nitrogen atoms, if present, are optionally quaternized. The heteroaryl is attached to the rest of the molecule through any atom of the ring(s). Examples of heteroaryls include, but are not limited to pyrrolyl, furanyl, thiophenyl, imidazolyl, pyranyl, pyridinyl, pyrimidinyl, benzimidazole, benzothiophenyl, quinolinyl, quinazolinyl, and similar heteroaryl compounds of 6 to 12 carbons and 1, 2 or 3 heteroatoms including any combination of nitrogen, oxygen and sulfur.

"Heterocyclic" refers to any monocyclic or polycyclic moiety comprising at least one heteroatom selected from nitrogen, oxygen and sulfur. As used herein, heterocyclyl moieties can be aromatic or nonaromatic. The moieties heteroaryl and heterocyclyl alkyl are members of the heterocyclic group.

The terms "In situ linking" and "in situ linkable" and "Cross linkable" mean the potential at a future time to form covalent bonds, coordinate linkages, ionic linkages, electrostatic linkages, polar couplings, hydrogen bonds and polymer entanglement to provide interactions and/or connections between molecules. The terms "in situ linked" and "cross linked" mean that in the present state, covalent bonds, coordinate linkages, ionic linkages, electrostatic linkages, polar couplings, hydrogen bonds and entanglement arrangements have already occurred.

"in situ" is a latin phase meaning in its original place. In the context of this invention, it means an activity such a cross linking that takes place on the hair.

Zeta potential relating to pigment microparticles means the electro kinetic potential of extremely small particles suspended in colloidal dispersions. It is caused by the net electrical charge at the particle interface with the suspending fluid. It is an indicator of the stability of a colloidal dispersion. The magnitude indicates the degree of electrostatic repulsion between adjacent similar charged particles in a dispersion. At zero or minimal + or − potential, rapid coagulation can occur. At a + or − zeta potential above about 40, good colloidal stability is maintained. Zeta potential can be measured using approaches known to those skilled in the art. For example a Zetasizer Nano Z from Malvern Panalytical Ltd, Malvern U.K. may be used to assess the zeta potential of the components.

The term "textile" as used herein has its ordinary and customary meaning and includes cloth, fabric or other material made out of natural plant fibers, synthetic fibers, metal fibers, carbon fibers, animal fibers such as may be derived from feathers, sinew, ligament, muscle and/or bone. The fibers are combined by weaving, felting, gluing, tacking, spinning, extruding, blowmelting or other-wise formed into at least a somewhat coherent mas typically considered to be cloth, fabric, sponge rubber, foam, woven or nonwoven material. Rugs, bedsheets, clothing, coats, hats, underwear, socks, seat covers, seat cushions, pillows, and similar materials are textiles. Included also is paper made of plant or synthetic material such as typing paper, writing paper, foil, parchment papers, wax paper, aluminum foil and similar flat, thin materials.

DETAILED DESCRIPTION

Embodiments of the instant invention generally relate to the multicomponent composition and techniques for its use to provide a coating with optional pigment microparticles on the surfaces of substrate material, and especially on keratin material. The coating is formed by treatment of the substrate material, especially keratin material such as hair with the embodiments of the multicomponent composition that can be manipulated for constituents and application technique to provide a coating that is readily removable by simple washing such as by ordinary shampooing or has significant remanence so that the coating withstands multiple washings with little or no change in its characteristics. As a remanent coating that is wash resistant, the coating is designed so that use of a triggering formulation will remove the coating without damage to the substrate material such as hair. The embodiments of the multicomponent composition minimize or avoid damage to keratin proteins within the keratin material, particularly after repeated dying events. The embodiments of the multicomponent composition limit irritation of the scalp which may result from application of known hair dye compositions. The present invention is directed to embodiments of multicomponent compositions for coating of keratin material in such a way that the coating can be applied and can be easily removed with a simple shampooing or can be applied and will remain and resist shampooing and other wash techniques until it is desired to remove the coating by a trigger removal composition. This makes the treatment process more pleasurable for the user and or stylist. It is also desired that the results are predictable, enabling the users to achieve their target hair coating result.

The composition, method and coating aspects of the invention are directed to embodiments of a multicomponent composition that are adapted to provide coating embodiments on the surfaces of keratin material, especially hair strands. The coating embodiments have remanence that enables them to remain in somewhat to substantial to essential in original condition especially upon the hair embodiment of keratin material through at least a series of washings with diluted aqueous media containing soap and/or shampoo. The multicomponent composition embodiments minimally alter keratin material upon their application.

The embodiments of the multicomponent composition according to the invention comprise first and second components as well as the optional but preferred third components which meld together in situ on substrate material, especially on keratin material and most especially hair, to form a coating that surprisingly is durable and resistant to repeated washings with ordinary shampoos, soap, detergent and water. The first, second and optional third components comprise constituents with complementary first and second functional groups and optional third functional groups of the optional third component that in situ form covalent, coordinate, entanglement, electrostatic, ionic and/or dipolar linkages. It is believed that the melding together to form in situ linkages produces an arrangement of coating, optional microparticles and substrate material surfaces that are interconnected and develop the unexpected, surprising long standing remanence.

Embodiments of the invention also include methods for preparation of the multicomponent composition, kits for storage and delivery of the multicomponent composition, methods for application of the multicomponent composition to substrate material, especially keratin material such as hair, the easily removable to essentially permanent costing on substrate material as well as methods for on demand removal of the coating on substrate material, especially keratin material such as hair so that the substrate material is minimally altered. As used herein, the term "minimally alters the substrate material" generally means that after removal of the coating composition, the substrate material and especially keratin material is returned to a substantially unaltered state.

The Multicomponent Composition

First and Second Compounds

The multicomponent composition comprises first, second and optional third components with optional fourth component for production of a remanent or temporary coating on substrate material and especially on keratin material and fibers such as hair. The components interact in situ to provide covalent bonding among the first and second components and optional third component and the substrate material. The optional third and fourth components are discussed in separate sections below.

The first and second components which form a part of the embodiments of the multicomponent composition include as in situ reactive constituents linear, branched, cage, cyclic, dendritic, star or fullerene-like organic compounds and linear, branched, cage, cyclic or dendritic silicone compounds with pendant and/or terminal functional groups that are complementary reactive pairs. Preferred configurations of the organic and silicone compounds are the linear and branched arrangements. Especially preferred configurations are the linear arrangements. The compounds comprise organic or silicone compounds which include the complementary functional groups. The complementary functional groups include $\alpha,\beta$ unsaturated carboxyl groups (hereinafter olefinoyloxy group) and amine/nitrogen groups. These two complementary functional groups combine through a nucleophilic addition of the amine/nitrogen to the olefinic bond of the $\alpha$, $\beta$ unsaturated carboxyl group to form a nitrogen-carbon bond. This nucleophilic addition is also known as the "Michael Addition." While the nitrogen and/or amine group is the preferred nucleophile in this regard, thiol or mercaptan groups and carboxylate groups may also be employed for the same purpose. For these versions of nucleophiles, the second component may be modified to present sulfur nucleophiles or carboxylate nucleophiles instead of or in addition to nitrogen nucleophiles. Additionally, the first component with the pendant $\alpha$, $\beta$ unsaturated carboxyl ester group may also contain carboxylic acid or protected carboxylic acid groups. Upon neutralization with a base such as weak carbonate or hydroxide or upon deprotection to produce carboxylate anions, the carboxylate may function as a nucleophile and add to the pendant $\alpha$, $\beta$ unsaturated carboxyl ester groups. In this embodiment, the first component may be enabled to be self-reactive to provide cross linking in addition to or in replacement of the combination with the second component. In a similar fashion, a pendant thiol/mercaptan group which can function as a nucleophile as an —SH group can alternatively be treated with a base such as hydroxide to produce a thiol anion which will function as a stronger nucleophile if desired.

The linear, branched, dendritic, star, cage, cyclic or fullerene-like organic compound or linear, branched, cage, cyclic or dendritic silicone compound (preferably linear and/or branched organic and silicone compounds) comprises a small molecule, a monomeric group, an oligomer or polymer having at least two and at least preferably three complementary functional groups. The functional groups are complementary in that they react together in situ with minimal activation energy to provide cross linked first and second compounds. When the third compound is also present, it may also enter into the nucleophilic addition to provide additional cross-linking and also interacts through electrostatic and lipophilic activity. The complementary functional groups covalently bond together in situ to meld together the first, second and third components to form a remanent coating. The coating also includes ionic, electrostatic, entanglement and/or coordination interactions between the molecules of these components and also between the components and the surfaces of the substrate material, preferably keratin material.

The reactive functional groups are distributed throughout the frame of the small molecules and along and within the backbones and branch chains of the monomeric group, the oligomer and the polymer of the first and second compounds. The distribution may be random or ordered or at certain designated positions within and/or along the first and second compounds. Preferably, the distribution of the functional groups within the first and second compounds is random. The reactive functional groups comprise olefinoyloxy groups and amine/nitrogen groups. The complementary functional groups can react together under ordinary environmental conditions and/or can react together with the help of a fourth component such as catalyst or substance that will lower the reaction activation energy needed for the reactive bonding of the functional group pair. Treatment with heat such as by a hot air blower, hot iron or other heat producing device may facilitate the reaction of the first and second functional groups.

With the understanding that first and second compounds are two separate and distinct compounds, the structural details of the compounds with complementary functional groups are described in greater detail in the following passages.

The First and Second Functional Groups, Formulas I and II

With appropriate selection of the functional groups on the compounds, cross linking, net and/or star formation of the coating can be achieved. The complementary reactive pair functional groups can be designated as X and Y groups. The X and Y groups include connector units $R^1$ and $R^4$ that respectively join the olefinoyl/olefinoyloxy and amine/nitrogen groups to the remainder of the first and second compounds. These reactive functional units for the first and second compounds respectively have Formulas I and II:

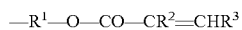    Formula I:

    Formula II:

As mentioned above, the first and second compounds respectively have at least two and preferably at least three functional units per molecule.

For Formula I, $R^1$ is a linear or branched alkyl group of 1 to 12 carbons optionally with one or more heteroatoms in or on the alkyl chain, a cycloalkyl-alkyl or cycloalkyl group of 3 to 12 carbons optionally with one or more heteroatoms in or on the cycloalkyl ring and/or alkyl chain, an arylalkyl group of 6 to 20 carbons optionally with one or more heteroatoms in or on the alkyl chain, an aryl group of 6 to 20 carbons, or a heteroaryl group of 6 to 20 carbons containing one or more heteroatoms. The heteroatoms may be oxygen, nitrogen and/or sulfur in the chain and/or alternatively or in addition may be hydroxyl or amine on the chain as substituents attached to $R^1$. Preferably the heteroatom may be a hydroxyl substituent of $R^1$ that is especially and preferably in a position to form a pseudo seven member hydrogen bonding ring with the carbonyl of the olefinoyloxy group. $R^2$ and $R^3$ may be hydrogen or an alkyl group of 1 to 4 carbons. Preferably when one or both of these groups is alkyl, the alkyl is methyl. When $R^2$ is hydrogen and $R^3$ is hydrogen, the olefinoyloxy group is an acryloxy group. When $R^2$ is methyl and $R^3$ is hydrogen, the olefinoyloxy group is a methacryloxy group. When $R^2$ is hydrogen and $R^3$ is methyl, the olefinoyloxy group is a crotonyloxy group. When $R^2$ is methyl and $R^3$ is methyl, the olefinoyloxy group is a 2-methyl-2-butenoic acid or tiglic acid.

For Formula II, each $R^4$ independently is a free valence bond, hydrogen or $—R^{4a}$. When two or three $R^4$ groups are free valences, the nitrogen is part of a small molecule frame or is a nitrogen in the backbone, chain or side chain of a monomeric group, an oligomer or a polymer. Multiple nitrogens in such a small molecule frame, backbone, chain or side chain is typical and usual. Examples include linear and branched polyethylene imine, polypropylene imine as well as di, tri, tetra, penta ethylenylamine. An example is triethyleneimine which has the formula $CH_3CH_2—NH—CH_2CH_2—NH—CH_2—CH_2—NH_2$. As Formula II, this example has $—NH—$ in the chain with ethyl being one selection of $R^{4a}$ ethylenyl with two free valences being a second selection of $R^{4a}$ and ethyl amine being a third selection of $R^{4a}$.

When $R^4$ is other than a free valence, it may be hydrogen or $—R^{4a}$. The group $—R^{4a}$ binds Formula II to the remainder of the second compound when Formula II is a pendant amine group such as for example, ethylenyl amine $—CH—_2CH_2NH_2$. In this instance. $R^{4a}$ has two free valences. Another embodiment of $—R^{4a}$ provides that it has a single valence substituent of nitrogen such as a methyl group or an ethylamine bonded to nitrogen. In general, the group $—R^{4a}$, comprises a linear or branched alkyl of 1 to 12 carbons optionally substituted by a primary amine group and optionally containing with one or more heteroatoms in the linear or branched alkyl chain, a cycloalkyl-alkyl or cycloalkyl of 3 to 12 carbons optionally substituted by a primary amine group and optionally containing one or more heteroatoms in the cycloalkyl ring and/or alkyl chain, an arylalkyl of 6 to 20 carbons optionally substituted by a primary amine group and optionally containing one or more heteroatoms in the alkyl chain, an aryl group of 6 to 20 carbons optionally substituted by a primary amine group, or a heteroaryl group of 6 to 20 carbons containing one or more heteroatoms and optionally substituted by a primary amine group. Thus, the group $—R^{4a}$ can be a double valence group so that it functions as a connecting group to bond the nitrogen to the second compound. In its single valence embodiment, $—R^{4a}$ functions as a nitrogen substituent such as a methyl or an ethylamine group bonded to the nitrogen. The free valence (-) in these instances for $—R^{4a}$ can bind it to nitrogen and to the remainder of the second compound as a double free valence or it can bind $R^{4a}$ only to nitrogen as a single free valence. The one or more heteroatoms independently of $R^{4a}$ may be nitrogen, oxygen, sulfur or a combination thereof.

The $R^1$ and $R^{4a}$ groups of Formulas I and II may also provide additional pendant organic chains to which the functional groups are bonded. The $R^1$ and $R^{4a}$ groups may be linear and/or branched saturated aliphatic chains or linear and/or branched saturated heteroaliphatic chains of one to forty-eight carbons, preferably one to twenty-four carbons, more preferably one to twelve carbons, or aromatic and/or heteroaromatic groups of one, two or three separate or fused rings, each ring being a 5 or 6 single ring, or a bicyclic 10 member ring as described in the Definitions Section. The $R^1$ and $R^{4a}$ groups may also be combinations of the saturated aliphatic and/or heteroaliphatic chains and the aromatic and/or heteroaromatic groups. The aliphatic chains may be linear and/or branched, dendritic, star or fullerene-like polymethylenyl chains. The $R^1$ and $R^{4a}$ groups heteroaliphatic chains may be linear and/or branched, polymethylenyl chains in which parts of the polymethylenyl chains are linked together by heteroatom linking groups such as ether, sulfur, amino, carboxyl, amido, urethano, ureido, carbonyl, carbonato and/or imino. The heteroatom linking groups preferably are compatible with the olefinoyl/olefinoyloxy and amine functional group chosen for an embodiment of the compound. Exemplary aromatic and heteroaromatic rings include phenyl, naphthyl, thiophenyl, pyridinyl, pyrazinyl, quinolinyl, quinazolinyl, imidazolyl, benzimidazolyl, thiazolyl, benzothiazolyl, indolyl, indenyl, indanyl and similar aromatic and heteroaromatic groups.

Number and Distribution of Formulas I and II in First and Second Compounds

The compounds (e.g. first and second compounds) are linear, branched, dendritic, star or fullerene-like compounds with at least two functional groups and preferably at least three functional groups per molecule. In terms of the well-understood polymer nomenclature, the monomer group, the oligomer and the polymer may have branching of the backbone and cross link, dendritic and/or star and/or fullerene-like arrangements among these backbones. Preferably, very few branch and/or cross link and/or dendritic and/or star and/or fullerene-like arrangements, if any, are present in the organic compounds and very few branch and or cross link and/or dendritic arrangements, if any are present in the silicone compounds. More preferably, the compounds primarily have linear backbones with optional short chain branching and little or no cross link, dendritic or star arrangements between and among individual molecules of a first compound or a second compound.

The preferred arrangement of the functional groups in each of the first and second compounds provides that the functional group individually and separately is present at a minimum number of two, preferably three or more per compound molecule and may be distributed throughout the small molecule frame, the monomer group, oligomer or polymer backbone and/or along their branch chains. The distribution may be random, ordered or at certain designated positions, such as termini and the like. Preferably the distribution is random and the molecular space between functional groups on a molecule of a first compound or a second compound typically is an average and may have significant standard deviation. More preferably, the number is at least four distributed throughout the compound. In addition, multiple functional groups may be present at a single position on the small molecule frame as well as on the backbone and especially on branch chains of the monomer group, oligomer or polymer. The number of a particular functional group present in a molecule can be assessed by calculating the number average compound molecular weight divided by the functional group equivalent weight where the equivalent weight refers to the mass of polymer which has one equivalent reactive group. If this calculation gives a value of 2, this shows that the average polymer has two functional groups.

Examples of $R^1$ and $R^{4a}$ Groups

Some examples of the aliphatic groups as a polymethylenyl chain, the heteroaliphatic group as a heteropolymethylenyl chain and the aromatic/heteroaromatic group of the of $R^1$ and $R^{4a}$ groups may comprise but are not limited to any of the following divalent formulas of charts I, II, III and IV. In these charts, the group My represents methylenyl (—$CH_2$—), the group Me represents methyl (—$CH_3$), the group Bz represents phenylenyl (a benzene ring with two free valences), the group Py represents pyridylenyl (a pyridine ring with two free valences), the group Th represents thiophenylenyl with two free valences and the group Bi represents benzimidazolylenyl with two free valences. The left and right valences of these examples of these groups may be bonded respectively to the remainder of the first and/or second compounds of Formulas III, IV, V and VI below. The group $R^{20}$ is a branch polymethylenyl group ending with a methyl group and may have from one to twelve carbons (with one carbon, $R^{20}$ is methyl). The heteroatoms are selected so that they would not interfere with the Michael reaction of the functional groups.

CHART I

| Saturated Aliphatic $R^1$ and $R^{4a}$ Groups | |
| --- | --- |
| -My- | -My-My(Me)-My- |
| -My-My- | -My-My-My($R^{20}$)-My-My-My- |
| -My-My-My- | -My-My-My($R^{20}$))-My- |
| -My-My-My-My- | -My-My-My($R^{20}$)-My-My- |
| -My-My-My-My-My- | -My-My(My-My-My-My-Me)My-My-My-My- |
| -My-My-My-My-My-My- | -My-My-My-My-My(Me)My- |

CHART II

| Saturated Heteroaliphatic $R^1$ and $R^{4a}$ Groups | |
| --- | --- |
| -My-O-My-O-My- | -My-My-My-O-My-My-My-O-My-My-My- |
| -My-My-O-My-My-O-My-My-O-My-My | -My-My-My-CHOH-My-My($R^{20}$)-My-O-My-My-My- |
| -My-My-My-$NR^3$-My-My-O-My-My- | -My-My-MyCHO$R^3$-My-My(My-Me)-O-My-My-My- |
| -My-My-My-CHOH-My-My-O-My-My- | -My-CHOH-My-My-My-$NR^3$-My-My-My- |
| -My-My-My-My-CHOH-My-My-$NR^3$-My-My-My- | -My-My-My-O-My-O-My- |
| -My-My-My-O-My-My-My-$NR^3$-My-My-My- | -My-My-My-$NR^3$-My-My-My-$NR^3$-My-My-My- |
| -My-My-My-CHOH-My-My-My-O-My-My-My- | -My(Me)-My-O-My(Me)-My-O-My(Me)-My-O-My(Me)-My-O-My(Me)-My- |
| -My-My-My-CHOH-My-My-My- | -My-My-My-My(My-My-My-My-Me)-O-My-My- |
| -My-My-My-CHOH-My($R^8$)-My- | -My-My-My-O-My-My($R^8$)-My-O-My-My-My- |
| -My-My-My-$NR^3$-My($R^8$)-My- | -My-My-My-CHOH-My($R^8$)-My-O-My-My-My- |
| -My-My-O-My(Me)-My-O-My-My-O-My(Me)-My-O-My-My-O-My(Me)-My-O-My-My- | -My-My(OH)-My-My-O-My-My- |
| -My-My-O-My-My(MyOH)-My-My-O-My-My(Me)-My-My | -My-My(OH)-My-My-$NR^3$-My-My- |

CHART III

| Additional Saturated Heteroaliphatic $R^1$ and $R^{4a}$ Groups | |
| --- | --- |
| -My-NH-My-O-My- | -My-My-My-$CO_2$-My-My-My-O-My-My-My- |
| -My-My-My-S-My-My-My- | -My-My-My-CHOH-My-My($R^{20}$)-My-O-My-My-My- |
| -My-My-My-$NR^3$-My-My-CONH-My-My- | -My-My-MyCHO$R^3$-My-My(My-Me)-O-My-My-My- |
| -My-My-My-CHOH-My-My- | -My-CHOH-My-My-My-$NR^3$-My- |

CHART III-continued

Additional Saturated Heteroaliphatic $R^1$ and $R^{4a}$ Groups

| | |
|---|---|
| CONH-My-My- | My-My- |
| -My-My-My-My-CHOH-My-My- | -My-My-My-CONH-My-O-My- |
| My-NR³-My-My-My- | |
| -My-My-My-NHCOO-My-My- | -My-My-My-NR³-My-My-My- |
| My-NR³-My-My-My- | CONR³-My-My-My- |
| -My-My-My-CHOH-My-My-My- | -My-My-My-My-NHCOO-My- |
| O-My-My-My- | My-My-My-My-My-My- |
| -My-My-My-NHCOO-My-My- | -My-My-My-My(My-My-My-My- |
| My- | Me)-OCONH-My-My-My- |
| -My-My-My-CHOH-My(R²⁰)-My- | -My-My-My-O-My-My(R²⁰)-My-O- |
| My- | My-My-My- |
| -My-My-My-NR³-My(R²⁰)-My- | -My-My-My-CHOH-My(R²⁰)-My- |
| My- | My-OCONH-My-My-My- |

CHART IV

Aromatic and Heteroaromatic $R^1$ and $R^{4a}$ Groups

| | |
|---|---|
| -Bz-Bz-O-Bz-Bz-O-My-My-O-My-My | -My-My-Bz-My-My- |
| -Bz-O-My-My- | -My-Bz-My- |
| -Bz- | -My-Py-My- |
| -Py- | -My-My-Py-My-My- |
| -Bz-Py-O-Bz-O-My-My- | -My-O-Bz-O-My- |
| -O-Bz-My- | -O-Py-My- |
| -O-Bz- | -O-Py- |
| -Th- | -Bi- |
| -My-Th-My- | -My-Bi-My- |

Preferred $R^1$ and $R^{4a}$ groups include monomethylenyl, trimethylenyl, hexamethylenyl, methylenyl-[branch dimethylenylmethyl)]-methylenyl and tetramethylenyl-[branch methylenylmethyl]-methylenyl. More preferred $R^1$ and $R^{4a}$ groups include monomethylenyl, trimiethylenyl, tetramethylenyl, hexamethylenyl and dimethylenyl-[branch methylenylmethyl]-dimethylenyl, divalent benzylenyl, divalent pyridylenyl, methylenyl-benzylenyl, methylenyl-pyridylenyl, thiophenylenyl, quinolinylenyl, benzimidazolylenyl and dimethylenyl-benzylenyl-dimethylenyl.

Preferred embodiments of olefinoyloxy groups for Formula I include the following alkenoyloxy moieties in which n is an integer from 1 to 10 with 3 being most preferred. In addition, preferred embodiments include the following alkenoyloxy moieties in which hydroxyl (OH) is changed to hydrogen.

i) $-(CH_2)_nOC(O)C(CH_3)=CH_2$, $-(CH_2)_nOC(O)C(H)=CH_2$,
ii) $-(CH_2)_nOCH_2CH(OH)CH_2OC(O)C(CH_3)=CH_2$,
iii) $-(CH_2)_nOCH_2CH(OH)CH_2(C(O)C(H)=CH_2$,
iv) $-(CH_2)_n[O(CH_2)_2]_q[O(CH_2)CH(CH_3)]_rOC(O)C(CH_3)=CH_2$, where r+q is greater than 1 and less than 10
v) $(CH_2)_n[O(CH_2)_2]_q[O(CH_2)CH(CH_3)]_r$ $OC(O)C(H)=CH_2$, where r+q is greater than 1 and less than 11.

Preferred embodiments of amino for Formula II include:
i) $-(CH_2)_3NH_2$,
ii) $-CH_2CH(CH_3)CH_2NH_2$,
iii) $-(CH_2)_3NH(CH_2)_2NH_2$,
iv) $-CH_2CH(CH_3)CH_2NH(CH_2)-NH_2$,
v) $-(CH_2)NH_2$,
vi) $-(CH_2)NH(CH_2)_2NH_2$.
vii) $-(CH_2)_3N((CH_2)_2NH_2)_2$.

In addition to Formulas I and II being a single occurrence on a first and second compound respectively, the foregoing Formulas and description show that Formulas I and II may be multiple occurrences on a single first and second compound respectively.

Generally, the small molecule molecular weight may be in the range of from about 250 Da to about 2500 Da. The average number of monomeric units of the first and second compounds as oligomers may each independently be in a range from of about 10 to about 20 units. The average number of monomeric units of the first and second compounds as polymers may each independently be in a range of at least about 20, preferably a monomeric unit average of from about 20 to about one million, more preferably a monomeric unit average in a range of about 20 to about 20,000. For oligomers and polymers, the number of monomeric units per molecule will vary for the same reasons that the molecular weight varies. The units and molecular weights are determined as averages while the numbers and weights are spread across a range substantially as a gaussian distribution. The weight average molecular weight ranges of the small molecule, oligomer and polymer are provided in the following section. The dispersity of the spread indicates the extent of the variation of weights or units across the distribution. Typically, the dispersity may be in a range of at least 1.3, more preferably 1.5 to about 8, more preferably about 1.8 to 6. Because the unit weights of the actual monomeric units of the organic and silicone oligomers and polymers vary according to the atoms making up the units, the average number of units rather than weight average molecular weight expresses the size dimension of the oligomers and polymers irrespective of the identity of the monomeric units present.

In one embodiment, the properties of the coating produced by the combination of the first and second compounds and optionally the amine polymer as the base compound coupled with the reactive pairing of the first and second functional groups produces a coating with a Shore OO Hardness as set forth by the experimental data provided by the test method described in the examples section.

The in situ melding is affected by the number in situ linkages between and among the components providing the first and second compounds and the base compound. The in situ melding delivers primary control of the degree of network, dendritic and star interconnections among these components. With a moderate to large number of interconnections and/or higher average number of monomeric units in the first and second compounds and/or a short to moderate chain length distance between interconnections, the remanence of the coating is significant and can resist multiple washings without fading or removal. With a low to moderate number of interconnections and/or low average number of monomeric units in the first and second compounds and/or use of small molecules and/or a low number of monomers of the monomer group, the remanence of the resulting coating is significantly decreased so that the coating may be removed by shampooing such as one or two simple shampoo washings. In addition to this primary control, dilution of the first and second compounds with a non-reactive compound can help with coating flexibility and other physical parameters such as elasticity, inter-strand interaction for hair strands and tactile sensation. Dilution with non-reactive compounds can influence positively or negatively remanence depending upon such parameters associated with the non-reactive compounds such as water solubility, lipophilicity, molecular branching and non-covalent interaction with the first and/or second and/or third compounds. Modification of primary control may also be established by average weight and/or average molecular unit numbers of the first and/or second compounds, by the position of functional groups along the frame or chains of the first and second compounds and ancillary components such as surfactants, diluents, dispersants and other excipients discussed below.

The First and Second Organic Compounds, Formulas III, IV

The first and second organic compounds range from small molecules to monomeric groups to oligomers and polymers. This range cover, molecular weights to weight average molecular weights from low, on the order of a few hundred Da to very high, on the order of MDa. As small molecules, the frame of the compounds may be saturated aliphatic or aromatic, preferably saturated aliphatic. As monomeric groups, oligomers and/or polymers, the organic compounds may be repeating monomeric units of any coupling unit such as olefinic, ester, thioester, amide, urethane, thiourethane, urea, thiourea, ether, thioether, carbonate, thiocarbonate, and any other known and typical polymeric coupling unit such as is disclosed in "Advanced Organic Chemistry", J March, $4^{th}$ Ed., John Wiley & Sons, New York, 1992.

The monomeric groups include the monomer, dimer, trimer, tetramer, pentamer, hexamer, heptamer, octamer, nonamer and/or decamer. The oligomer includes monomeric units of a unit average of about 10 to about 20 units. The polymer includes monomeric units of a unit average of at least 20, preferably a monomeric unit average in a range of from about 20 to about one million, more preferably a monomeric unit average in a range of about 20 to about 20,000.

The frame of the small molecule or the repeating monomeric units of the monomeric group, oligomer or polymer may be appropriately modified to incorporate the functional group of Formula I or II. For example, a frame of the small molecule or a monomeric unit may be modified with an organic group $R^1$ or $R^{4a}$ bearing a protected hydroxyl or amine group. Following preparation of the remaining structure or the small molecule, monomeric group, oligomer or polymer, the protection moiety of the protected hydroxyl or amine group may be removed and an acid chloride of the olefinoyloxy group can be combined in a Schotten-Bauman reaction to bind the olefinoyloxy group with the precursor to produce the first organic compound. Alternatively, the frame or a monomeric unit can be modified with a pendant epoxy or thioepoxy or aziridine group. The (meth)acrylic acid or crotonic acid reactant can be combined with the epoxy, thioepoxy or aziridine to provide the olefinoyloxy bonded to the frame or monomeric unit of the monomeric group, oligomer or polymer. The pendant epoxy, thioepoxy or aziridine with a frame or monomeric unit can be prepared by addition of an α ω hydroxy olefin to a carboxylic acid group to form a frame or monomeric unit with a pendant ester group bearing an ω olefin group. The olefin can be converted to the epoxide, thioepoxide or aziridine to prepare the epoxy, thioepoxy or aziridine starting material.

For preparation of the functional group of Formula II bonded to the organic compound, the small molecule, monomeric group, oligomer or polymer may be prepared with pendant amine groups and/or frame and/or backbone/chain nitrogens according to known organic chemistry techniques. Many examples of these compounds are commercially available. Examples of additions include incorporation of protected vinyl amine or protected u t alkenyl amine into a monomer group, oligomer or polymer of a polyolefin, incorporation of a α ω diol or diamine with protected, pendant amine into a monomeric group, oligomeric or polymeric ester, amide, urethane, urea or incorporation of an aliphatic epoxide with protected amine into a monomeric group, oligomeric or polymeric polyether.

The first and second compounds as organic compounds are linear, branched, dendritic, star and/or fullerene-like compounds of Formulas III and IV. Preferably Formulas III and IV are linear or branched compounds, more preferably linear compounds.

$$X_a-R^5 \quad \text{Formula III:}$$

$$Y_b-(R^5)_r \quad \text{Formula IV:}$$

For Formula III, X is Formula I and at least two, preferably three X groups are bonded to at least two positions of $R^5$. This configuration of the organic compound, Formula III, places at least two and preferably at least three olefinoyloxy groups on the first organic compound. The distribution of X groups preferably may be random as discussed above. For Formula IV, Y is Formula II, and at least two Y groups are bonded to at least two positions of one $R^5$ and/or at least one Y group is bonded to at least two $R^5$ groups, or a combination these two bonding arrangements of Y and $R^5$. This configuration of the organic compound, Formula IV, placed at least two and preferably at least three amine/nitrogen groups on the second organic compound. The distribution of Y groups preferably may be random as discussed above. This configuration includes two kinds of amine/nitrogen placements. The amine groups can be pendant from the frame of the organic small molecule or from the chain, backbone or side chain of the organic monomeric group, oligomer or polymer. The amine/nitrogen groups can be within and a part of the frame of the organic small molecule or within and a part of the chain, backbone or side chain of the organic monomeric group, oligomer or polymer. Both pendant amines and nitrogens within and a part of the frame or chain, backbone or side chain are also included by Formula IV.

The linear, branched, cage, cyclic, dendritic, star and/or fullerene organic moieties carrying the moieties X and Y representing Formulas I and II may be organic small molecules, organic monomeric groups, organic oligomers or organic polymers and are designated in Formulas III and IV as $R^5$. For Formula III, X is bonded to the organic moiety at least twice and preferably at least three times. The position of X in an organic moiety as a small molecule may be attachment to a single carbon atom or to different carbon atoms or a combination thereof of the small molecule frame. The position of X in an organic moiety as a monomeric group, oligomer or polymer is attachment to different carbon atoms, attachment to the same carbon atom or to a combination thereof, of the chain, backbone or side chain. The attachment to different carbon atoms for the monomeric group, oligomer or polymer is preferred.

For Formulas III and IV, each of the designators a and b independently is an integer of at least 2, preferably at least 3 and indicates the number of X and Y groups present per total organic compound. For small molecules, monomer group, oligomer or polymer, the X and Y groups may be arranged as described above. For example, for the saturated organic group, the number of X and Y groups per total molecule designated by a and b independently and respectively may be at least 2, preferably at least 3, more preferably at least 4 up to about 10 per total organic compound. For the arylalkyl or aryl or heteroaryl group, each of a and b independently is at least 2 preferably at least 3 up to 10 per aromatic organic group. For the monomer group, oligomer or polymer, each of a and b independently is at least 2 and preferably at least 3 per monomeric group, oligomer or polymer.

The designator r relates to Formula IV, the amine containing organic compound. This designator provides two alternatives for the arrangement of the amine group relative to the organic moiety. The amine group may be pendant to the frame, chain, backbone or side chain of the organic moiety or it may be a part of the frame, chain, backbone or side chain. When the amine is part of the frame, chain, backbone or side chain, it is sometimes described herein as a nitrogen as set forth above, in this configuration, the nitrogen remains an amine group as understood chemically. The designator r is an integer of 1 when multiple Y groups are bonded to a single $R^5$ group. Thus, there is one organic moiety to which multiple amine groups are bonded pendantly. In the other alternative, the designator r is an integer greater than 1 when a single Y group (nitrogen) is bonded to multiple $R^5$ groups and the multiple $R^5$ groups constitute a single organic moiety. In this alternative, multiple nitrogens can be contained within the frame, chain, backbone or side chain of the small molecule, monomer group, oligomer or polymer. In addition, nitrogens as part of the frame, chain, backbone or side chain as well as amine groups pendant to the frame, chain, backbone or side chain may be present. An example is branched polyethylene imine.

A small molecule under the designation $R^5$ may be a saturated aliphatic organic group. The saturated organic group may be a linear or branched alkyl group of 1 to 24 carbons optionally with one or more heteroatoms in the alkyl chain or a cyclic or bicyclic alkyl or alkyl-cycloalkyl group of 3 to 20 carbons optionally with one or more heteroatoms in the cycloalkyl ring or alkyl chain or both. The heteroatoms may be one or more oxygen, nitrogen or sulfur. Examples of the alkyl group include those listed above as examples of $R^1$ and $R^{4a}$. Included also as examples would be cyclic and bicyclic alkyl groups such as cyclohexyl, bicyclohexyl, butyl cyclohexyl and similar groups.

A small molecule under the designation $R^5$ may also be an aromatic group such as an arylalkyl, aryl or heteroaryl group. The arylalkyl or aryl group may be a benzyl, phenylethyl, phenylpropyl, phenyl, biphenyl or naphthyl group, or a heteroaryl group of 6 to 10 carbons and one or more heteroatoms selected from oxygen, nitrogen and sulfur. The heteroaryl group is described in the Definitions section above. The saturated aliphatic organic group is preferred over the aromatic group.

A preferred organic moiety $R^5$ as a small molecule includes an embodiment which is a linear or branched alkyl group of 1 to 24 carbons optionally with one or more heteroatoms in the alkyl chain. An additional embodiment is a cyclic or bicyclic alkyl or alkyl-cycloalkyl group of 3 to 20 carbons optionally with one or more heteroatoms in the cycloalkyl ring or alkyl chain or both. The preferred weight average molecular weight of the first, or second compound resulting from such a preferred $R^5$ small molecule is from about 200 to about 2000 Da.

An additional preferred $R^5$ as a small molecule includes an embodiment such as an arylalkyl or aryl group comprising a benzyl, phenylethyl, phenylpropyl, phenyl, biphenyl or naphthyl group, or a heteroaryl group of 6 to 10 carbons and one or more heteroatoms selected from oxygen, nitrogen and sulfur. The preferred weight average molecular weight of the first or second compound resulting from such a preferred $R^5$ small molecule is from about 500 to about 3000 Da.

A monomer group, oligomer or polymer under the designation $R^5$ may be a monomer group, oligomer or polymer of repeating monomeric units. The monomer group may be a monomer, dimer, trimer, tetramer, pentamer, hexamer, heptamer, octamer, nonamer or decamer. The oligomer may be repeating monomeric units of 10 to 20 units. The polymer may be repeating monomeric units of at least 20 units, preferably from about 20 to about a million units, preferably about 20 to 20,000 units, more preferably from about 20 to about 10,000 units, most preferably from about 20 to about 5000 units. These number of units roughly provide a weight average molecular weight of at least about 2 KDa, preferably from 2 KDa to about 20 million KDa, more preferably about 2 KDa to about 5 million KDa, most preferably from about 2 KDa to about 2 million KDa.

Exemplary monomeric units include to one or more olefin monomers, ester units of diacids/diol monomers, ester units of hydroxy acid monomers, ether monomeric units, thioether monomeric units, polyol monomeric units, alkylene oxide monomeric units, alkylene imine monomeric units, urethane monomeric units, urea monomeric units, amide units of diacid/diamine monomers, amide units of amino acid monomeric units.

A preferred monomer group, oligomer or polymer embodiment includes one in which the monomeric unit is a mono-olefin of from 2 to 6 carbons and optionally at least some and preferable most and especially preferably all of the olefinic monomer units are substituted by alkyl of 1 to 6 carbons, mono or di alkoxycarbonyl of 2 to 6 carbons, amido, phenyl, and/or phenyl substituted by C1-C3 alkyl, a C2 to C4 carboxyl alkyl ester or carboxamide. The preferred weight average molecular weight of the first or second compound resulting from such a preferred $R^5$ organic moiety is from about 2 kDa to about 200 kDa.

A preferred monomer group, oligomer or polymer embodiment includes one in which the monomeric unit is a urethane or thiourethane monomeric unit of a combination of a linear, branched or cyclic alkyl diisocyanate of 2 to 6 carbons and an alkyl diol or alkyl dithiol of 2 to 6 carbons. The preferred weight average molecular weight of the first or second compound resulting from such a preferred $R^5$ organic moiety is from about 2 kDa to about 200 kDa.

A preferred monomer group, oligomer or polymer embodiment includes one in which the monomer unit comprises an ester or thioester monomeric unit of a hydroxyalkanoic acid or thiolalkanoic acid of 2 to 6 carbons, or a combination of an alkyl diol or alkyl dithiol of 2 to 6 carbons and a dialkanoic acid of 2 to 6 carbons. The preferred weight average molecular weight of the first or second compound resulting from such a preferred $R^5$ organic moiety is from about 2 kDa to about 200 kDa.

An especially preferred monomeric unit includes the foregoing olefin or ester unit. A more especially preferred monomeric unit includes the foregoing olefin.

Exemplary Organic Monomer Group, Oligomer or Polymer

The repeating monomeric unit comprising the monomer group, oligomer or polymers can be conceptualized as classes, subclasses and categories of organic polymers without the functional groups X and Y. Such monomer groups, oligomers or polymers include the above described monomeric units. These monomer groups, oligomers or polymers include but are not limited to oligomers and polymers of appropriate monomeric units such as but not limited to one or more olefin monomers, ester units of diacids/diol monomers or of hydroxy acid monomers, ether monomeric units, thioether monomeric units, polyol monomeric units, alkylene oxide monomeric units, alkylene imine monomeric units, urethane monomeric units urea monomeric units, amide units of diacid/diamine monomers or of amino acid monomeric units; hydroxylated polyester, acrylate functionalized polyester, polyester polyurethane acrylic copolymer, polyurethane-polyglycol copolymer, polycarbonate diols, styrene-allyl alcohol copolymer, as well as other repeating residues based on carbon or carbon in combination with other atoms such as oxygen and/or nitrogen, and any combination thereof. Additional monomer groups, oligomers or polymers include but are not limited to non-polar olefinic polymers, polar, non-protonic olefinic polymers, vinyl polymers, polyethers, polycondensates, block polymers and any compound with repeating carbon unit residues. Preferably the monomer groups, oligomers or polymers are polyolefins including polyvinyl compounds, polyesters, polyethers, polyurethanes or polyamides or any combination thereof. More preferably, the organic monomeric groups, oligomers or polymers are polyolefins including polyvinyl compounds, polyesters or polyurethanes or any combination thereof. Especially more preferably, the organic monomeric groups, oligomers or polymers are polyolefins, polyvinyl compounds or polyesters.

The monomer groups, oligomers or polymers containing acid groups may be developed from any monomeric unit containing acid groups such as carboxylic acid, sulfonic acid, sulfinic acid, phosphoric acid. The acidic units may be combined with non acidic units which are hydrophilic or hydrophobic to provide appropriate monomer group, oligomer or polymers. Such monomer groups, oligomers or polymers are described in the following passages. In these passages, the terms "polymer, copolymer and terpolymer" exemplify the monomer group, the oligomer as well as the polymer.

Monomer group, oligomer or polymers may include copolymers of preferably at least one linear, branched or cyclic (cycloaliphatic or aromatic) (moth)acrylic acid ester monomer and/or of at least one linear, branched or cyclic (cycloaliphatic or aromatic) mono- or disubstituted (meth) acrylic acid amide monomer.

Included are monomer groups, oligomers or polymers such as ethyl acrylate/N-tert-butylacrylamide terpolymers, tert-butyl (meth)acrylate and/or isobutyl (meth)acrylate/C1-C4 alkyl (meth)acrylate copolymers such as a tort-butyl acrylate/ethyl acrylate terpolymer, ethyl acrylate/methyl methacrylate terpolymers and tetrapolymers such as the ethyl acrylate/methyl methacrylate copolymer; methyl methacrylate-butyl or ethyl acrylate/hydroxyethyl or 2-hydroxypropyl acrylate or methacrylate tetrapolymers such as the methyl methacrylate/butyl acrylate/hydroxyethyl methacrylate tetrapolymers.

Additional examples of monomer groups, oligomers or polymers include copolymers of acrylic acid and of C1-C4 alkyl methacrylate and terpolymers of vinylpyrrolidone, of C1-C20 alkyl, for example lauryl, methacrylate. Yet other examples of monomer groups, oligomers or polymers include amphoteric copolymers such as N-octylacrylamide/methyl methacrylate/hydroxypropyl methacrylate/tert-butylaminoethyl methacrylate copolymers.

Additional examples of monomer groups, oligomers or polymers include copolymers of (meth)acrylic acid esters or amides furthermore containing linear, branched or cyclic (cycloaliphatic or aromatic, which may or may not be substituted) vinyl esters, such as vinyl acetate; vinyl propionate; vinyl esters of branched acid such as vinyl versatate; vinyl esters of substituted or unsubstituted benzoic acid; these copolymers may furthermore also contain groups resulting from the copolymerization with styrene, alpha-methylstyrene or a substituted styrene. These copolymers may also contain olefinic groups resulting from the copolymerization with styrene. α-methylstyrene, a substituted styrene and optionally monoethylenic monomers such as ethylene.

Exemplary monomer groups, oligomers or polymers also include copolymers of crotonic ester containing vinyl acetate or propionate units in their chain and optionally of other monomers such as allylic or methallylic esters, vinyl ethers or vinyl esters of a saturated, linear or branched carboxylic acid containing a long hydrocarbon chain, such as those containing at least 5 carbon atoms, it being possible for these polymers optionally to be grafted and crosslinked, or alternatively a vinyl, allylic or methallylic ester of an alpha- or beta-cyclic carboxylic acid. These copolymers may also contain olefinic groups resulting from the copolymerization with styrene, α-methylstyrene, a substituted styrene and optionally monoethylenic monomers such as ethylene.

Additional examples of the monomer groups, oligomers or polymers include vinyl polymers such as vinyl acetate/crotonic ester/polyethylene glycol copolymers, vinyl acetate/crotonic ester. Additional examples of monomer group, oligomer or polymers include the polyolefins, polyvinyls, polyesters, polyurethanes, polyethers, polycondensates and natural polymers.

Additional monomer groups, oligomers or polymers include but are not limited to homopolymers and copolymers of olefins; cycloolefins; butadiene; isoprene; styrene; vinyl ethers, esters, or amides; (meth)acrylic acid esters or amides containing a linear, branched, or cyclic C1-C24 alkyl group, a C6-C24 aryl group or a C2-C24 hydroxyalkyl group. These polymers may be obtained from monomers such as isooctyl(meth)acrylate, isononyl(meth)acrylate, 2-ethylhexyl(meth)acrylate, lauryl(meth)acrylate, isopentyl (meth)acrylate, n-butyl(meth)acrylate, isobutyl(meth)acrylate, ethyl(meth)acrylate, methyl(meth)acrylate, tert-butyl (meth)acrylate, tridecyl(meth)acrylate, stearyl(meth) acrylate, hydroxyethyl(meth)acrylate, 2-hydroxypropyl (meth)acrylate, benzyl acrylate, phenyl acrylate, and mixtures thereof. Amides monomers include but are not limited to (meth)acrylamides, such as N-alkyl(meth)acrylamides, for example of a C2-C12 alkyl, such as N-ethylacrylamide, N-t-butylacrylamide, and N-octylacrylamide; N-di(C1-C4)alkyl (meth)acrylamides and perfluoroalkyl (meth)acrylates.

The monomer groups, oligomers or polymers may also include embodiments based upon attachment of a vinyl group to a diverse number of compounds. Polymerization delivers the polyvinyl compound (e.g., a version of polyolefins) with a large variation of substituent identity. Examples of vinyl monomers for such polymerization include but are not limited to vinyl alkanoate such as vinyl acetate, N-vinylpyrrolidone, vinylcaprolactam, vinyl N—(C1-C6)alkylpyrroles, vinyloxazoles, vinylthiazoles, vinylpyrimidines, vinyl pyridine, vinyl thiophene, and vinylimidazoles, olefins such as ethylene, propylene, butenes, isoprene, and butadienes.

The monomer groups, oligomers or polymers as block copolymers are also included, examples of which include but are not limited to a block copolymer comprising at least one block comprising styrene units or styrene derivatives (for example methylstyrene, chlorostyrene, or chloromethylstyrene). The copolymer comprising at least one styrene block may also comprise, for example, an alkylstyrene (AS) block, an ethylene/butylene (EB) block, an ethylene/propylene (EP) block, a butadiene (B) block, an isoprene (I) block, an acrylate (A) block, or a methacrylate (MA) block, or a combination of these blocks. The copolymer comprising at least one block of styrene units or styrene derivatives may be a diblock or triblock copolymer, for example of the polystyrene/polyisoprene or polystyrene/polybutadiene type, those of the polystyrene/copoly(ethylene-propylene) type or alternatively of the polystyrene/copoly(ethylene/butylene) type as well as styrene-methacrylate copolymers.

Further non-limiting examples of the monomer groups, oligomers or polymers include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, vinyl dimethylpropionate/vinyl laurate, vinyl acetate/octadecyl vinyl ether, vinyl acetate/allyl stearate, vinyl acetate/1-octadecene and allyl propionate/allyl stearate.

Additional monomer groups, oligomers or polymers include polyalkenes and copolymers of C2-C20 alkenes, for example polybutene, polymers of natural origin, which are optionally modified, chosen from shellac resin, sandarac gum, dammar resins, elemi gums, copal resins, and polysaccharides comprising alkyl (ether or ester) side chains, for example alkylcelluloses containing a linear or branched, saturated, or unsaturated C1-C8 alkyl radical, such as ethylcellulose and propylcellulose.

The monomer groups, oligomers or polymers also include but are not limited to polycondensates which include but are not limited to polyurethanes, polyurethane-acrylics, polyurethane-polyvinylpyrrolidones, polyester-polyurethanes, polyether-polyurethanes, polyureas, polyurea-polyurethanes, and mixtures thereof. The precursor polyurethanes may be, for example, a copolymer of aliphatic, cycloaliphatic, or aromatic polyurethane, or of polyurea-polyurethane.

The polyurethanes may also be obtained from branched or unbranched polyesters or from alkyds comprising mobile hydrogens that are modified via a polyaddition with a diisocyanate and an organic difunctional (for example dihydro, diamino or hydroxy-amino) coreagent.

Non-limiting examples of the monomer groups, oligomers or polymers may also include polyesters, polyester amides, fatty-chain polyesters, polyamides, and epoxyester resins. The polyesters may be obtained in a known manner via the polycondensation of aliphatic or aromatic diacids with aliphatic or aromatic diols or with polyols. Succinic acid, glutaric acid, adipic acid, pimelic acid, suberic acid, or sebacic acid may be used as aliphatic diacids. Terephthalic acid or isophthalic acid, or even a derivative such as phthalic anhydride, may be used as aromatic diacids. Ethylene glycol, propylene glycol, diethylene glycol, neopentyl glycol, cyclohexanedimethanol, and 4,4-N-(1-methylpropylidene) bisphenol may be used as aliphatic diols.

The First and Second Silicone Compounds, Formulas V, VI

The first and second silicone compounds range from monomer groups to oligomers and polymers. This range-covers molecular weights to weight average molecular weights from low, on the order of a few hundred Da to very high, on the order of MDa. There is no small molecule version of the silicone compounds. As a monomer group, oligomers and/or polymers, the silicone compounds may be repeating monomeric units of the configuration MDTQ wherein M is a monofunctional trialkylsiloxane unit of the formula $Alk_3SiO_{1/2}$, D is a difunctional dialkylsiloxane unit of the formula $Alk_2SiO_{2/2}$, T is a trifunctional monoalkylsiloxane unit of the formula $AlkSiO_{3/2}$ and Q is a tetrafunctional siloxane unit of the formula $SiO_{4/2}$. The symbol Alk is alkyl of 1 to 6 carbons and is preferably methyl (Me) and functional in the context of MDTQ silicone defines the number of Si—O—Si connections among the units of MDTQ.

The weight average molecular weight of the silicones as small molecules, monomer group, oligomer or polymer follows the monomeric unit ranges set forth in the Summary. The monomeric units are the MDTQ siloxane units described above. The small molecule ranges from one siloxane unit to as many as four units. The monomer group ranges from one or two units to ten MDTQ units. The oligomer ranges from 10 to 20 MDTQ units. The polymer is at least 20 MDTQ units, preferably from 20 to one million MDTQ units, more preferably 20 to 20,000 MDTQ units. The weight average molecular weights of the silicone classes include the weight of the functional groups and ranges from about 1000 Da to as much as 10 million Da.

As silicone compounds, the first and second compounds may be linear, branched dendritic, star and/or fullerene-like silicone compounds of Formulas V and VI:

  Formula V:

  Formula VI:

For Formulas V and VI, X is Formula I, V is Formula II, and each $R^6$ independently is a linear, branched or dendritic silicone moiety comprising an MDTQ siloxane compound of one to four siloxane units, or an MDTQ silicone oligomer or polymer. For the silicone compounds there is no incorporation of nitrogen into the backbone, chain or side chain of the silicone compound as a monomer group, oligomer or polymer.

The silicone compounds optionally have one or more up to a maximum of 20 hydroxyl and/or alkoxy groups bonded to silicon atoms.

Formula V has at least its M units and/or its D units of the silicone moiety bonded to X groups (i.e., at least two X groups bonded to different M and/or D units) or alternatively has at least two D and/or T units bonded to different X groups. In these configurations, X replaces alkyl of said M, D and T units. The distribution of X groups for Formula V is preferably random as discussed above.

Formula VI has at least two Y groups bonded to M units of the silicone moiety (i.e., at least two V groups are bonded to two different M units) or at least two Y units bonded to M units and also to one or more D and T units, or at least two Y units bonded to D units. In these configurations, Y replaces alkyl of said M, D and T units. The distribution of Y groups for Formula VI preferably may be random as discussed above For Formulas V and VI, each of the designators c and d independently is an integer of at least 2, preferably at least 3 in total per MDTQ siloxane monomer group and in total for the MDTQ silicone oligomer or polymer.

The first and second compounds may be organic and silicone combinations of foregoing Formulas III and V as the first compound and Formulas IV and VI as the second compound. In other words, a first combination may be Formula III and Formula VI. A second combination may be Formula V and Formula IV. In addition, Formulas III and V may be combined as graft or block copolymers to form a first compound and Formulas IV and VI may be combined as graft or block copolymers to form a second compound. Junctions between the organic segments and silicone segments can be prepared by hydrosilation or by carbanion addition to a chlorosilyl group.

Polymeric Formulas for First and Second Compounds

A description of the organic and/or silicone first and second compounds as monomer group, oligomer and polymer can be set out as multi-monomeric unit Formula VII for the first compound and Formula VIII for the second compound.

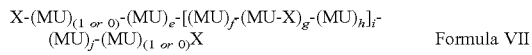

Formula VII

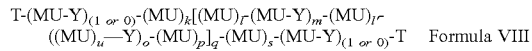

Formula VIII

For Formulas VII and VIII, MU is an organic or a silicone repeating monomeric unit and Formulas VII and VIII provide a pair of linear, branched, dendritic, star and/or fullerene organic polymers; a pair of linear, branched or dendritic silicone polymers; a combination of a linear, branched, dendritic, star or fullerene organic polymer and a linear, branched or dendritic silicone polymer; or a combination of linear, branched, dendritic, star or fullerene organic/silicone block copolymers; or any combination thereof. The configurations of Formulas VII and VIII as organic compounds other than linear can be prepared through use of trifunctional monomeric units in combination with usual monomeric units. For example, a diene in combination with a monoolefin; a triol or triamine in combination with a diol or diamine; a triacid in combination with a diacid according to the synthetic procedures described above. Additionally, the cage, cyclic, dendritic and branched organic oligomers and polymers may be prepared by prior cross linking of starting materials to yield the precursors for the first and second compounds. The cross linking may be accomplished by free radical initiation, by use of trifunctional cross linkers and by cross link combination of pendant carboxylic acid groups, amine groups, alcohol groups, thiol groups, ester groups, activated ester groups with complementary cross linking reactants including but not limited to diacids, diamines, diols, diisocyanates, carbodiimides, and similar cross linking moieties as are described, for example in "Advanced Organic Chemistry" J. March, $4^{th}$ Ed., cited above. The functional groups may be added to the precursors by known techniques and as described herein. Similarly, configurations of Formulas VII and VIII as silicone compounds other than linear can be prepared through use of T and Q units of the MDTQ siloxane formula. Preferably, the organic or silicone compounds of Formulas VII and VIII have linear or branched configurations, more preferably linear.

For Formulas VII and VIII, X is Formula I (the reactive functional group bearing an olefinoyloxy group) and Y is Formula II (the reactive functional group bearing amine and nitrogen group). T is selected from hydrogen, methyl, methoxy, ethoxy or hydroxy and is a terminal unit compatible with the organic polymer or with the silicone polymer or with a block copolymer. The distribution of X groups for Formula VII and Y groups for formula VIII preferably is random as discussed above. Thus, MU units may be positioned on either side of MU units bearing X groups or Y groups according to Formulas VII and VIII.

The small letters e though s provided in Formulas VII and VIII are integer designators and establish the average numbers of various monomeric units possible for these Formulas. These designators individually have the following values:

1) each of e and k independently is an integer of 1 to 100.
2) each of f and l and l' independently is an integer of 1 to 100.
3) g is zero or 1.
4) each of m and o independently is zero or 1, provided that when MU is a silicone repeating monomer unit, o is zero so that Formula VIII as a silicone compound will not contain nitrogen in the silicone backbone.
5) n is 2 or 3.
6) each of h and p independently is an integer of 1 to 100.
7) each of i and q independently is an integer of 1 to 10,000.
8) each of j and s independently is an integer of 1 to 100.

Further explanation of the provisions for Formula VII and the integers provides that for $(MU-X)_g$ with g as one indicates that the X group may be pendantly bonded to the organic or silicone backbone or with g as zero indicates that pendant X groups are absent so that resulting Formula VII only has terminal X groups. The monomeric units $(MU-X)_{(1\ or\ 0)}$ indicate that Formula VII may have terminal X groups or may have no terminal X groups. These variations provide a Formula VII with terminal X groups only, pendant X groups only or terminal and pendant X groups.

For Formula VIII, $(MU)_n—Y)_o$ with designator o as 1 indicates a Y group in the organic backbone chain such that Y is bonded to two (n=2) or to three (n=3) MU units. When MU is a silicone unit, the designator o is zero. The silicone Formula VIII does not contain nitrogen atoms within the silicone backbone. MU-Y indicates a Y group pendantly bonded to the organic or silicone backbone chain. $(MU-Y)_{(1\ or\ 0)}$ indicates that Formula VIII may have terminal Y groups or may have no terminal Y groups. These variations provide a Formula VIII with pendant Y groups only, with terminal Y groups only or with pendant and terminal Y groups.

Finally, the universal provision regarding functional groups applies to the minimum number of X's and Y's present in Formulas VII and VIII. This provision means that Formula VII has at least two X groups and Formula VIII has at least two Y groups.

A preferred embodiment of Formula VII has designator integers g as 1, the sum of f and h as 5 to 1000 and i as 1 to 100 and has an average number of MU units between a terminal MU-X group and a pendant MU-X group closest to the terminal MU-X group and between closest pendant MU-X groups in the range of about 2 to about 1000, preferably 5 to 200, more preferably 5 to 100, most preferably 5 to 50.

Another preferred embodiment of Formula VII designator g is zero and the average number of MU units between the terminal MJ-X groups is in the range of about 2 to about 1000, preferably about 5 to about 500, more preferably about 5 to about 300, most preferably about 5 to about 50.

A preferred embodiment of Formula VIII has designators m as 1, o as zero, the sum of l, l' and p as 20 to 1000, q as 2 to 10,000, preferably 4 to 1000, more preferably about 4 to 500 and $(MU-Y)_{(1\ or\ 0)}$ as zero or 1 so that the average number of MU units between closest pendant MU-Y groups when, $(MU-Y)_{(1\ or\ 0)}$ is zero, and between closest pendant MU-Y groups and between terminal MU-Y and closest pendant MU-Y groups when $(MU-Y)_{(1\ or\ 0)}$ is 1 is in the range of about 2 to about 1000, preferably about 5 to about 500, more preferably about 5 to about 250, most preferably about 5 to about 100.

Another preferred embodiment of Formula VIII has designators m as 1, o as 1, the sum of 1 and p as 20 to 1000, l' as 20 to 100, n as 2, q as 2 to 10,000, preferably 4 to 1000, more preferably about 4 to 500 and $(MU-Y)_{(1\ or\ 0)}$ as zero or 1 so that the average number of MU units between closest pendant MU-Y groups when $(MU-Y)_{(1\ or\ 0)}$ is zero, and between closest pendant MU-Y groups and between terminal MU-Y and closest pendant MU-Y groups when (MU- $Y_{(1 \text{ or } 0)}$ is 1 at least 2 or preferably in the range of about 2 to about 1000, preferably about 2 to about 500, more preferably about 2 to about 250, most preferably about 2 to about 50; the average number of MU units between closest MU-Y-MU groups is in the range of at least 2, preferably about 2 to about 100, preferably about 2 to about 50, more preferably about 2 to about 8 and the average number of MU units between closest MU-Y and MU-Y-MU units is at least 2, preferably in the range of about 2 to about 100, preferably about 2 to about 50, more preferably about 2 to about 10. More preferably for this embodiment, designator q is at least 4, preferably at least 5 up to about 100,000.

An additional preferred embodiment of Formula VII provide that g and i of Formula VII are respectively at least 1 and at least 2.

An additional preferred embodiment of Formula VIII provides that MU-Y$_{(1 \text{ or } 0)}$ is 1, designators k and s are one, l and p are one, n is 2 and 3, o is one and q is 100 to 10,000 and MU is an organic repeating monomeric unit. (eg, PEI)

For the organic compound embodiment of Formulas VII and VIII, the monomeric units for the monomer group, oligomer and polymer may be the same monomeric units described above as organic monomeric units for Formulas III and IV. Similarly, for the silicone compound embodiments of Formulas VII and VIII, the monomeric units may be the same MDTQ units described above for Formulas V and VI.

Another Version of Preferred Embodiments of Formula VIII

Another version of preferred embodiments of Formula VIII may be based upon an organic compound when Formula VII is either an organic oligomer or polymer or is a silicone oligomer or polymer. Preferred embodiments of Formula VIII as an organic compound include but are not limited to linear polyethyleneimine (linear PEI), branched polyethyleneimine (branched PEI), linear and branched polypropylene imine, polyallylamine hydrochloride (PAH), polydiallyldimethylammonium chloride (PDADMAC), copolymers thereof and mixtures thereof. Examples of preferred embodiments of Formula VIII may be linear and/or branched polyethyleneimine, copolymers thereof and mixtures thereof. Copolymers of the foregoing preferred embodiments may be random or block copolymers. Additional examples of the preferred embodiments of formula VIII include examples indicated by entries a-e below wherein e covers copolymers of any combination of a-d.

a) First is a linear polyethyleneimine of the formula:

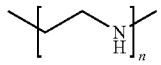

in which n is an integer representing the degree of polymerization, wherein n ranges from 50 to 20,000, preferably from 100 to 3,500.

b) Second is a branched polyethyleneimine consisting of primary, secondary and tertiary amine groups, for example but not limited to those depicted by the conceptual illustration:

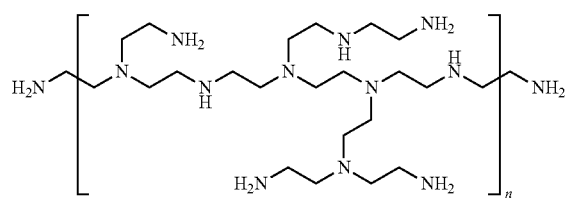

in which n is an integer representing the degree of polymerization, wherein n ranges from 5 to 4,000, preferably from 10 to 4,000, more preferably from 50 to 1,000, most preferably from 50 to 500. The branched polyethyleneimine may have significantly longer branches than are shown by the illustration.

c) Third is a polyallylamine hydrochloride (PAH) of the formula:

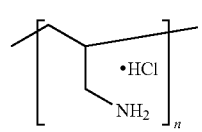

in which n is an integer representing the degree of polymerization, wherein n ranges from 50 to 20,000, alternatively from 150 to 2000, alternatively from 150 to 800.

d) Fourth is a polydiallyldimethylammonium chloride (PDADMAC) of the formula:

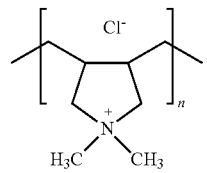

in which n is an integer representing the degree of polymerization, wherein n ranges from 50 to 20,000, alternatively from 150 to 4,000.

c) Fifth is copolymers and mixtures of the foregoing compounds a-d.

Additional preferred embodiments of Formula VIII when Formula VII is a silicone compound include polyamino silicones in which the amine groups are pendant organic amine groups bonded directly to the silicon atoms of the silicone backbone, in both of these configurations, the foregoing embodiments of Formula VIII are similar to or the same as the compounds of the third component discussed below. When the composition is formulated with the third component, the compounds of the second and third components may be the same, one may be organic based, and the other silicone based and in all instances these compounds are polymers bearing pendant organic amine groups.

G Factor Analysis

When the first and second compounds with complementary functional groups are applied to the keratin material such as hair, they will undergo an in situ covalent linking reaction leading to the formation of new covalent bonds. According to the multicomponent process of the invention, application to the substrate material and especially the hair of the multicomponent composition results in the formation of a solid, flexible coating having a network, dendritic and/or star three dimensional configuration. When present, the colored pigment particles are embedded in the coating. The new in situ formed bonds can change the rheological characteristics of the compounds. Whilst not wishing to be bound to any particular theory, it believed to be advantageous if the compound components change from having a substantial G" component, the so called loss modulus, and a negligible G' component, the so called storage modulus, prior to application to the hair, to the reverse situation where there is negligible G" component and a substantial G' component. This can also be considered by consider the phase angle φ, where $$\varphi = \arctan\left(\frac{G''}{G'}\right)$$

When the complex shear modulus changing from more the 45 degrees to less than 45 degrees. Both the phase angle of the resulting film or coating, and the complex shear modulus can be optimized for performance. Alternatively, it may be possible to quantify the resulting coating properties in terms of Young's Modulus and elongation at breaking.

An AR2000 rheometer from TA instruments was used with a 2.5 cm stainless steel plate. A mixture of the first and second compounds was prepared directly, without a medium or other additives and loaded into the rheometer. The geometry gap was set at 1000 microns, and the temperature equilibrated at 25 C for 10 second. Then over 60 minutes the rheometer performed a time sweep using a 0.1% strain between 0.1 and 10 Hz on a log scale with two points per decade. Subsequently the temperature was increased to 90 C and equilibrated for 2 min before being held at this temperature for a further 60 min. The temperature was reduced to 25 C, and equilibrated for 2 min. A stress sweep was then performed between 0.1 and 10,000 Pa using a log scale with live points per decade. A step termination feature was used when the strain exceeded 10%.

Figure 17:
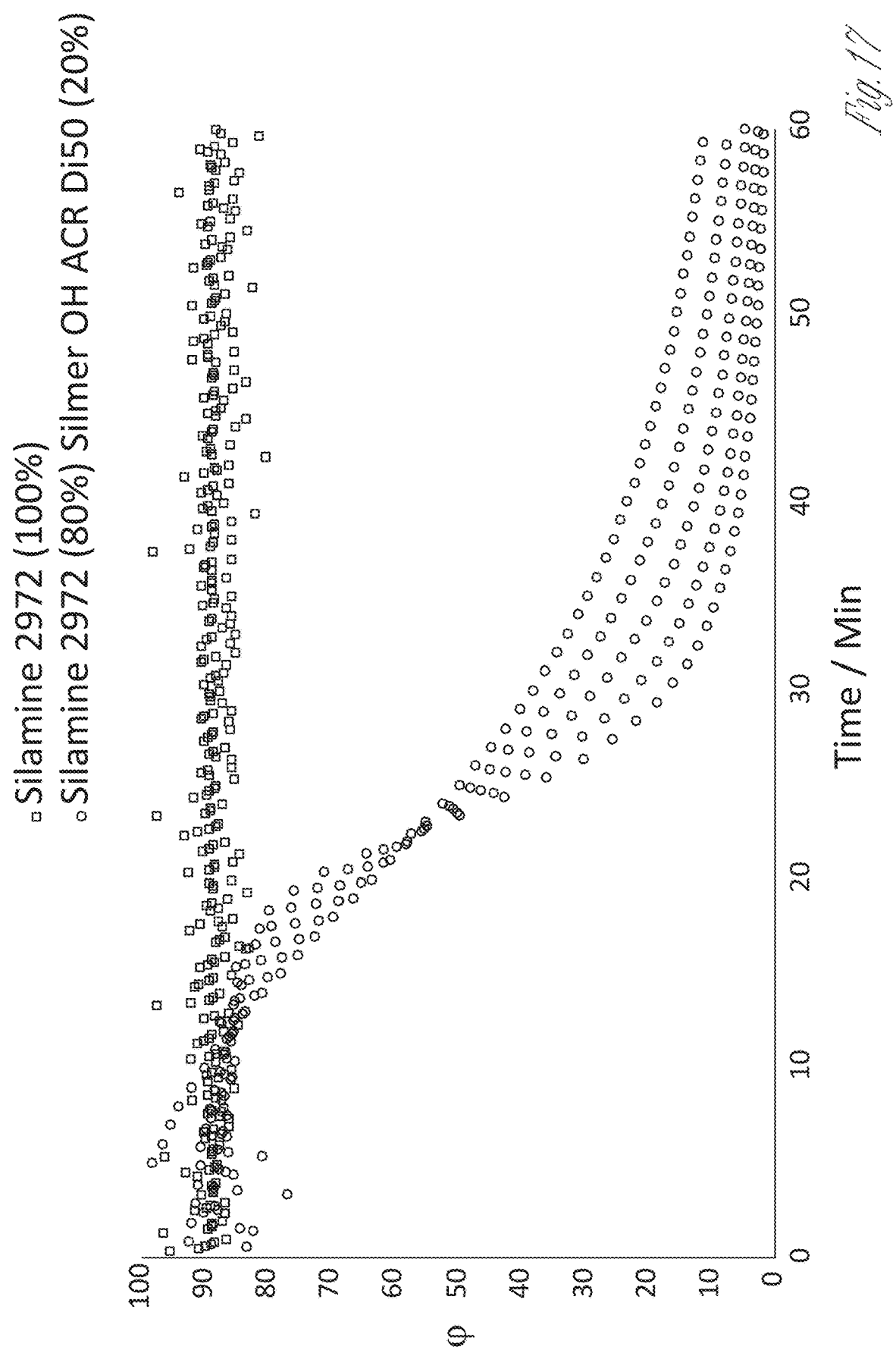
FIG. 17. A plot of the phase angle φ versus time of a multicomponent system versus and single component system.
Figure 18:
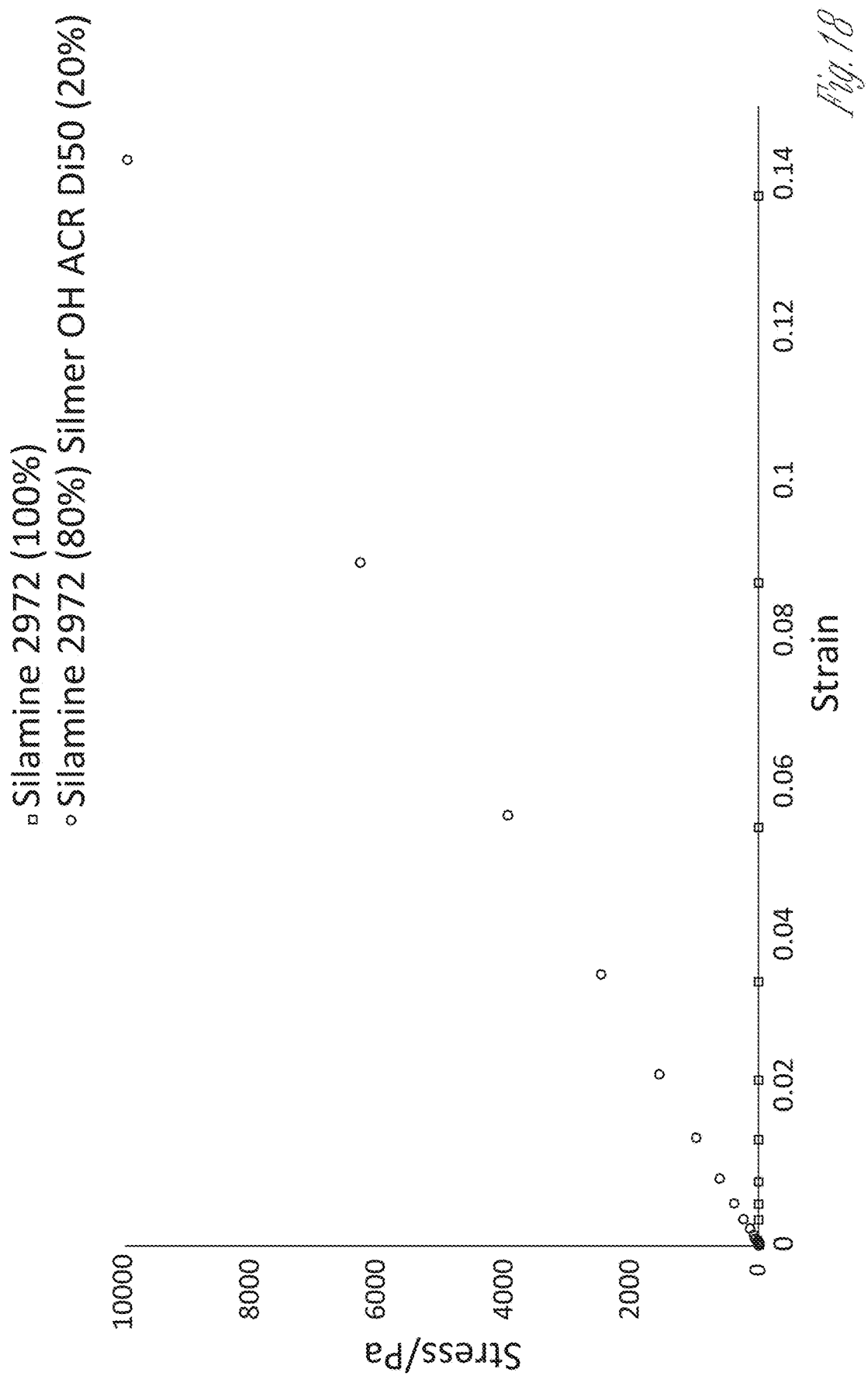
FIG. 18. Young's modulus plot of multicomponent system and a single component system.

FIGS. 17 and 18 illustrate the properties of the starting materials and the in situ cross linked material as silicone polymers. FIG. 17 shows how the viscoselastic properties of the mixed composition changes from liquid to elastomer over about a 25 minute span. There is a time when the different frequencies φ overlap, and this is used to assess the gelation point of the system. This preferably occurs between 2 and 60 minutes, more preferable between 4 and 45 minutes, even more preferably between 5 and 30 minutes. In contrast the top band shows the Silamine 2972 fluid alone remains "fluid like" with a high φ which constant while when combined with the unsaturated carboxyl ester Silmer OH ACR Di50, the composition changes from fluid to elastomeric with a lower φ value. FIG. 18 shows the difference between the stress-strain quotient for the Silamine 2972 alone versus the combination of the Silamine 2972 and the unsaturated carboxyl ester Silmer OH ACR Di50 combination. The Silamine 2972 has a negligible Young's modulus, less than 0.1 MPa, whereas the combined system with Silamine OH ACR Di50 has a value of 70 MPa. The Young's Modulus of the mixed system is preferable between 5 MPa and 1000 MPa, more preferably between 15 MPa and 800 MPa even more preferably between 25 MPa and 500 MPa.

The average length between new in situ connections can be described as the average in situ link length for a given polymer and is the average distance between successive monomeric units carrying Formulas I and II (which are OZ of the following mathematical formula) of a molecule, expressed in terms of $Si(R)_2O_{2/2}$ or D units:

$$\text{Cross link length} = \frac{100}{\sum_{n=1}^{n=n} MPC(OZ)_n}$$

for a series of n potential OZ groups (Formulas I and II) within a given polymer and the term MPC is defined as Mole Percent, which is equal to the number of modifications of the given species per 100 Si groups within the silicone material.

The cross linking role for a given species is given by:

$$\text{Cross link role} = \frac{\sum_{n=1}^{n=n} N_n MPC_n DP}{200}$$

For a series of n potential reactive monomeric units (OZ. Formulas I and II) within a given polymer where N is the number of OZ groups for the given functional group that can form cross links with other functional groups, MPC is the mole percent of the given group within the polymer and DP is the number average degree of polymerization of the polymer. When present, compounds which do not have any OZ functionality have a cross link role=0, they will not form any new molecular connections. When the cross link role=1, the first and second compounds only perform the role of chain extension when used by themselves, although those skilled in the art would understand that such chain extension would not necessarily have to occur through terminal ends of the polymer chain. When the cross link role >1 the first and second compounds can perform network building, the higher this number the greater the impact of the network building. The properties of the resulting film or coating will depend on a complex relationship of the in situ link length and the in situ link role and dilution roles of all of the constituents of the composition including but not limited to the first and second compounds used.

Where more than one functional and nonfunctional compound is used the following factors need to be considered. For each compound added, the reduced fraction of the given compound needs to be calculated.

$$\text{Reduced Fraction} = \frac{\frac{\text{Mass Fraction silicone component}}{DP}}{\int_{n=1}^{n=n} \frac{\text{Mass Fraction silicone compoent}_n}{DP_n}}$$

Where the mass fraction of silicone component is the percent of the non-volatile silicone phase. A volatile silicone is one with a boiling point less than 225 C. If present, silicones which do not have an OZ (Formulas I and II) functionality are also included within the calculation to determine the reduced fraction of the total silicone phase. The DP is the number average degree of polymerization, i.e. the number of Si atoms within the polymer. This effectively factors the number of each type of compound added by the number of individual polymer entities versus just using the weight of the amount of silicone species added. Thus, the effect of a low DP material, e.g. with a DP=10 can produce a larger effect versus the same addition of a higher DP material, e.g. with a DP of 10,000. When added at equal weights, there are 100 times more of the low DP polymer entities versus the high DP polymer chains.

For the mixed system the following terms can be calculated.

Average cross link length=$\sum_{n=1}^{n=n}$Cross linked length$_n$×Reduced Fraction$_n$ For n compound materials within the formulation.

Average cross link role=$\sum_{n=1}^{n=n}$Cross linked role$_n$×Reduced Fraction$_n$ For n compound materials within the formulation.

Using these terms for the silicone phase, non-limiting material combinations which are preferred, include those where the average cross link length is greater than 5, more preferably greater than 10, even more preferably greater than 15, and where the average cross link role is greater than 1.3, more preferably greater than 1.5, even more preferably greater than 1.6. Preferably the average cross link length is less than 400, more preferably less than 350, even more preferably less than 250, and where the average cross link role is less than 6, more preferably less than 4.5, even more preferably less than 4.

The Third Component

The third component is a base compound with third functional groups. The base compound may be a small molecule, a dimer, trimer, tetramer, pentamer, hexamer, oligomer, small or large polymer having pendant and/or terminal third functional groups which may be amine groups. In combination with the first and second functional groups, it is believed that the third functional groups meld together with the first and second functional groups to form a coating having a network, dendritic and/or star arrangement that is interconnected throughout the first and second compounds and the base compound as well as interconnected with the keratin material. Embodiments of the third component combine with embodiments of the first and second components of the multicomponent composition to meld together (e.g., covalently bond as well as entangle large chains together, blend, combine and unite together as one) these components into a coating on keratin material that displays significant remanence. Embodiments of the substantive feature of the third component are the base compound. Embodiments of the base compound incorporate amine groups into and onto an organic or silicone core or chain.

The base compound preferably has a weight average molecular weight of about 150 Da to about 1 MDa. When the base compound is a polymer, its $M_n$ is preferably about 400 Da to about 500 KDa, more preferably about 400 Da to about 250 KDa, most preferably about 2 KDa to about 100 KDa.

Preferred embodiments of the base compound as an organic core with amine groups may be one or more polymer(s). The amine polymer(s) may comprise one or more amino functional group(s) per polymer chain, wherein the amino functional group(s) are selected from the group consisting of primary, secondary, tertiary amino functional groups and mixtures thereof. A working embodiment of the organic core amine is a polyolefin of two to twenty carbons in which the unsaturated bond of the monomer is converted into an aziridine moiety (three member ring with nitrogen). Polymerization combines aziridine rings to form a poly imine with pendant alkyl chains of the residual alkyls of the olefin and pendant imine chains formed by double addition of an aziridine nitrogen to two other aziridine rings.

Embodiments of the base compound may be selected from the group consisting of polyethyleneimine, polyallylamine hydrochloride, polydiallyldimethylammonium chloride, polyvinylamine, aminopolysaccharides, aminopolysilicones, copolymers thereof and mixtures thereof. The amine polymer(s) may preferably be selected from the group consisting of polyethyleneimine, polydiallyldimethylammonium chloride, copolymers thereof and mixtures thereof. Additional embodiments of the base compound include tri and tetra mercapto branched, dendritic, star or fullerene-like alkyl compounds wherein the mercapto groups are the termini and the branches are C3-C10 methylenyl groups on a C3-C10 polymethylenyl backbone.

These embodiments of the base compound may be linear or branched, dendritic, star or fullerene-like and/or may be random or block copolymers.

As amino polymer(s) such as the embodiments of the base compound described above, exemplary selections include:
a) Linear polyethyleneimine of the formula:

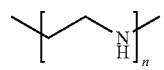

in which n is an integer representing the degree of polymerization, wherein n ranges from 50 to 20,000, alternatively from 100 to 3,500;
b) Branched, dendritic, star or fullerene-like polyethyleneimine consisting of primary, secondary and tertiary amine groups illustrated by the conceptual structure:

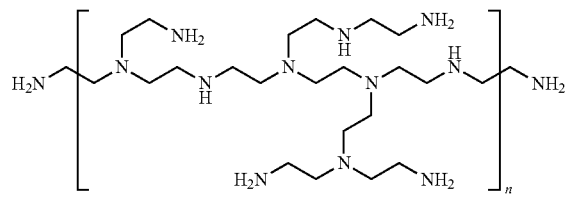

in which n is an integer representing the degree of polymerization, wherein n ranges from 5 to 4,000, alternatively from 50 to 500 and wherein the branch amine groups may be significantly longer than the illustration;
c) Polyallylamine hydrochloride of the formula:

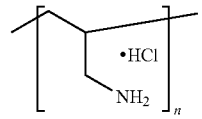

in which n is an integer representing the degree of polymerization, wherein n ranges from 50 to 20,000, alternatively from 150 to 2000;
d) Polydiallyldimethylammonium chloride of the formula:

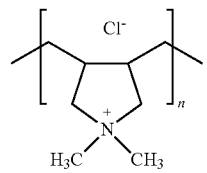

in which n is an integer representing the degree of polymerization, wherein n ranges from 10 to 20,000, alternatively from 150 to 4,000;

copolymers thereof and mixtures thereof.

Embodiments of the base compound may also be amino silicone compounds. Embodiments of the amino compound base compound may comprise any compound chain that incorporates amine functional groups into the compound. The amino silicone compounds may also be aminosiloxane compounds or oligomers and aminosilane small molecule (monomeric) compounds such as
$Me_3Si$—O—$SiMe_2$-O—$SiMe_2NH_2$ and $(CH_3O)_3Si(CH_2)_3NH_2$, $(CH_3CH_2O)_3Si(CH_2)NH_2$, $(CH_3O)_3Si(CH_2)_3NH(CH_2)_2NH_2$, $(CH_3CH_2O)_3Si(CH_2)_3NH(CH_2)_2NH_2$, $(CH_3CH(CH_3)CH_2O)_3Si(CH_2)_3NH(CH_2)_2NH_2$, $((CH_3)_2CHO)_3Si(CH_2)_3NH(CH_2)_2NH_2$, $(CH_3CH_2O)_3Si(CH_2)_4NH(CH_2)_2NH_2$, $(CH_3CH(CH_3)CH_2O)_3Si(CH_2)_4NH(CH_2)_2NH_2$, $((CH_3)_2CHO)_3Si(CH_2)_4NH(CH_2)NH_2$, $(CH_3O)_3Si(CH_2)_4NH(CH_2)_2NH_2$ A preferred amino silicone base compound is one having amine functional groups (hereinafter an amino compound) and is based upon siloxane units of the MDTQ configuration described above wherein the organic substituent of the siloxane unit is an alkyl group, preferably a methyl group as described above. The molar ratio of siloxane monomeric units with at least one pendant organic amine group (hereinafter SiA moieties) to siloxane monomeric units having silicon bonded to a substituent selected from the group consisting of alkyl (C1 to C6) or phenyl (hereinafter SiC moieties) is in the range of from about 1:1000 to 1:10 (ratio of SiA units to SiC units), preferably 1:1000 to 1:25, more preferably 1:600 to 1:35, most preferably 1:400 to 1:35 or 1:300 to 1:40. An SiA moiety may contain more than one amine group in which case it counts as just one SiA moiety. An SiC moiety may contain any number of other pendant groups as long as a primary, secondary, tertiary or quaternary amine group is not present. The amino compound may have a weight average molecular weight ranged from about 5 KDa to about 150 KDa, preferably about 6 KDa to about 130 KDa, more preferably about 8 KDa to about 120 KDa.

The amine functional groups of the amino compound may be primary, secondary, tertiary amine groups or quaternary ammonium groups or any combination thereof. The secondary, tertiary or quaternary amine groups may be substituted by alkyl groups of 1 to 6 carbons, such as methyl, ethyl, propyl, butyl, pentyl or hexyl or any combination thereof. The amine functional groups may be organic pendant groups wherein the amine group terminates the end of the organic group. The pendant organic amine group is bonded to the silicone backbone by a carbon to silicon bond between the organic group and a siloxane monomeric unit as —O—Si(R')$_2$—O— wherein each R' is independently selected from a pendant organic amine group and an alkyl group of 1 to 6 carbons and at least one R' group is a pendant organic amine group. The organic amine group may be a linear alkyl group of 1 to 16 carbons or a branched, dendritic, star or fullerene-like or cyclic alkyl group of 3 to 16 carbons. The alkyl group may contain one or more heteroatoms and/or hetero-groups in the chain including such groups as —NH—, —O—, —S—, —CONH— or —NHCO—, —SO$_2$NH— or —NHSO$_2$—, Typical pendant amine groups include such arrangements as:

$(CH_2)_3$—NH—$(CH_2)_3NH_2$, —$CH_2$—$CH(CH_3)$—$CH_2$—NH—$(CH_2)_3NH_2$
$(CH_2)_3$—CONH—$(CH_2)NH_2$, —$(CH_2)_3$—NHCO—$(CH_2)_3NH_2$ and single amine groups such as —$(CH_2)_n$—$NH_2$ wherein n is 1 to 6, preferably 1 or 4 or branched, dendritic, star or fullerene-like chain versions thereof such as —$CH_2$—$CH(CH_3)$—$CH_2$—$NH_2$.

The amine group or groups may be pendant to the silicone chain at uniform or random locations along and within the silicone chain. The amine functional group may also terminate the ends of the silicone chain but an aminosilicone polymer having terminal amine groups preferably will also have pendant amine groups along the silicone chain.

The Fourth Component

The fourth optional component is an agent that catalyzes or retards the in situ covalent reaction of the complementary reactive pair. The agent may also be a chemical enhancer or retarder for changing the activation energy of the in situ reaction. The fourth component is optional and typically is added when the complementary reactive pair typically does not covalently react under normal environmental conditions at a speed which is desired. For example, the enhancement or retardation of the reaction rate may be influenced by base (e.g., tertiary amine or aromatic amine such as quinoline) or by alkali catalysis or through addition of a solvent that promotes or retards the proximity requirement for the reaction between the complementary functional groups.

Glass Transition Temperature

All of the first and second compound embodiments for the first and second components are viscous liquids and/or gels at ambient temperature and pressure and have a glass transition temperature (Tg) at very low temperatures such as about −30° C. to about −150° C. or −200° C. for silicones and Tg's of −30° to 0° C. for organics. Because the Tg's of the compound components are low to very low, the starting material Tg's will not play a role in the hardness, stiffness, flexibility and softness of the linked multicomponent composition as a coating on the substrate material.

In general, the glass transition temperature or $T_g$ determines the solid-solid transition of a material such as a polymer from a hard glassy material to a soft rubbery material. If the $T_g$ of the material is too high, and the material is a solid, it will be stiff and inflexible at normal temperatures. For coatings with the compounds and base compound this would be an undesirable result. The coating should be soft, flexible and unnoticeable to touch and sight yet should not flake, break-up or otherwise release from the keratin fiber, and especially from human hair, when stroked by a hand or brushed with a brush. Because the Tg of the compounds is so low, coatings prepared from them will usually exhibit the desirable qualities described above. However, if the in situ linked connections of the first and second compounds and the base compound produces a silicone network coating or with the organic polymer produces an organic-silicone network that does not exhibit the foregoing desirable qualities, a plasticizer can be added to lower the Tg of this linked silicone network.

Exemplary Embodiments

Exemplary embodiments of the first and second compounds which are organic oligomers and polymers incorporates olefinic monomeric units as $R^5$. Included are oligomers and polymers of alkyl (meth)acrylate, alkyl crotonate, alkene of 2 to 6 carbons, alkyl cinnamate dialkyl itaconate, dialkyl maleate, dialkyl fumarate and styrene. The alkylating group of these esters may be an alkyl of 1 to 3 carbons. Copolymers of these monomeric units may include methyl (meth)acrylate copolymerized with dimethyl maleate and styrene. Additional copolymers may include methyl crotonate copolymerized with dimethyl maleate and styrene. Homopolymers may include the polymerization product of methyl (meth)acrylate or of methyl crotonate.

Additional exemplary embodiments of organic first and second compounds as oligomers and polymers may be polyurethanes, polyesters and polyamides. The exemplary urethanes may be made by combination of 1,6 hexane diol and bis isocyanato cyclohexyl) methane. Exemplary polyesters may be made by combination of adipic acid and 1,6 hexane diol. Exemplary polyamides may be made by combination of adipic acid and 1,6 hexane diamine.

In these examples, the functional groups may be combined with a modified starting material to produce a polymerization reactant bearing an attachment link for the functional group or the functional group itself. For example, instead of a mono alcohol as the esterifying group, a monoprotected diol such as 1,4-butandiol can be added to (meth)acrylic acid. Following polymerization, the protected pendant alcohol can be deprotected and then esterified with the olefin carboxylic acid such as acrylic acid to form the X group. Similarly, an amino alcohol such as hydroxy butyl amine can have the amine group protected and applied as the esterifying alcohol for (meth)acrylic acid. Following polymerization, the protected amine may be deprotected to produce the Y group.

For polyurethanes, polyesters and polyamides, a portion of the diol or diamine can be modified to have a protected third group that will become a link for the functional groups X and Y. For example, a triol having a protected third hydroxyl can serve as such a link. Following polymerization as a polyurethane or polyester, the diol moiety having the protected third group, e.g., protected hydroxyl, can be deprotected and linked with the olefin carboxylic acid as described above. Similarly, a diol also bearing a protected amine group can serve as a reactant to deliver the amine functional group. For polyamides a portion of the diamine reactant can be a monoprotected triamine or a diamine with a protected hydroxyl group. Following polymerization, the protecting group may be removed, and the resulting hydroxyl can serve as a link or the resulting amine can serve as an amine functional group.

An exemplary embodiment of a silicone first and second compound is based upon the silicone/siloxane formula MDTQ. The silicone of Formula VII (first compound) is linear with one or two optional branches. The termini bear M groups and at least two terminal M groups are modified with X groups. The weight average molecular weight of this first silicone compound is in a range of about 0.5 KDa to about 50 KDa. The second silicone compound is also linear, has no branches and has at least 24 D groups modified with Y groups. The weight average molecular weight of the second silicone compound is in a range of about 0.5 KDa to about 100 KDa.

A further exemplary embodiment of a multicomponent composition based upon silicone first and second compounds may be depicted as a first silicone polymer with pendant acryloxy groups and a second silicone polymer with pendant amine groups. A third component based on an amine base compound, polyamine is exemplified as a polyethylene imine. While the examples can be reframed to depict any of compound variations described above, an illustration is provided of the first and second compounds with first compound organosiloxane monomeric units bearing acryloxy groups as the functional group X and a second compound with a second reactive organosiloxane monomeric units bearing amine as the second functional group Y. In addition, a third component, polyethylenimine can be added.

These exemplary embodiments may have dispositions of X and Y groups to provide all combinations across the organic and silicone first and second compounds. As first and second compounds, the X and Y groups may be arranged to provide
  a) Terminal X and Terminal Y groups;
  b) Pendant X and Terminal Y groups;
  c) Terminal X and Pendant Y groups;
  d) Pendant X and Pendant Y groups;
  c) Terminal and Pendant X groups and Terminal Y groups;
  f) Terminal and Pendant X groups and Pendant Y groups;
  g) Terminal X groups and Terminal and Pendant Y groups;
  h) Pendant X groups and Terminal and Pendant Y groups; and
  i) Terminal and Pendant X groups and Terminal and Pendant Y groups.

The first compound bearing olefinoyloxy groups (X) of a preferred embodiment is exemplified by a silicone acrylate, for example Silmer OH ACR Di10. Silmer OH ACR DiA 15, Silmer OH ACR Di25, Silmer OH ACR Di50 from Siltech shown below as an MD silicone having pendant and or terminal olefinoyloxy groups. Silicones of this linear MD and a branched MDT construction have the olefinoyloxy group of the following formula wherein n is 3.

—(CH$_2$)$_n$OCH$_2$CH(OH)CH$_2$OC(O)C(CH$_3$)=CH$_2$, bonded at least to terminal M groups in which one of the methyls of the M group is replaced by the olefinoyloxy group. Optionally silicones of the MD or MDT construction may also have such olefinoyloxy groups bonded to one or more D groups. In this instance also, one of the methyls of the D group is replaced by the olefinoyloxy group. Optionally, these exemplary olefinoyloxy silicones may have a branch T group to which is bonded a branched chain of D groups ending in an M group in which one of the methyls is replaced by a methoxy or hydroxy group.

The second compound bearing amine groups (Y) is exemplified by the amino silicone, for example Silmer NH Di8, Silmer NH E 47, Silmer NH C50, Silamine 2972, Silamine MUE from Sihech and these examples present the pendant and/or terminal amines or diamines, and alkoxy or silanol terminated or trimethyl silyl cod groups. One example of these amino silicones is shown below.

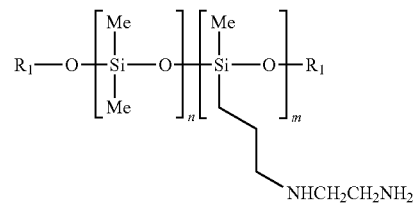

Exemplary second compounds also may be based upon MD silicone chains and MDT silicone chains in which two or more pendant amine groups of the formula

—(CH$_2$)$_3$NH(CH$_2$)$_2$NH$_2$ are bonded to silicons of the M (terminal groups) and D (pendant groups) of the silicone as replacements of the methyl groups of the M and D units.

The third component, the polyamine is exemplified by the polyethylene imine Epomin P-1050.

Such systems can be optimized by selecting the degree of functionality of the acryloxy and amine groups of the two silicones, the concentration of the amines of the polyethylene imine and the relative ratio among these three starting materials.

For Scheme 40 an amino base compound such as polyethyleneimine will produce the same Michael addition product shown for addition of the amino silicone to the acryloxy group.

Another Preferred Embodiment

Another exemplary embodiment of a multicomponent composition may be depicted as first and second components with organic first and second compounds respectively having acryloxy and amine groups and a third component with an amine base compound. While the examples can be

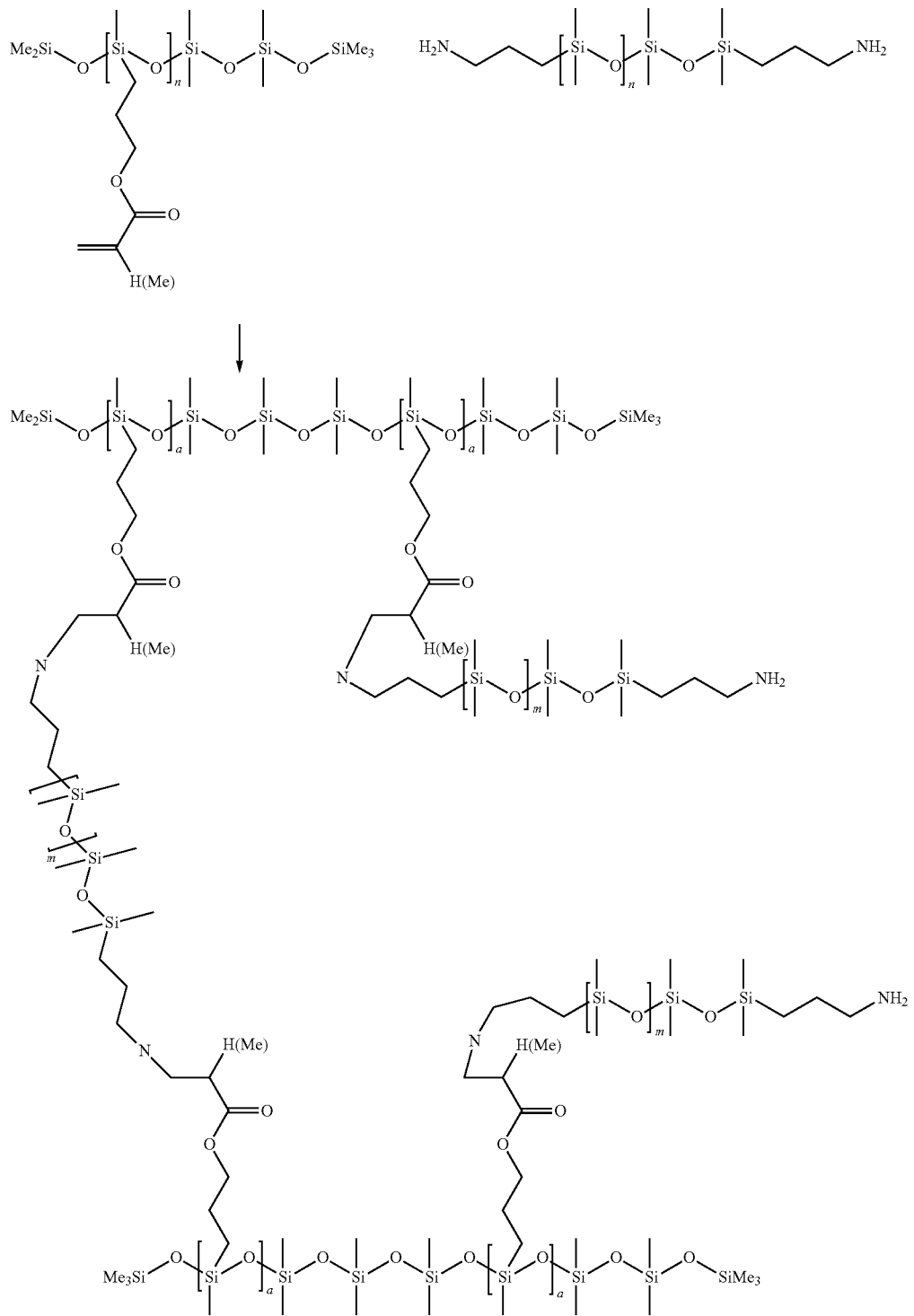

Scheme 40 refrained to depict any of the organic small molecule, monomer group, oligomer or polymer variations described above, an illustration of the first and second organic compound in situ reaction incorporates a first compound with a first reactive small molecule bearing acryloxy groups as the functional group X and a second compound with a second reactive amine monomeric units bearing amine as the second functional group Y. In addition, a third component, polyethyleneimine can be added.

The first compound bearing acryloxy groups (X) of this embodiment is exemplified by a tetraacyloxyalkylenyl alkane wherein $R^1$ is an alkylenyl group of 2 to 6 carbons optionally bearing a hydroxyl group and $R^7$ is an alkane of 1 to 20 carbons, preferably 1 to 10 carbons, more preferably 1 to 6 carbons. When $R^7$ contains more than 1 carbon, the four acryoxy groups are distributed along the alkane chain. The second compound bearing amine groups (Y) is exemplified by polyethylene imine. Such systems can be optimized by selecting the degree of functionality of the acryloxy and amine groups of the two organic compounds including the polyethylene imine and the relative ratio among these two starting materials. For Scheme 50 the polyethylencimine may bind multiple times with a single tetraacryloxy compound and may bind with multiple tetracryloxy compounds.

B. Plasticizer

If the glass transition temperature of the linked polymer network coating is too high for the desired use yet the other properties of the polymer coating are appropriate, such as but not limited to color and wash fastness, one or more plasticizers can be combined with the multicomponent composition embodiments so as to lower the $T_g$ of the components or the linked network coating and provide the appropriate feel and visual properties to the coating. The plasticizer can be incorporated directly in the coloring composition or can be applied to the in situ hair before or after the coloring composition. The plasticizer can be chosen from the plasticizers usually used in the field of application.

The plasticizer or plasticizers can have a molecular mass of less than or equal to 5,000 g/mol, such as less than or equal to 2,000 g/mol, for example less than or equal to 1,000 g/mol, such as less than or equal to 900 g/mol. In at least one embodiment, the plasticizer, for example, has a molecular mass of greater than or equal to 40 g/mol.

Thus, the multicomponent composition can also comprise at least one plasticizer. For example, non-limiting mention can be made, alone or as a mixture, of common plasticizers such as: glycols and derivatives thereof, silicones, silicone polyethers, polyesterpolyols; adipic acid caters (such as diisodecyladipate), trimellitic acid esters, sebacic acid

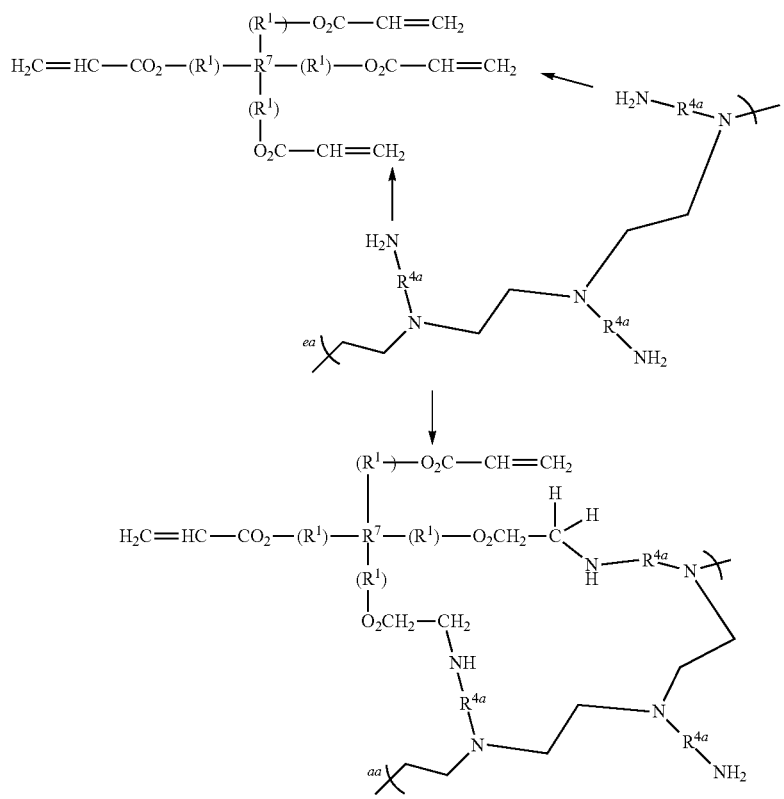

Scheme 50

An especially preferred embodiment of the tetraacryloxy compound of Formula III of Scheme 50 has $R^1$ as an alkylenyl group of 1 to 3 carbons, preferably 2 carbons and $R^7$ as an alkane of 1 or 2 carbons, preferably 1 carbon. When $R^7$ is 1 carbon, all four acryloxy groups (X groups) are bonded to the single carbon, i.e., a methane with four substituents.

esters, azalaeic acid esters; nonlimiting examples of glycol derivatives are diethylene glycol ethyl ether, diethylene glycol methyl ether, diethylene glycol butyl ether or diethylene glycol hexyl ether, ethylene glycol ethyl ether, ethylene glycol butyl ether, or ethylene glycol hexyl ether; polyethylene glycols, polypropylene glycols, polyethylene glycol-polypropylene glycol copolymers, and mixtures thereof, such as high molecular weight polypropylene glycols, for example having a molecular mass ranging from 500 to 15,000, for instance glycol esters; propylene glycol derivatives such as propylene glycol phenyl ether, propylene glycol diacetate, dipropylene glycol ethyl ether, tripropylene glycol methyl ether, diethylene glycol methyl ether, and dipropylene glycol butyl ether. Such compounds are sold by Dow Chemical under the names DOWANOL PPH and DOWANOL DPnB; acid esters.

The plasticizer can be present in the composition of the present disclosure in an amount from about 0.01% to 20%.

Viscosity, Composition Concentrations

The viscosity of the composition functions to hold the composition with pigment microparticles in place on the substrate material while the in situ linked coating is formed. The viscosity substantially avoids free translational Dow of the composition. Free translation flow would cause the composition to rapidly run and drip off the surfaces of the hair strands. Nevertheless, the viscosity is not so high that it will not undergo self-leveling to substantially uniformly coat the substrate material. Appropriate viscosity of the composition is the result of the interaction of the first and second compounds and the base compound, their concentrations, the pigment microparticles, and as appropriate, an optional viscosity control agent, an optional suspending agent and an optional thickening agent. Generally, the viscosity of the composition may range from about 0.1 to about 200 Pa s$^{-1}$ preferably 1 to 100 Pa s$^{-1}$, more preferably 10 to 75 Pa s$^{-1}$. Viscosity measurements are carried out on a controlled stress rheometer eg. Using an AR2000 type manufactured by TA instruments, or equivalent instrument, A 6 cm flat acrylic cross hatched parallel plate geometry (TA item 518600,901) and a stainless steel cross hatched base plate (TA item 570011.001) are used. The rheometer is prepared for flow measurements as per standard manufacturer procedure. The parallel plate geometry gap is set to 1000 microns. The flow procedure is programmed to the rheometer with the following conditions: continuous stress ramp 0.1-300 Pa over 2 minutes at 25° C., including 250 measurement points in linear mode. The product is loaded into the geometry as per standard procedure and the measurement commences at 5 min after the mixture preparation. Shear stress value at 10 sec$^{-1}$ shear rate is obtained from the shear stress vs. shear rate curve, and the corresponding viscosity is calculated by dividing the obtained shear stress by 10.

The concentration of each of the first and second compounds in the multicomponent composition with first, second and third components may range from about 0.25% to about 20%, preferably about 0.5% to about 15%, more preferably about 0.75% to about 10% relative to the total weight of the multicomponent composition. A preferred concentration of the combination of the first and second compounds in the multicomponent composition with first, second and third component ranges from about 0.5% to about 35%, more preferably about 1.0% to about 25% and most preferably about 1.5% to about 15% by weight relative to the total weight of the multicomponent composition.

C. Medium

The medium of the multicomponent composition embodiments of the invention may be water alone, water in mixture with a volatile polar protic or aprotic organic solvent, or a non-aqueous non-polar solvent or a mixture of non-aqueous solvents with polar protic or aprotic non-polar organic solvent, a volatile low $M_w$ silicone solvent or a mixture of such a volatile silicone solvent with a non-polar non-protic organic solvent or a polar, protic organic solvent or mixtures thereof. In general, the medium is any solvent suitable for dispersing the compounds and the base compound of the embodiments of the multicomponent composition described herein. In addition to water present in the medium, a volatile solvent may be present including a volatile polar protic or aprotic organic solvent, or a silicone solvent or mixtures thereof. Volatile organic solvents of which non-limiting mention may be made include: volatile pyrrolidones 1-methylpyrrolidin-2-one, volatile $C_1$-$C_4$ alkanols such as methanol, ethanol or isopropanol; eaters of liquid $C_2C_6$ acids and of volatile $C_1$-$C_8$ alcohols such as methyl acetate, n-butyl acetate, ethyl acetate, propyl acetate, isopentyl acetate, or ethyl 3-ethoxypropionate; ketones that are liquid at room temperature and volatile, such as methyl ethyl ketone, methyl isobutyl ketone, diisobutyl ketone, isophorone, cyclohexanone, or acetone; volatile polyols such as ethylene glycol and propylene glycol. Additional solvents include cyclic silicone solvents such as decamethylcyclopentasiloxane, octamethylcyclotetrasiloxane, dowsil polymethyl siloxanes.

According to at least one embodiment of the present disclosure, the organic solvent is chosen from ethanol, isopropanol, acetone, and isododecane and solvents that have similar properties compared with the ones described herein.

The medium may be present in the composition according to the present disclosure in an amount ranging from about 0.1% to about 99% by weight, such as from about 1% to about 70% by weight, for example ranging from 5% to 90% by weight relative to the total weight of the composition.

D. Pigments

The color composition embodiments of the present invention make it possible to obtain colored and remanent coatings, without substantially altering the keratin material. As used herein, the term "pigment" generally refers to any particle colorant having or containing pigment material that gives hair fibers color including black and white, such as titanium dioxide that give only white to hair fibers. Dyes presented in molecular form, are also referred to herein as pigment microparticles or pigment particles. A dye is an organic compound that absorbs visible light so as to produce a colored reflection or refraction. A dye suitable for use as a pigment is preferably a hydrophobic organic pigment, insoluble in water and is soluble in the corresponding lipophilic organic solvents having a C Log P greater than 2. The dye will have an extinction coefficient greater than 1000 L/mol$^{-1}$ cm$^{-1}$.

Incorporated into the composition, the dye may be dissolved or dispersed in the medium. When deposited with the coating, the dye is a molecular dispersion intercalated within the coating. The terms pigment microparticles and pigment particles are synonymous and are used herein interchangeably. The pigments can be organic, inorganic, or a combination of both. The pigments may be in pure form or coated, for example with a polymer or a dispersant.

Selections, multiple kinds and varying forms of the pigment microparticles as described in the following passages can be incorporated in any of the first, second and third components of the multicomponent composition, or can be incorporated in any two of these components or in all three. Preferably, pigment microparticles can be incorporated in either or both of the first and second components. More preferably, pigment particles can be incorporated in the first component.

The at least one pigment that can be used can be chosen from the organic and/or mineral pigments known in the art, such as those described in Kirk-Othmer's Encyclopedia of Chemical Technology and in Ullmann's Encyclopedia of Industrial Chemistry. The pigments comprised in the microparticles comprising at least one pigment will not substantially diffuse or dissolve into keratin material. Instead, the pigment comprised in the microparticles comprising at least one pigment will substantially remain separate from but attached to the keratin material.

The at least one pigment can be in the form of powder or of pigmentary paste. It can be coated or uncoated. The at least one pigment can be chosen, for example, from mineral pigments, organic pigments, elemental metal and their oxides, and other metal modifications, lakes, pigments with special effects such as nacres or glitter flakes, and mixtures thereof.

Pigment Shape

The pigment microparticles can have any suitable shape, including substantially spherical. But the pigment microparticles can also be oval, elliptical, tubular, irregular, etc., or even combinations of various shapes. In addition, the pigment microparticles can have two dimensions or three dimensions, length and width/diameter and depth, of similar magnitude. In one embodiment with any of the reactive components of the instant invention, the pigments may be surface treated, surface coated or encapsulated.

In addition, the pigment microparticles can have a rather two-dimensional shape, with the smallest dimension substantially smaller than the two other dimensions, in which case the microparticles are referred to as being 2-dimensional microparticles. For example, the thickness of the microparticles can be significantly less than their length and width. The length and width can be of similar magnitude. Examples includes pigment microparticles having a shape of platelets. i.e. with a thickness that is substantially smaller than the planar dimension. For example, with dmax the largest dimension and dmin the smallest dimension the aspect ratio AR=dmax/dmin, of microparticles having a substantially two-dimensional shape, can be from about 10:1 to about 1000:1, preferably from about 10:1 to about 800:1, preferably from about 20:1 to about 800:1, preferably from about 10:1 to about 600:1, preferably from about 20:1 to about 600:1. Typically, the 2D-microparticles have a largest and a smallest dimension in their planer dimension, which both are significantly larger than the smallest dimension of the 2D-microparticles extending perpendicular to the planer dimension.

According to an embodiment, the pigments can include pigment microparticles of different shape. For example, microparticles of different size can be used to provide different reflecting and absorbing properties. Microparticles having different shape can also be formed of different pigment material. Furthermore, microparticles having different shape can also formed of different pigment material to provide different color.

Pigment Size

The pigments can be present in the composition in undissolved form. Depending on the shape, the pigments can have a D50[vol] particle diameter of from 0.001 micron to 1 micron.

For example, pigments that can be described as being microparticles can have a D50[vol] particle diameter of from 0.01 micron to 1 micron, preferably of from 0.015 micron to 0.75 micron, more preferably of from 0.02 micron to 0.50 micron. The microparticles can also have a D50[vol] particle diameter of from 0.06 micron to 0.9 micron, preferably of from 0.08 micron to 0.9 micron, and more preferably between from 0.08 micron to 0.9 micron, such as from 0.08 micron to 0.8 micron, or such as from 0.08 micron to 0.6 micron. According to an embodiment, the microspheres can also have a D50[vol] particle diameter of from 0.1 micron to 1 micron, preferably of from 0.12 micron to 1 micron, and more preferably between of from 0.16 micron to 1 micron, such as of from 0.2 micron to 1 micron, or such as of from 0.08 micron to 0.4 micron. The terms "micron" and "microns" describe the size in micrometers [µm].

In embodiments described herein, the D10[vol] particle diameter can be of from 0.02 micron to 0.3 micron and the D90[vol] can be of from 0.3 micron to 1 micron. In further embodiments, the D 50[vol] particle diameter can be of from 0.06 micron to 0.9 micron and the D90[vol] can be of from 0.4 micron to 1 micron.

The particle diameter is represented by D50 which is the median diameter by volume. D50 is measured with a Malvern Mastersizer 2000, which is a laser diffraction particle sizer and it is measured according to ISO 13320: 2009(en) with Hydro 20000 or Hydro 2000S where the dispersant is water or ethanol. D50 is expressed as x50 in ISO 13320:2009(en).

The term "D50," as used herein refers, to the 50th percentile number- or volume-based median particle diameter, which is the diameter below which 50% by number or volume of the particle population is found.

Laser diffraction measures particle size distributions by measuring the angular variation in intensity of light scattered as a laser beam passes through a dispersed particulate sample analyzer and the particle size is reported as a volume equivalent sphere diameter. A discussion of calculating D50 is provided in Barber et al, Pharmaceutical Development and Technology, 3(2), 153-161 (1998), which is incorporated herein by reference. Pigment microparticles having a D50[vol] particle diameter of less than 20 nm may enter the cuticles and are therefore difficult to remove. Pigment(s) having a D50[vol] particle diameter of more than 1 micron typically do not sufficiently adhere onto hair fibers.

The size of pigment microparticles which can be described to have a 2-dimensional shape, and which are referred to as 2-dimensional microparticles can be determined by SEM. The size of 2-dimensional microparticles can also be determined by laser diffraction measurements. The particle size determined by laser diffraction is a mean size of the different dimensions of the 2-dimensional particles. The apparent DSO[vol] particle diameter of 2-dimensional microparticles, as measured by SEM, can be from 0.5 micron to 50 microns, more preferably from 0.8 micron to 20 microns, more preferably from 1 micron to 15 microns, more preferably from 1.5 micron to 10 microns.

According to an embodiment, pigment particles are referred to as being microspheres can be used light-scattering and/or light absorbing purposes. Those particles, due to their pigment material, impart the hair with a specific color.

According to an embodiment, pigment particles are referred to as being 2-dimensional microparticles can be mainly used for light-reflecting and/or light absorbing purposes. Those particles, due to their pigment material, mainly reflect the light without significantly alter the color of the light.

The pigment microparticles can be light absorbing, but which for wavelengths of visible light provide negligible to low or no scattering. While not wishing to bound by any specific theory, it is believed that such pigments can provide more chromatic colors. Such pigment microparticles can have a D50[vol] value between about 0.001 micron and about 0.15 micron, between about 0.005 micron and about 0.1 micron or between about 0.010 micron and about 0.075 micron.

The pigment microparticles can be predominantly light scattering for wavelengths of visible light and provide low light absorption. While not wishing to bound by any specific theory, it is believed that such pigments can provide the visual effect of lightening the hair. Such pigment microparticles, which can be microspheres, can have a D50[vol] value between about 0.05 micron to about about 1 micron, between 0.08 micron to about 0.9 micron, between about 0.05 micron and about 0.75 micron, between about 0.1 micron and about 0.5 micron or about 0.15 micron and about 0.4 micron. Such materials can have a refractive index above 1.5, above 1.7 or above 2.0.

Pigments made from metal and metal like materials which can conduct electricity, and which can absorb light and re-emit the light out of the metal to give the appearance of strong reflectance. While not wishing to be bound by any specific theory, it is believed that the absorbed light will induce alternating electric currents on the metal surface, and that this currents immediately re-emit light out of the metal. Such pigment microparticles can be platelets, e.g., having a thickness that is substantially smaller than the planar dimension. For example about five, about 10 or even about 400 times smaller in thickness than in the planer. Such platelets can have a planar dimension less than about 30 nm, but with a thickness less than about 10 micron wide. This includes a ratio of 10000 to 30, or 333. Platelets larger in size, such as 50 microns are even available in this thickness of 10 microns, and so the ratios can even go up to 2000.

The pigment microparticles can be a composite formed by two different types of pigment microparticles. Examples include a composite of a 2-dimensional microparticle and at least one micro spherical particle (microsphere), a composite of different micro spherical particles, a composite of different 2-dimensional particles and a core and shell configuration such as but not limited to pigment particles coated with dispersant or other adherent polymeric material.

Pigment microparticles may be materials which are composite comprising a core of pigments made from metal and metal like materials which can conduct electricity, and which can absorb light and re-emit the light out of the metal to give the appearance of strong reflectance. While not wishing t be bound by any specific theory, it is believed that the absorbed light will induce alternating electric currents on the metal surface, and that this currents immediately re-emit light out of the metal. Upon this pigment light absorbing microparticles is immobilized. Such pigment microparticles can be platelets, e.g., having a thickness that is substantially smaller than the planar dimension. For example, five, ten or even 20 times smaller in thickness than in the planer. Such platelets can have a planer dimension less than 15 microns, but with a thickness less than 1 microns, more preferably with a planer dimension less than 12 microns but with a thickness less than 750 nm, even more preferably with a plan dimension less than 10 microns and a thickness less than 0.5 micron. The light absorbing microparticles can have D50 [vol] value between 0.001 micron and 0.15 micron, more preferably between 0.002 micron and 0.1 micron and even more preferable between 0.005 micron and 0.075 micron.

The light absorbing microparticles may also include dyes, pigments, or materials with color centers in the crystal structure, or photonic structures resulting in destructive or constructive interference, diffraction or other structures and materials mentioned in the book "The Physics and Chemistry of Color: the Fifteen Causes of Color", $2^{nd}$ Edition by K. I. Nassau (ISBN 978-0-471-39106-7).

The pigment microparticles can be both light scattering and absorbing for wavelengths of visible light. While not wishing to bound by any specific theory, it is believed that such pigments can provide both some visual effect of lightening the hair. Such pigment microparticles can have a D50[num] value between about 50 nm and about 750 nm, between about 100 nm and about 500 nm or between about 150 nm and about 400 nm. Such materials have a refractive index above about 1.5, above about 1.7 or above about 2.0.

According to an embodiment, different pigment microparticles are combined to provide reflective, transmitting and refractive properties of the hair colored with the color composition described herein. A microparticle combination can be a material composite using at least two different pigment materials to form the pigment microparticles. In addition to, or alternating to, the microparticle combination, a mixture of separate pigment microparticles of different type can be used to bring about the desired reflective, transmitting and refractive properties.

The composite pigments, combination of pigments, and mixtures of pigment microparticles eliminate, or at least significantly reduce, hair penetration and scattering by light and thus eliminate the perception of pigment of natural hair color change.

Pigment Concentration

The color composition for coloring hair fibers according to the present disclosure comprises microparticles comprising at least one pigment. The color composition comprises from about 0.01% to about 40%, about 0.05% to about 35%, about 0.1 to about 25%, or about 0.15% and about 20% pigment(s), by weight of the color composition.

Pigment Material

The material of the pigment microparticles can be inorganic or organic. Inorganic-organic mixed pigments are also possible.

According to an embodiment, inorganic pigment(s) are used. The advantage of inorganic pigment(s) is their excellent resistance to light, weather, and temperature. The inorganic pigment(s) can be of natural origin, and are, for example, derived from material selected from the group consisting of chalk, ochre, umber, green earth, burnt sienna, and graphite. The pigment(s) can preferably be white pigments, such as, for example, titanium dioxide (CI 77891) or zinc oxide. The pigment(s) can also be colored pigments, such as, for example, ultramarine or iron oxide red, luster pigments, metal effect pigments, pearlescent pigments, and fluorescent or phosphorescent pigments. The pigment(s) can be selected from the group consisting of metal oxides, hydroxides and oxide hydrates, mixed phase pigments, sulfur-containing silicates, metal sulfides, complex metal cyanides, metal sulfates, chromates and molybdates, alloys, and the metals themselves.

The pigment(s) can be pearlescent and colored pigment(s), and can preferably be based on mica which are coated with a metal oxide or a metal oxychloride, such as titanium dioxide or bismuth oxychloride, and optionally further color-imparting substances, such as iron oxides, Prussian blue, ultramarine, and carmine. The color exhibited by a pigment can be adjusted by varying the layer thickness. Such pigments are sold, for example, under the trade names Rona®, Coloona®, Dichrona®, RonaFlair®, Ronastar®, Xirona® and Timiron® all of which are available from Merck, Darmstadt, Germany.

The pigment(s) can be organic pigments. The at least one pigment can be an organic pigment. As used herein, the term "organic pigment" means any pigment that satisfies the definition in Ullmann's encyclopedia in the chapter on organic pigments. For instance, the at least one organic pigment can be chosen from nitroso, nitro, azo, xanthene, quinoline, anthraquinone, phthalocyanin, copper phthalocyanin, copper hexadecachlorophthalocyanine, 2-[(2-Methoxy-4-nitrophenyl)azo]-N-(2-methoxyphenyl)-3-oxobutyramide, metal-complex, isoindolinone, isoindoline, quinacridone, perinone, perylene, diketopyrrolopyrrole, thioindigo, dioxazine, triphenylmethane, dimethylquinacridone and quinophthalone compounds, Azo-dyes, Nonionic azo dyes, Anionic Azo dyes, Cationic am dyes, Complex forming azo dye, aza annulene dyes, aza analogue of diarylmethane dyes, aza annulene dyes, Nitro-dyes and their pigments, Carbonyl dyes and their pigments (for example, Anthrachinon dyes, indigo), Sulfur dyes, Florescence dyes, Anthracene or Insoluble alkali or earth metal acid dyes.

Or the pigment can be at least one of uncolored and UV absorbing.

The organic pigment(s) can be selected from the group consisting of natural pigments sepia, gamboge, bone charcoal, Cassel brown, indigo, chlorophyll and other plant pigments.

The pigment(s) used in the color composition can include at least two different pigments selected from the above pigment group, or can include at least three different pigments.

According to an embodiment, the pigment(s) used in the color composition can include at least one yellow pigment selected from the yellow pigment group consisting of a Pigment Yellow 83 (CI 21108), CAS #5567-15-7, Pigment Yellow 155 (C.I. 200310). (CAS: 68516-73-4), Pigment Yellow 180 (C.I. 21290), (CAS: 77804-81-0).

In addition to the at least one yellow pigment, or alternatively, the pigments(s) used in the color composition can include at least one red pigment selected from the red pigment group consisting of: Pigment Red 5 (CI 12490), (CAS #6410-41-9), Pigment Red 112 (CI 12370), (CAS #6535-46-2), Pigment Red 122 (CI 73915), (CAS #980-26-7).

In addition to the at least one yellow pigment and/or the at least one red pigment, or alternatively, the pigments(s) used in the color composition can include at least one green pigment selected from the green pigment group consisting of: Pigment Green 36, (C.I. 74265) (CAS: 14302-13-7).

In addition to the at least one yellow pigment and/or the at least one red pigment and or the at least one green pigment, or alternatively, the pigments(s) used in the color composition can include at least one blue pigment selected from the blue pigment group consisting of: Pigment Blue 16, (CAS: 424827-05-4), Pigment Blue 60 (C.I. 69800), (CAS: 81-77-6), Pigment Blue 66, (C.I. 73000), (CAS: 482-89-3)

In addition to the at least one yellow pigment and/or the at least one red pigment and/or the at least one green pigment, and/or the at least one blue pigment or alternatively, the pigments(s) used in the color composition can include at least one black pigment selected from the black pigment group consisting of: Pigment Black 6 (C.I. 77266). (CAS 1333-86-4), Pigment Black 7 (C.I. 77266), (CAS 1333-86-4).

The pigment(s) can optionally have a surface zeta potential of ≥±15 mV, preferably ≥±20 mV, more preferably ≥±25 mV. The surface zeta potential can be measured with a zetasizer, for example, a Zetasizer 3000 HS, Surface zeta potential measurements are conducted, for example, according to ISO 13099.

Non-limiting examples that can also be mentioned include pigmentary pastes of organic pigments, such as the products sold by the company Hoechst under the names: JAUNE COSMENYL IOG: Pigment Yellow 3 (CI 11710); JAUNE COSMENYL G: Pigment Yellow 1 (CI 11680); ORANGE COSMENYL GR: Pigment Orange 43 (CI 71105); ROUGE COSMENYL R: Pigment Red 4 (CI 12085); CARMINE COSMENYL FB: Pigment Red 5 (CI 12490); VIOLET COSMENYL RL: Pigment Violet 23 (CI 51319); BLEU COSMENYL A2R: Pigment Blue 15.1 (CI 74160); VERT COSMENYL GG: Pigment Green 7 (CI 74260); and NOIR COSMENYL R: Pigment Black 7 (CI 77266).

Inorganic pigments, whether natural or synthetic in origin, include those produced from chalk, red ocher, umbra, green earth, burnt sienna or graphite, for example. Furthermore, it is possible to use black pigments, such as iron oxide black, color pigments such as ultramarine or iron oxide red, and fluorescent or phosphorescent pigments as inorganic color pigments.

Colored metal oxides, metal hydroxides and metal oxide hydrates, mixed phase pigments, sulfurous silicates, silicates, metal sulfides, complex metal cyanides, metal sulfates, metal chromates and/or metal molybdates are particularly suitable. In particular, preferred color pigments are black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), iron blue (ferric ferrocyanide, CI 77510) and/or carmine (cochineal).

The at least one pigment can also be colored pearlescent pigments. These are usually mica-based and can be coated with one or more metal oxides from the group consisting of titanium dioxide (CI 77891), black iron oxide (CI 77499), yellow iron oxide (CI 77492), red and brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Mica forms part of the phyllosilicates, including muscovite, phlogopite, paragonite, biotite, lepidolite, and margarite. To produce the pearlescent pigments in combination with metal oxides, the mica, primarily muscovite or phlogopite, is coated with a metal oxide.

As an alternative to natural mica, it is also optionally possible to use synthetic mica coated with one or more metal oxides as the pearlescent pigment. Such suitable pearlescent pigments based on natural micas are described in, e.g., WO 20051065632. The at least one pigment can also be pearlescent pigments based on natural or synthetic mica and are coated with one or more of the aforementioned metal oxides. The color of the respective pigments can be varied by varying the layer thickness of the metal oxide or metal oxides.

The at least one pigment can also be color pigments commercially available, for example, under the trade names Ariabel® and Unipure® from Sensient, Prestige® from Eckart Cosmetic Colors, and Sunshine® from Sunstar.

Depending on the degree of the change in color that is desired on the keratin fiber, the at least one pigment can also be can be used in varying amounts. The more color pigment that is used, the higher is the extent of the change in color in general. Starting at a certain usage amount, however, the adherence of the pigments to the keratin fiber approaches a limiting value, beyond which it is no longer possible to increase the extent of the change in color by further increasing the pigment amount used. While not wishing to be bound by any specific theory, it is believed that when a certain thickness is achieved, an insignificant amount of the incident lights passes through the pigment layer to make a difference to the observed color due to the hair itself. The rest of the light is either scattered back towards the surface, or absorbed.

The organic pigment can also be a lake. As used herein, the term "lake" means at least one dye adsorbed onto insoluble particles, the assembly thus obtained remaining insoluble during use. The inorganic substrates onto which the dyes are adsorbed can be, for example, alumina, silica, calcium sodium borosilicate, calcium aluminum borosilicate, calcium carbonate, manganese carbonate, aluminum, nitro-dyes, triarylmethin dyes, Azo-dyes, Anthrazen, Acid dyes, polymethine dyes, triarylmethin dyes, aza annulene dyes and polymethine dyes.

The at least one pigment can also be a pigment with special effects. As used herein, the term "pigments with special effects" means pigments that generally create a non-uniform colored appearance (characterized by a certain shade, a certain vivacity, and a certain lightness) that changes as a function of the conditions of observation (light, temperature, observation angles, etc.). They thus contrast with white or colored pigments that afford a standard uniform opaque, semi-transparent, or transparent shade.

Non-limiting mention can also be made of pigments with an interference effect that are not fixed onto a substrate, for instance liquid crystals (MELICONES HC from Wacker) and holographic interference flakes (GEOMETRIC PIGMENTS or SPECTRA F/X from Spectratek). Pigments with special effects also comprise fluorescent pigments, whether these are substances that are fluorescent in daylight or that produce an ultraviolet fluorescence, phosphorescent pigments, photochromic pigments, thermochromic pigments, and quantum dots, sold, for example, by the company Quantum Dots Corporation.

The variety of pigments that can be used in the present disclosure makes it possible to obtain a wide range of colors, and also optical effects such as metallic effects or interference effects.

The pigments that can be used in the present disclosure can transmit light of various wavelengths, including visible light (e.g., light having a wavelength of above 350 nm). The pigment(s) can also transmit light of certain wavelengths, but also reflect light of certain wavelengths. And the pigment(s) can also be 100% reflective. For examples, reflective pigments provide a high specular reflection of visible light. Reflective pigments include those that are partially or completely coated with a non-matt and non-scattering surface layer of a metal or metal oxide. The substrate can be chosen from glasses, ceramics, graphite, metal oxides, aluminas, silicas, silicates, especially aluminosilicates and borosilicates and synthetic mica (e.g., fluorophlogopite), to name a few. The metal or metal oxide can be, without limitation, gold, silver, aluminum, copper, stainless steel, titanium oxides, iron oxides, tin oxide, chromium oxide, barium sulfate, $MgF_2$, $CeF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$ and $MoS_2$, and mixtures thereof. Reflective pigments can have a spectral reflectance in the visible spectrum of at least 70%.

Color Gamut or Pigment Blends

CIEL*a*b* (CIELAB) is a color space specified by the International Commission on Illumination. It describes all the colors visible to the human eye and serves as a device-independent model to be used as a reference.

The three coordinates of CIELAB represent the lightness of the color (L*=0 yields black and L*=100 indicates diffuse white; specular white may be higher), its position between red/magenta and green (a*, negative values indicate green while positive values indicate magenta) and its position between yellow and blue (b*, negative values indicate blue and positive values indicate yellow).

Since the L*a*b* model is a three-dimensional model, it can be represented properly only in a three-dimensional space. Two-dimensional depictions include chromaticity diagrams: sections of the color solid with a fixed lightness.

Because the red-green and yellow-blue opponent channels are computed as differences of lightness transformations of (putative) cone responses, CIELAB is a chromatic value color space.

In the present invention, the color gamut is determined by adding each pigment to be tested in the hair coloring composition, and then individually tested at a level such that when applied to hair, the resulting CIELAB lightness or L* value of the colored hair is 60±2. The level of pigment needed will depend on the pigment being tested. Two hair tresses (Kerling, Natural White special quality) have the multicomponent composition applied as described herein. A Minolta spectrophotometer CM 2600d is used to measure the color of the dried hair tresses, five points on both the front and back sides, and the values averaged. The D65 L*a*b values are calculated. When at least three pigments have each been measured such that their resulting color reside within the target L* values of 60±2 the color gamut can be calculated. First the lengths of each side of the resulting triangle of each combination of three pigments in the a*b plane are computed using the following expressions. To calculate the distance between pigments 1 and pigment 2 the following equation is used:

$$\text{Side Length } SL_{12} = ((a_{pigment\ 1} - a_{pigment\ 2})^2 + (b_{pigment\ 1} - b_{pigment\ 2})^2)^{0.5}.$$

This is computed for each pair of pigments. Then for a series of three pigments.

The resulting color gamut is calculated using the expression:

$$\text{Color Gamut} = (S(S-SL_{12})(S-SL_{13})(S-SL_{23}))^{0.5}.$$

wherein $SL_{12}$, $SL_{13}$, and $SL_{23}$ are the three lengths of the sides of the triangle within the a*b plane, and $S=(SL_{12}+SL_{13}+SL_{23})/2$. Where more than three pigments are used, this calculation can be performed for each combination of the three pigment from the more than three pigments used, and the largest Color Gamut is selected.

The hair coloring composition embodiments of the present invention can also have a color gamut of greater than 250, greater than 500, greater than 750, greater than 800, greater than 900, greater than 1100 or even greater than 1250.

D. The pH

The multicomponent composition embodiments in accordance with the present disclosure can have a pH ranging from about 3 to about 12, preferably about 4 to about 10 and in many embodiments 6.8 or higher. For example, the pH can be 8 or higher, 9 or higher or at most 12. In some examples, the multicomponent composition embodiments in accordance with the present invention can have a pH of from about 7 to about 10, about 5 to about 11 or about 6 to about 8.

The pH may range from about 3 to about 8 for polar functional silicone polymers that can form cationic groups, e.g., amines and ranging from about 5 to about 11 for polar functional silicone polymer that can form anionic groups, e.g., carboxylic and sulfonic acids. For silicone polymer with cation forming groups (amines), preferably the pH is about 4 to about 7 and in many embodiments 6.8 or lower. In some example, the multicomponent composition embodiments with silicone polymers having cation forming groups in accordance with the present invention can have a pH of from about 3.0 to about 8.0, preferably about 3.5 to about 6.8, more preferably about 4,5 to about 6.8, most preferably about 5.5 to about 6.5.

The multicomponent composition in accordance with the present disclosure can comprise a pH modifier and/or buffering agent. The amount is sufficiently effective to adjust the pH of the composition/formulation. Suitable pi modifiers and/or buffering agents for use herein include, but are not limited to, ammonia, alkanolamines such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, such as sodium hydroxide, sodium silicate, sodium meta silicate and ammonium carbonate, and acids such as inorganic and inorganic acids, e.g., phosphoric acid, acetic acid, ascorbic acid, citric acid or tartaric acid, hydrochloric acid, and mixtures thereof.

E. Dispersants

It will be apparent to one skilled in the art that careful and selective choice of dispersant can help to maximize performance in terms of maximizing the amount of color produced from an immobilized film, maximizing the remanence or washfastness, and enabling removal of the color.

For example, in the case where the binder polymer is anionic in nature, dispersants which are anionic or nonionic are preferably chosen, rather than cationic, as this avoids undesired precipitation in the formula prior to it forming a colored film on the keratin—i.e. utilizing the principle of avoiding opposing charges.

Likewise, the principle of choosing chemically similar dispersant and binder (for example, a silicone binder paired with a silicone dispersant, can be followed to ensure maximum compatibility.

As well as compatibility as noted above, the other critical criterion in selecting dispersant(s) is their ability to enable pigment to be dispersed down to the primary particle size, preferably with the minimum amount of input mechanical energy. It will be recognized by someone skilled in the art that the concentration of dispersing agent is also a critical factor. In general, it is usually required that there is a minimum amount for dispersing activity and that below this, the system is either not fully dispersed or, worse, that the dispersant acts as a flocculant.

These two considerations together are used to define preferred materials and their respective concentrations.

It may also be the case, depending on the type of binder polymer used, that the binder or the treatment itself is also a dispersant (see below for discussion of classes of dispersant). In such cases it is possible that no further dispersing additive may be needed.

Overview of Dispersant Kinds, Properties and Chemistry

Dispersants are amphiphilic or amphiphathic meaning that they are chemical compounds possessing both hydrophilic (water-loving, polar) and lipophilic (fat-loving) properties. Dispersants are surface-active materials that allow the homogeneous distribution and stabilization of solids, e.g. pigments in a liquid medium (like a binder), by lowering the interfacial tension between the two components. As a result, agglomerates are broken up into primary particles and protected by a protecting dispersant envelope from re-agglomeration. The dispersants can be subdivided on the basis of the stabilization mechanism into; 1. Dispersants for electrostatic stabilization for example through Anionic dispersing additives (e.g. Polyacrylates and Polyphosphates). Neutral dispersing additives and Cationic dispersing additives and 2. Dispersants for steric stabilization.

Following the foregoing principles and guidelines, the pigment microparticles can be dispersed in the composition with the addition of at least one of a dispersant and a wetting agent. While not wishing to be bound by any specific theory, it is believed that only when the pigments are de-aggregated into their primary particles do they deliver the optimum optical performance. For examples, pigments with a primary particle size of 0.02 micron which provide brilliant bright colors, when present as aggregates of around 0.3 micron provide duller colors.

The dispersant serves to protect the pigment microparticles against agglomeration or flocculation either in the dry state or in the solvent. Dispersants also serve as wetting agents. In this capacity, dispersants as wetting agents can be low or higher molecular weight monomeric surfactants (for example, anionic, cationic or amphoteric surfactants), Dispersants as wetting agents can be higher molecular weight surface-active or pigment particle affinic polymers (for example, polyelectrolyte dispersants such as maleic acid copolymers, and polyurethanes or polyacrylates containing carboxylic acid, amine or isocyanate pigment affinic anchor groups or polyethylene imines) or other type of polyelectrolytes.

G. Incorporation of Pigment in Dispersant

The pigments described herein can be chosen and/or modified to be similar enough such that a single dispersant can be used. In other instances, where the pigments are different, but compatible, two or more different dispersants can be used. Because of the extreme small size of the pigment microparticles and their affinity, combination of the pigment microparticles and dispersant to form a substantially homogeneous dispersion that can subsequently be modified and/or diluted as desired is to be accomplished before combination with any or all of the first, second and third components of the multicomponent composition.

The pigment microparticles can be dispersed and stabilized in the medium by one or more dispersants the properties and kinds of which are described above. Exemplary dispersants include non-ionic surfactants moderate weight hydrocarbons such as isododecane and silicone solvents/dispersants such as cyclopentasiloxane and similar cyclic siloxanes. The dispersant can either be added to the medium, or to a precursor medium or can form a coating on the microparticles to facilitate dispersion. It is also possible to provide the microparticles with a coating of a dispersant material and additionally provide a further dispersant to the medium, or to a precursor medium, which is used to form the final medium.

The dispersant, either added to the medium or provided as coating, facilitates wetting of the microparticles, dispersing of the microparticles in the medium, and stabilizing of the microparticles in the medium.

The wetting includes replacing of materials, such as air, adsorbed on the surface of the pigment microparticles and inside of agglomerates of the microparticles by the medium. Typically, a complete wetting of the individual microparticles is desired to singularize the particles and to break off agglomerates formed by microparticles adhering to each other.

After wetting, the microparticles can be subjected to de-aggregate and de-agglomerate step, generally referred to as dispersing step. The dispersing step typically includes the impact of mechanical forces such as shear to singularize the microparticles. In addition to shearing to singularize, the microparticles can be broken into even smaller microparticles using, for example, roller mills, high speed mixers, and bead mills. Usual practice involves substantially homogeneous dispersion of the pigments in dispersant through the use of high shear mixing; for example through use to the appropriate ball mill, ultra high pressure homogenizer or other system known by those skilled in the art of pigment dispersion.

The dispersant may be added to a dry powder of the pigment particles when the particles are milled to a desired size. During milling, or any other suitable technique to singularize the pigment particles or to break them into smaller part, the dispersant comes in contact with and adheres to the surface of the microparticles. Freshly generated microparticle surface during milling will be coated by the dispersant so that, after milling, the microparticles with a coating formed by the dispersant are provided.

H. Optional Components

Optional components of the composition include suspending agents, leveling agents and viscosity control agents. The suspending agents help maintain the pigment particles in dispersed condition and minimize or negate their agglomeration. Suspending agents include fatty acid esters of polyols such as polyethylene glycol and polypropylene glycol. These are similar to plasticizers and function in similar fashion to allow pigment particles to "slip" by each other without retarding or binding interaction.

The multicomponent composition embodiments in accordance with the present invention can also optionally contain at least one adjuvant, chosen, for example, from reducing agents, fatty substances, softeners, antifoams, moisturizers, UV-screening agents, mineral colloids, peptizers, solubilizers, fragrances, anionic, cationic, nonionic, or amphoteric surfactants, proteins vitamins, propellants, oxyethylenated or non-oxyethylenated waxes, paraffins, $C_{10}$-$C_{30}$ fatty acids such as stearic acid or lauric acid, and $C_{10}$-$C_{30}$ fatty amides such as lauric diethanolamide.

The multicomponent composition embodiments in accordance with the present invention can further optionally contain one or more additives, including, but not limited to, antioxidants, crosslinking agents, reactive diluents, non-reactive diluents, dyes, fillers, plasticizers, processing aids, ultraviolet stabilizers, and combinations thereof.

An additional additive may be a tactile (hair feel) modification agent. These may include, but are not limited to, a softening and/or lubricating and/or anti-static and/or hair alignment and/or anti-frizz benefit and/or impact on the keratin fibres.

I. Content of First and Second Compounds in Composition

Embodiments of the multicomponent composition include solids and liquids. The solids comprise any substance or material of the multicomponent composition that in a form uncombined with any other material, solvent, liquid or substance that has a solid physical form at ambient conditions, Included at least are first and second compounds of the multicomponent composition. Further materials include the optional pigment microparticles and the base compound of the multicomponent composition. The medium is a liquid while the first and second compounds are viscous gel like materials at low average molecular weight and are solids a moderate to high molecular weight. The liquid or gel components as well as the plasticizer, dispersing agent, surface treatment agent, and other materials added to the medium, if any, are included in the solids content as long as they remain with the pigment microparticles following application and setting of the multicomponent composition as a coating on strands of human hair.

Testing the Flexibility of a Coating of the Multicomponent Composition

With the film prepared above, it can also be tested for optical density to check that the polymer film does not itself alter the hair appearance of the hair too significantly.

Further the polymer preferably can have a glass transition point (Tg) as described above so that it is possible to prevent the coating from being damaged or cracked and to secure washing and friction fastness.

The composition coating can have a surface energy between about 20 and about 50 mN m$^{-1}$. The composition coating preferably has high transmission, to ensure that it does not interfere with the optics of the hair coating. The polymer preferably has a refractive index between 1.4 and 1.6.

The film can be assessed by measuring its Shore Hardness. The composition preferably has a shore hardness above 20, more preferably above 40.

Application of First, Second, Third and Optional Fourth Components to Substrate Material The first, second, third components of the multicomponent composition may be maintained in separate storage compartments or in separate kit form when the first, second and third functional groups of these components will react if together. Additionally, the substantive constituent of the fourth component is maintained separately if it will catalyze or otherwise cause reaction of such functional groups. A convenient storage means can be utilized such as plastic squeeze tubes, plastic bottes, glass containers, sachets, multi-compartment containers, spottles syringes and plunger operated dispensing devices. Unit amounts for combination can be formulated so that the entire contents of a unit of the first component can be combined with the entire contents of the second component for application to the substrate material. Alternatively, metered or calibrated dispensing containers for providing measured amounts of the components as directed by printed instructions can be provided. With some embodiments, multiple components can be pre-combined for storage and handling as long as a substantive constituent that would cause in situ linking is maintained in a separate compartment.

Use of the foregoing delivery means enables preparation of an embodiment for practice of the method of the present invention. This embodiment may comprise sequential, simultaneous or premixed application of the first and second components to substrate material. Pigment microparticles may be incorporated in either or both of the first and second components. This aspect of application provides a layer of combined first and second components on the substrate material that will undergo transformation to a coating in which the first and second functional groups of these components in sit interact to covalently bond as the completed coating. Preferably the pairs of first and second functional groups are chemically reactive so that covalent bonds are formed between the first and second compounds and the base compound. As discussed above, depending upon the extent of cross linking, the molecular size of the starting materials and other factors, the resulting coating on substrate material, such as but not limited to keratin material including hair, may be manipulated to enable ready removal by simple shampooing or to enable significant and long lasting remanence against repeated shampooing, rinsing and contact with mild detergents, soap and similar wash substances.

Pretreatment with Third Component

Another embodiment of the method according to the present invention may comprise application of the third component to the substrate material as a pretreatment before application of the first and second components as described above. According to this embodiment of the method, the third component containing the base compound with or without pigment, and preferably without pigment, is applied on or to at least a portion of the substrate material such as hair, and preferably throughout the substrate material. While it is not a limitation of the invention, it is believed that the pretreatment addition of the third component enables enhancement of adhesion between the hair, pigments and first and second components. It is believed that the amine groups of the third component interact with the surface chemical moieties on the substrate material (e.g., hair, nails, skin) and interact chemically with the olefinoyloxy groups of the first compounds and by electrostatic interaction with the groups of the second compound. Although it is not a limitation of the invention, it is further believed that the second functional groups also interact with complementary chemical groups of the substrate material. It is believed that these chemical interactions, which are covalent and also are supplemented by coordinate, electrostatic, ionic, dipolar and/or entanglement interactions function to meld together the substrate material, the pigment microparticles, the first and second compounds and the base compound.

Pretreatment with the third component may be carried out prior to application of the first and second components. Pretreatment may be carried out immediately prior to application of the first and second components, or at least 1 hour prior to application of the first and second components, or at least 24 hours prior to application of the first and second components, or at least 10 days prior to application of the first and second components, or at least one month prior to application of the first and second components. Preferably, pretreatment may be carried out immediately prior to or within a few minutes up to an hour before application of the first and second components. Typically, the third component is at least partially dried with optional heating to at least substantially remove or otherwise eliminate the medium of the third component. For example, excess medium may be removed by contacting with an absorbent fabric or surface or the hair may by heated with a hair drier. Preferably, removal of third component medium is accomplished before application of the first and second components.

Application of First and Second Components Following Pretreatment

As described above, first and second components may be applied to the substrate material in combination with the foregoing pretreatment with the third component or may be applied without such pretreatment. In either arrangement, embodiments of the first and second components are maintained separately when the first and second functional groups constitute reactive pairs as described above. Application of the first and second components to pretreated or un-pretreated substrate material may be accomplished by sequential application of the first and second components or simultaneous application of these components to the hair. Typically for sequential application, either of the first and second components may be applied first, preferably the first component is applied first, especially for embodiments including pretreatment with the third component. Alternatively, the first and second components may be mixed together to form a premix immediately before application to the substrate material. Typically, the rate of reaction of the reactive pairs is pre-adjusted through concentration, steric interaction, temperature, and similar factors controlling reaction rate so that a premix preferably will not substantially interact before the premix is applied to the substrate material. The practice of this step with the pre-treatment embodiment initially introduces combined first and second components on top of the pretreatment layer of base compound on the substrate material. Because the first and second components are in a medium, penetration, combination, mixing and/or melding of the first and second components into the pretreatment layer is believed to be accomplished. The penetration is believed to enable the linking among the first and second compounds, the base compound and the substrate material.

Application of the first and second components to pretreated substrate material is preferably carried out after pretreatment. This sequence may be carried out immediately after pretreatment, or at least 1 hour after pretreatment, or at least 24 hours after pretreatment, or at least 10 days after pretreatment, or at least one month after pretreatment.

The sequential, simultaneous or premix application of the first and second components may be applied to at least a portion of the substrate material or may be applied all over the substrate material. The portions or first and second components may be applied sequentially, simultaneously or as a premix in a single application over all the substrate material or may be applied step-by-step to the substrate material. The first and second components may be applied step-by-step, for example, in case the substrate material is damaged. Applying the first and second components in a step-by-step manner as described above, may help to ensure that the treated portions of the substrate material are saturated with the combined first and second components and may therefore provide a better coverage of the substrate material.

Manipulative Techniques for Application

After the pretreatment of the third component has been accomplished, and the pretreated substrate material optionally rinsed, the pretreated substrate material can be dried. The substrate material can be dried using an elevated temperature. The temperature of the substrate material can be increased to elevated temperatures above room temperature such as 40° C. or higher, for example using a hair drier. While the substrate material is being dried, some form of interdigitated implement can be used to help separate portions of the substrate material, and especially separate hair strands from one another. Examples of interdigitated devices include a comb or a brush. The substrate material can be dried with a hair drier while simultaneously being combed or brushed until it is dry to the touch. Alternatively, other means can be employed to dry and separate the substrate material such as hair simultaneously. For example, using a combination of air movement and vibrations will accomplish distribution of the multicomponent composition throughout the strands of hair.

Operational Method for Coating Hair

The performance of operational method aspects of the present invention can be applied to keratin material to form a coating of the multicomponent composition. This aspect of the invention concerns a method for coating substrate material and comprises applying embodiments of one or more multicomponent compositions for a time sufficient to deposit an effective coating on the substrate material such as each keratin fiber or hair strand. A somewhat to substantially overall distribution of the coating on the length and circumference of each fiber is produced.

To accomplish this aspect, embodiments of the first, second and third components of multicomponent composition are applied to the substrate material according to the sequences described above by brushing, painting, spraying, atomizing, squeezing, printing, rubbing massaging or in some manner coating the substrate material such as hair strands with the embodiments. Following application of a compositional embodiment to the substrate material such as hair strands, the composition is set, cured, linked, coordinated and/or otherwise melded together preferably by warming with blown warm air from a hair dryer or similarly treated to remove the medium, initiate in situ linking of the first and second compounds, the base compound, the substrate material and if present, remove the volatile base. The setting leaves a substantial to essentially complete overall linked coating of the first and second compounds and base compound containing optional dispersed pigment microparticles and optional additional components.

The in situ linking of the substantive constituents of first, second and third components during application provides a linked coating that enables it to resist for a time destruction by washing with dilute mixtures of soap and water or shampoo and water. Coating fastness (remanence) is developed so that washing with dilute aqueous soap solution or dilute aqueous shampoo will not substantially remove the coating, but the coating can be facilely removed by use of a transformation trigger. The properties of the remanent coating include wash-fastness, flexibility, adhesion, abrasion resistance and remanence which are due at least in part to the linked character of the composition constituents including at least the first and second compounds and the base compound and their intermolecular entwining, ionic and electrostatic intermolecular interaction, covalent and/or non-covalent linking, dipole interaction and lipophilic interaction of neutral moieties of these compositional constituents. Because of the ability to control the character of the coating, however, the coating constituents, cross linking and the like can be varied to provide an easily removable coating as well. Such coatings are susceptible to removal by simple shampooing.

Selection of the substantive constituents of the multicomponent composition can be made on the basis of properties such as a solid lattice formation and interaction with the pigment microparticles. Such properties include the flexibility, the hardness, the adhesion, the remanence, the resistance to water or to other chemical compounds, and the abrasion resistance.

The multicomponent compositions in accordance with the present disclosure can have a viscosity that can be controlled to enable the product, to be applied to the hair using either a brush and bowl or a bottle, but with sufficient rheology such that it does not drip and run from the hair onto the face or body. Alternatively, low viscosity formulations may be applied to the hair via a suitable application device such that it does not drip and run form the hair onto the face and body.

The multicomponent compositions can be utilized in concentrated form or in serial dilutions, to provide for a consistent coating results substantially along the entire length of the keratin material.

The aspect of coating mammalian or synthetic keratin material with a multicomponent composition as described above includes a method for this coating. The method comprises:
 (i) applying the above-described multicomponent composition to keratin material comprising an effective coating amount of the first and second compounds, base compound, pigment microparticles and optional additional components;
 (ii) setting the multicomponent composition by removing or otherwise eliminating the medium (e.g., by drying the composition); and.
 (iii) setting the interaction among the first, second and third functional groups of the multicomponent composition by initiating the in situ linking among these groups.

During the setting/drying step, coating distribution can be facilitated by concurrently moving and/or stroking the hair with an interdigitating device. Interdigitating devices include a comb or brush. The interdigitating device needs to be pulled substantially along the hair strands from root to tip. It can be pulled through at a rate of 0.1 cm $s^{-1}$ to 50 cm $s^{-1}$ or at a rate between 0.5 cm $s^{-1}$ to 20 cm $s^{-1}$ The multicomponent composition is applied to the mammalian or synthetic keratin material in any suitable way including spraying the multicomponent composition, massaging the keratin material by hand, after applying the multicomponent composition to the hand or by combing, brushing or otherwise applying the multicomponent composition throughout the mammalian or synthetic keratin material.

Unlike current hair coating approaches that use dyes, the coating with the multicomponent compositions described herein occurs on the surface of the hair strands. Current dye based approaches do provide the head of hair with some coating variation, as the strands are not identical, and some of these differences are preserved after coating. There are also differences root to tip which also helps to provide some variation. Using a pigment based surface coating system such as that of the present invention, the variation of the underlying hair can be substantially removed, leading to a more homogeneous coating result. This coating result can be a more homogenous application of coating. To obtain a somewhat non-homogenous application of coating that tends toward a more natural look, the user can apply the inventive multicomponent composition by any of several techniques.

The methods by which the multicomponent compositions described herein are applied can be modified, such that the user applies the product in one region of the hair, and then can apply a diluted version in another region of the hair. The dilution formula is specially chosen to be compatible with the coating formulation and reduces the coating strength, while maintaining the longevity of the coating result. This can effectively be a "blank" formulation, which contains broadly the same materials as the coating formulation, but with lower or no pigments present. When diluted the ratio of the diluent to coating can be between about 10:1 and about 1:10, about 8:1 and about 1:2 or about 5:1 and about 1:1.

Alternatively, the amount of multicomponent composition applied can be altered in different regions of the hair, for example half the product is applied in the lengths of the hair, leading to a less coating result. The difference in amounts applied in one region of the hair versus another can be between about 4:1 and about 1:4 or about 2:1 and about 1:2.

Alternatively, a combination of this approaches may be used to deliver the target coating variation.

When the foregoing techniques are not possible to be applied, rather than apply a single hair coating, it may be possible to apply two or more hair coatings to different regions of the hair. When this is done, the different in situ hair coatings preferably provide complementary coatings so as to develop an attractive result. The difference in coatings that can be used, based on the end result on hair tresses such as natural white hair non pre-bleached are as follows. As described within the CIELCh system:
 Coating 1 (LCh) versus Coating 2 (LCh)
 Coating 1 L-15<Coating 2 L<Coating 1 L+15
 0 or Coating 1 C-10<Coating 2 C<Coating 1 C+10
 Coating 1 h-45<Coating 2 h<Coating 1 h+45

The method for use of the multicomponent composition in accordance with the present invention can occur during any suitable period. The period of application can be from about 0 to 30 minutes, but in any event a period that is sufficiently long to permit the coating of pigment microparticles to coat and adhere or bind to each separate keratin fiber, substantially along the entire length of each keratin fiber. The resultant is keratin material having a coating and permanence that is at least equivalent to the coating resulting from oxidative in situ hair coating, except under much milder conditions.

The multicomponent compositions described herein can be prepared by the manufacturer as a full shade, e.g., one that is ready to apply to the hair, and then shipped as a discrete unit to the user. The user may need to re-blend the multicomponent composition prior to application to ensure that the multicomponent composition delivers the optimum performance. Such reblending can require shaking the multicomponent composition for about 1 to about 120 seconds or from about 3 to about 60 seconds. Reblending may also be performed by stirring the multicomponent composition prior to use. This may occur for about 1 to about 120 seconds or from about 3 to about 60 seconds. Although the multicomponent compositions according to the present invention are designed to provide stable suspensions of the pigment particles, the reblending to agitate the microparticles and resuspend them in a substantially uniform distribution is desirable.

Multiple compositions comprising different pigments can be blended together prior to application to the keratin material. Such blending can be done in a manner so as to apply a plurality of complementary surface coatings to the keratin material.

The multicomponent compositions can include multiple layers, involving multiple applications of at least the first and second components following the first application of the three components. It may be beneficial also to periodically reapply the third component. The techniques for applying multiple layers follow the techniques described above for application of a single multicomponent composition.

The coating of pigment microparticles comprising at least one pigment in a coating of the substantive constituents of the multicomponent composition can be adhered to the substrate material such as hair utilizing a coating having a total thickness at any given point along the hair fiber of less than about 5 μm, preferably less than about 2 μm us measured using a scanning electron microscope (SEM). To make such measurements, a coated hair sample can be embedded in a suitable resin, and then sectioned root to tip using techniques known to those skilled in the art of scanning electron microscopy. The thickness of the layer on the surface can then be assessed along the line of cuticles over a length of at least 100 μm. The thickness of layer is determined by averaging 10 points evenly spaced over the section of interest.

As described above, application of the multicomponent composition to sections of keratin material such as sections of hair strands can be varied. In addition to varying the concentration of the pigment microparticles and optional coating agent, different shades and/or coatings of multicomponent composition can be applied to different sections of a strand of hair or a group of strands of hair. For example, the hair roots, mid sections and tips sometimes or often have different shades of coating in their natural condition. This variation can be mimicked, altered or covered through use of differing shades or coatings of the multicomponent composition. Roots, for example can be covered with a lighter shade and the tips can be covered with a darker shade to produce a two tone variation of the hair. Application to the hair of a first portion of multicomponent composition followed by stripping the composition from the hair mid sections and ends followed by setting the remaining composition on the hair roots will provide a first hair coating on the roots. The mid-sections and tip can be dipped or brush applied with a second portion of multicomponent composition to complete the two coating or two tone treatment. The use of multiple multicomponent compositions to produce multiple coatings on the hair can provide overlapping, sequential or coterminous coatings on the hair according to typical and routine techniques for applying multiple versions of hair coating practiced by professional hair salons.

Post Treatment

An optional post treatment composition can be applied after treating the keratin material such as hair with the multicomponent compositions described herein. This can be applied either directly after completion of coating with the multicomponent composition. The post treatment can be either single application or multiple application across time. The post treatment can be used to improve one or more of feel, resistance to shampoo/conditioner/water washing treatments, and shine of the hair. Nonlimiting examples of materials used to improve the feel are those which impart lubricity to the keratin material such as hair strands and/or help the hair strands separate during the drying steps. These materials include, for example silicone conditioners, silicone polyethers, silicone polyglucose, polyisobutene, copolymers of ethylene and propylene oxide, and commonly used cosmetic oils and waxes. Nonlimiting examples of materials used to improve shampoo wash resistance are materials which act as a 'sacrificial layer' for example polymeric silicones and their copolymers, silicone resins, cosmetics oils and waxes, Nonlimiting examples of materials used to improve the shine of hair (meaning a decrease of the full width at half maximum parameter of the specular reflection curve as measured by a goniophotometer) are those materials which form a smooth film above the previously applied pigment polymer composite on the hair. In general, any cosmetically known film forming material can be used, but preferred are materials such as polymeric silicones and polycationic materials.

Removal of Coating

Hair coating made from surface films consisting essentially of a multicomponent coating plus a pigment, that are very resistant to everyday hair treatments (such as washing with shampoo, conditioner etc) can be removed via use of specifically designed "removal formulations." These are specific chemical mixtures, described herein, and are designed to work via one or both of two broad mechanisms.

First, the mixture can be made to be a solvent for the pigment itself. In this case the mechanism of removal involves first dissolution of the pigment from the binding matrix, followed by removal from the hair via rinsing with water or some other carrier. In this case it is believed, whilst not being bound by theory, that the chemical nature of the pigment, even when in dissolved form, is such that there is minimal attraction/solubility in the hair matrix itself, thus allowing removal of the coating.

Second, the 'removal formulation' can be made such that it dissolves, weakens or chemically breaks down the surface coating material holding the pigment on the hair. In this case it is believed, whilst not being bound by theory, that the pigments embedded in the binder matrix are released due to weakening or dissolution of the binder itself and, because the coating material is a pigment, it has minimal attraction for the hair surface and is too big to penetrate the hair, and in consequence this facilitates removal of the coating.

Within this second approach, it can be further subdivided into different approaches to weaken the surface coating. For example, it may be that a formulation could target the interaction between the pre-treatment and the hair itself, thereby disrupting the surface adhesion of the coating on the hair. Alternatively, it may alter the interaction between the pre-treatment and the layer produced by the multicomponent composition, again leading to the coating being able to be removed from the hair. Where new covalent bond have been formed between the compounds of the multicomponent composition, and also potentially with the pre-treatment and or hair itself, there are multiple routes to try to facilitate the removal. It may be possible to degrade the polymer chain itself, thereby leading to a reduction in the mechanical properties of the film. For example, those skilled in the art are aware of dcepolymerisation approaches for silicone based polymers wherein the more linear type polymers may be converted back into smaller silicone moieties, even back to cyclic silicones, for example use acid or base catalysis or an agent such as TBAF. Alternatively, the covalent bond formed during the formation of the coating may be reversed or changed such that it no longer as well connected. A further alternative approach may to break a bond in an alternative location within the compound or linking group which may have been designed into the compounds to facilitate later removal. With such approaches it is important that any actives are formulated within a suitable medium such that they can be delivered into the surface coating, for example through selection of solvents compatible with the coating.

The removal may be further enhanced by using energy to help to remove the coating. For example, if it has been weakened, the use of mechanical force, for example by rubbing the hair may help to remove the coating. This may be further enhanced by addition of components within the formulation which provide some gentle abrasive action on the coating surface, facilitating its removal. Mechanical force can also be provided through creating a composition which creates bubbles which produce the effect of local movement at the surface, again enhancing the removal of the coating. Forces can also be applied through a device which is applied to the hair at the same time as any removal formulation and which provide energy to the interface, for example but not limited to physical vibrations, ultrasonic vibrations or liquid or gas movement to help the remove the surface coating. A device may further be able to provide heating, either directly or through various means to couple electromagnetic energy into the removal formulation such that the process of weakening the film is accelerated.

Finally, the formulation itself may also be created such that it helps in the overall removal process. For example, it may be formulated with one or more surfactants to help the removal of the surface coating, it may be formulated such that the actives and solvents are emulsified within a third medium, for example water, in such a way as to make the removal process more efficient. The formulation can be created such that it has a desirable rheological profile such that it can be applied and used by the consumer with or without an application device.

A combination of the above mechanisms will also aid in providing the desired result of removal of the coating.

Changing the pH can have a dramatic impact on the properties of the coating which is adhered to the surface. A soluble base acting as a trigger agent to neutralize acid groups and enable the conjugate base to be readily soluble in a mixture of water and organic solvent will facilely remove the coating. Such bases include amino alcohols such as dimethylaminoethanol (dimethylethanolamine, DMEA), dimethylaminopropanol, and similar amino alkanol agents such as monoethanolamine, diethanolamine and triethanolamine and ammonia. Other bases such as NaOH and Ca(OH)2 can also be used. The concentration of the trigger agent in aqueous solution optionally with an alcohol or ketone organic solvent such as methanol, ethanol, methyl ethyl ketone and the like may range from about 0.1% to about 15% by weight, preferably about 0.5% to about 10% by weight, more preferably about 1% to about 7.5% by weight relative to the total weight of the removal solution.

Remanence and Keratin Material Inspection

Damage caused to the hair by application of the multicomponent composition and removal of the resulting coating can be assessed by FT-IR (Fourier Transform Infrared) method, which has been established to be suitable for studying the effects on keratin surface damage. (Strassburger, J., J. Soc. Cosmet Chem., 36, 61-74 (1985); Joy, M. & Lewis, D. M., Int. J. Cosmet. Sci., 13, 249-261 (1991); Signori, V. and Lewis, D. M. Int. J. Cosmet. Sci., 19, 1-13 (1997)). In particular, these authors have shown that the method is suitable for quantifying the amount of cysteic acid that is produced from the oxidation of cystine. In general, the oxidation of cystine is thought to be a suitable marker by which to monitor the overall oxidation of the keratinous part of the fiber. Also, the measurement of cysteic acid units by FT-IR is commonly used to study the effects of oxidative treatments or environmental oxidation upon keratin protein containing fibers such as hair and wool.

Signori and Lewis (D. M., Int. J. Cosmet. Sci., 19, 1-13 (1997)) have shown that FT-IR using a diamond Attenuated Total Internal Reflection (ATR) cell is a sensitive and reproducible way of measuring the cysteic acid content of single fibers and bundles. Hence, the method that we have employed to measure the cysteic acid content of multiple fiber bundles and full hair switches, is based upon the FTIR diamond cell ATR method employed by Signori and Lewis (1997), The detailed description of the method used for testing the different damage inhibitors follows thereafter:

A Perkin Elmer Spectrum® 1 Fourier Transform Infrared (FTIR) system equipped with a diamond Attenuated Total Internal Reflection (ATR) cell was used to measure the cysteic acid concentration in mammalian or synthetic hair. In this method, hair swatches of various sizes and coatings can be used. The switches were platted (~1 plait per cm) in order to minimize variations in surface area of contact between readings. The Oxidative hair Treatment Protocol described above was repeated for 5 cycles to mimic the behavior of hair after repeated bleaching cycles. Following this treatment, four readings per switch were taken (⅓ and ⅔s down the switch on both sides), and an average calculated. Backgrounds were collected every 4 readings, and an ATR cell pressure of 1 N/m was employed. The cell was cleaned with ethanol between each reading, and a contamination check performed using the monitor ratio mode of the instrument. As prescribed by Signori& Lewis in 1997, a normalized double derivative analysis routine was used. The original spectra were initially converted to absorbance, before being normalized to the 1450 cm$^{-1}$ band (the characteristic and invariant protein $CH_2$ stretch). This normalized absorbance was then twice derivatised using a 13 point averaging. The value of the 1450 cm$^{-1}$ normalized 2nd derivative of the absorbance at 1040 cm$^{-1}$ was taken as the relative concentration of cysteic acid. This figure was multiplied by $-1 \times 10^{-4}$ to recast it into suitable units. It was found that virgin mammalian or synthetic hair produced a value of around 20 cysteic acid units, and heavily oxidized hair produced values of around 170. The following instrumental conditions were employed:

Spectral Resolution—4 $cm^{-1}$
Data Interval—0.7 $cm^{-1}$
Mirror Scan Speed—0.2 cm $s^{-1}$
Number of Background Scans—20
Number of Sample Scans—20
Scan Range—4000 $cm^{-1}$ to 600 $cm^{-1}$ When the compositions of the current invention can be applied to the hair and then removed there can be a non-significant change to the level of oxidative damage to the hair, whereas with conventional oxidative coatings there can be a large increase in the measured damage.

The instant disclosure is not limited in scope by the specific compositions and methods described herein, since these embodiments are intended as illustration of several aspects of the disclosure. Any equivalents are intended to be within the scope of this disclosure, Indeed, various modifications in addition to those shown and described herein can be within the grasp of those with ordinary skill in the art. Such modifications are also intended to fall within the scope of the appended claims.

Coating Selection

Also contemplated herein are multicomponent compositions having a given coating area (gamut principle described above) defined by coating coordinates (a*, b*) in the coating space represented by the L*a*b* coating system, which can be divided into a plurality of coating areas. Each of the plurality of coatings obtained from the area surrounding a given set of hair fibers is judged to belong to which coating area of the coating area of a certain coating. The number of coatings judged for each coating area is counted, and the coating of the coating area with the largest number of coatings is selected as a representative coating of the area surrounding a given set of hair fibers.

Also contemplated herein are multicomponent compositions that do not change the underlying hair coating, but instead change some other feature of the hair including shine (e.g., making it shinier or matte), the thickness of the hair and/or the feel of the hair.

When the coating is removed from the keratin material such as hair, the waste water/composition can be treated to remove the pigments from the waste water effluent system. This can be achieved by filtration, or through cyclone technology, where the density differences are used to force the pigments to the settle, and the water.

Application Method for Multicomponent Composition

In certain embodiments, the multicomponent composition may be quite a thin, low rheology fluid. In such an embodiment, application to the hair cannot be performed using standard techniques used within the salon, for example using the so called brush and bowl technique to paint the product onto the hair. It may be too thin and may lead to excessive mess and may not have sufficient precision to target where the product is applied onto the hair. Alternatively, the product may be applied using an absorbent material, for example a tissue or a sponge, or through direct application using a device which performs the action of a pipette or syringe to dispense the product onto the hair or via a brush. These alternative approaches also present potential difficulties for the user of the multicomponent composition. For example, they may lead to excessive spilling or dripping of the composition, for example onto the floor or surrounding area, clothes of the persons skin. They may make it hard to target the application to the desired location on the hair, where only sections are desired to be treated with the multicomponent system and may lead to excessive product being applied to the scalp. Such approaches may lead to excessive product consumption with much of the product not being transferred as intended onto the hair leading to excessive waste for the user and or salon. They may also be very time consuming processes for a complete head application. The means of applying to the hair may not have a satisfactory environmental profile, with too much or all of the applicator needing to be disposed of after use. If the means are reused to apply the product to another person and or at another time, they may not provide the required level of hygiene control to meet regulatory, safety and consumer desires. The means may also require very high levels of mastery of the user to enable satisfactory performance, and in some cases may not enable the self-application of an "at home" user. The multicomponent composition may also have reactive individual components that can lead to clogging tubes of an applicator means and preventing multiple usage.

A solution to address at least one of the aforementioned difficulties of apply the multicomponent composition to the hair is to use a specific apparatus and or method for coating the hair.

In one embodiment the apparatus for coating the hair comprises a first and second mutually opposing arms adapted for movement between an open configuration for receiving a length of hair and a closing configuration adjacent to the hair.

The apparatus may further comprise a means of delivering the multicomponent composition to the hair. On at least a part of the internal surface of one or other or both of the two mutually opposing arms may be placed a means to deliver the coating to the hair. If these are on both of the internal surfaces, these may be configured such that the means to coat the hair are when the apparatus is in a closed configuration in a substantially juxtaposed position. The means to deliver the coating to the hair may comprise an absorbent and or dispensing material. Such a material may be porous foam like materials of one or multilayers to absorb and release and spread/distribute the said composition. Such materials may be chosen on their ability to both hold and retain the multicomponent composition, and to deliver it to the hair. For example, it may be selected based on one or more of the following; porosity, both the pore volume and the pore size and their distribution, the resilience and hardness of the material, the surface friction of the material, the biodegradability, the ability to be cleaned and retain the desired physical and chemical properties. The means to deliver the coating to the hair may be attached to one or other or both of the two mutually opposing arms using a permanent or temporary fixing. For example, temporary fixing may be achieved via a physical click-in mechanism, or via a Velcro like approach. Such an approach may facilitate the rapid transfer of delivering means and aid the filling and or cleaning of the applicator. The delivery means may be durable or disposable. They may also be preloaded with one component of the multicomponent composition. In such an embodiment, when two opposing delivery means are fixed into the apparatus, each may contain a different element of the multicomponent composition, the mixing of the multicomponent composition can occur in situ within the apparatus.

The apparatus may have an extension of the absorbent material at one of the arms for very targeted applications.

The applicator can be configured such that the when closed it can coat adjacent to the scalp, or with a predefined separation from the scalp. It may also be configured such that it contains bristles or tines to improve the separation of the hair fibers, further aiding the application of the coating onto the hair and individualizing the hair strands. Additional features may be added to the areas close to the perimeter of the internal surfaces of one or both of the opposable arms, such that when they are in a closed position they may form a means to remove any excess composition on the hair and may also help to further distribute it into the hair.

A separate cleaning station may also be provided for the apparatus to clean all or part of it ready for the next use.

The following describes potential embodiments for use of the applicator described above.

The applicator can be loaded with the multicomponent composition in various ways. The mixed composition can be directly applied to the internal surfaces of the apparatus in the delivery means, for example using a syringe or the like. Alternatively, the delivery means may be preloaded with either the multicomponent composition or a component of the multicomponent composition so that the final components will be formed on the hair only, avoiding clogging. They may then be loaded into the apparatus prior to use.

The user may then apply the multicomponent hair treatment composition with said applicator to a hair strand, wherein said method comprises selecting a bundle of hair strands, placing said hair strands in said applicator and bringing said applicator into said closed position and then swiping said applicator along the length of said hair strand. The swiping movement may be from hair root to tip or hair tip to root, or for some techniques along only a section of the hair. The process may be repeated as needed to deliver the desired effect.

After the product has been applied to the hair it may subsequently be dried, for example using a hair drier or other means of heating the hair to remove the volatile solvent, for example a straightening iron. The user may do this as one step, wherein they apply the product with the aforementioned application and simultaneously dry the hair as it exits said application. They may then choose to further dry the hair using a hair drier and or a straightening iron or similar device which can heat the product on hair. Alternatively, they may use the aforementioned applicator and a heated brush. In some embodiments it may be that the application device described above further contains a built in means to heat and dry the composition on the hair, enabling a one-step application process.

EXAMPLES

General

The coloring compositions described herein within the examples are generally applied to a hair tress, 1 gram of composition per gram of hair, on a flat plate and brushed into the hair to ensure that all of the strands look visibly coated with the composition. The hair tress is then dried by heating with a hair dryer while combing until it is dry to the touch and the strands are individualized.

Preparation and Application of a First and Second Component to Hair Pre-Treated with a Third Component Containing a Base Compound:

General Description of Steps:
Preparation procedure for third component which can be used as a pre-treatment.
Preparation procedure for the first component containing a first compound with an optional pigment.
Preparation procedure for the second component containing a second compound.
Preparation procedure for the multicomponent coloring composition.
Application of multicomponent color composition to hair tresses.
Standard Wash Procedure.

Preparation procedure for the third component which can be used as a pre-treatment. The separate third component or pro-treatment composition containing a base compound is prepared by combining the base compound, for example a polymer and water and mixing until uniform. The resulting mixture is the third component or pre-treatment composition.

Preparation Procedure for the First Component Containing a First Compound with an Optional Pigment.

The pigment is combined with isododecane. The first compound is then also added and then mixed until uniform using standard lab methods.

Preparation Procedure for the Second Component Containing a Second Compound with Second Functional Groups.

The second compound is added to the medium and mixed until uniform using standard lab mixing methods.

Preparation Procedure for the Multicomponent Coloring Composition.

Equal amounts of the first and second compositions prepared according the procedure above and combined and mixed until uniform. This mixture is the multicomponent color composition and is to be prepared just before application to the hair tresses.

Application of Multicomponent Coloring Composition to Hair Tresses.

Hair preparation: Two types of hair were used: un-damaged and damaged.

Un-damaged hair: Natural white undamaged human hair was purchased from Kerling International Haarfabrik GmbH, Backnang, Germany company in the form of 10 cm long and 1 cm wide strands. This hair was used as received. Natural dark brown, Level 4 hair was purchased from Kerling International Haarfabrik GmbH, Backnang, Germany company in the form of 10 cm long, 1 cm wide strands. This hair was used as received.

Damaged hair which was produced following this procedure: Natural white undamaged human hair was purchased from Kerling International Haarfabrik GmbH. Backnang, Germany company in the form of 10 cm long and 1 cm wide strands and was bleached. The strand was treated with a mixture of Blondor Multi-Blonde bleach powder available from Wella Professionals mixed 1 part with 1.5 parts of 12% Welloxon Perfect available from Wella Professionals. About 4 g of this mixture was applied to each gram of hair. The tresses were then incubated in an oven at 45 C for 30 minutes after which they are rinsed in water, 37+−2 C with a flow rate of 4 L/mini for 2 minutes and the hair is then dried with a standard Hair dryer from Wella.

Organic pigments were tested on the natural white hair as received and treated according to the protocol described above to assess the initial color and color remanence. TiO2 and Metal flakes were tested on the dark brown hair described above to assess initial color and color remanence.

Hair pre-treatment: Hair prepared as described above was treated with the pre-treatment composition described above, one gram of composition per one gram of hair. The composition was left on the hair between 1 and 5 min. The hair was then dried using a blow dryer to result in dry hair.

General Coloring Procedure: To the pre-treated hair tress described above is added a freshly prepared multicomponent coloring composition as described above, 1 gram per 1 gram of hair. Application is accomplished by a slow distribution and spreading on the hair tress, for example, with fingers, brush, comb or other manipulation instrument. The slow distribution can be accomplished by application with a syringe or a pipette serially to portions of the hair tress. Excess is removed with absorbent tissue material and the resulting colored hair tress is blow dried with combing using a hair dryer to achieve better hair individualization. Optionally when stated within the sections below, the hair was then pulled 3 times through a flat iron at 150° C., 2 seconds for each pull of the tress through the flat iron. Treated hair tresses were kept at rest for a time period over around a day at room temperature or at least above 17° C.

Standard wash procedure: The standard wash procedure is used to determine the remanence of the colored hair tresses.
1. Rinse the hair tress for approximately 10 seconds with water (4 L min⁻¹) at approximately 37+/−2 C.
2. Apply 0.1 g "Wella Professional Brilliance Shampoo for fine and normal hair" without dilution to the individual colored hair tress weighing about 1 g described above.
3. Shampoo is worked into the colored hair tress in the absence of water dilution for 30 sec with fingers by using a stroking motion into the hair.
4. The shampooed colored hair tress is rinsed with water for approximately 30 seconds.
5. The rinsed colored hair tress is then dried using a hot blow dryer while mechanically separating the fibers in the keratin material until uniformly dry.
6. Steps 1-5 described above represent one cycle of the standard wash procedure.
7. Repeat of standard wash cycle for multiple cycles and comparison of the multiply washed hair tress to an unwashed colored hair tress which indicates the degree of color remanence using the Color Remanence Scoring Values described below.

Remanence was assessed visually by comparing the washed samples versus a retained tress which had been colored but not washed. They were graded on a 5 point scale according to the following criteria, 1 no color left, 2 faint color, 3 washed-out color, 4 intense color with some color loss, 5 color unchanged versus reference.

Sebum test: The sebum test is used to determine the color remanence of the hair coated with a multicomponent coloring composition to sebum.
1. Apply 0.1 g of sebum like material, Hautfett nach BEY from W-Testgewewe GmbH, to the individual colored hair tress weighing about 1 g described above. The sebum is rubbed into the tress to distribute it evenly.
2. Leave the hair tress overnight at room temperature or at least above 17° C.
3. Rinse the hair tress for approximately 10 seconds with water (4 L min-1) at approximately 37+/−3 C.
4. Apply 0.1 g "Wella Professional Brilliance Shampoo for fine and normal hair" without dilution to the individual colored hair tress weighing about 1 g described above.
5. Shampoo is worked into the colored hair tress for about 30 sec with fingers by using a stroking motion into the hair.
6. The shampooed colored hair tress is rinsed with water for approximately 30 seconds.
7. The rinsed colored hair tress is then dried using a hot blow dryer while mechanically separating the fibers in the keratin material until uniformly dry.
8. Steps 1-5 described above represent one cycle of the standard wash procedure.
9. Repeat of standard wash cycle for 5 cycles and comparison of the multiply washed hair tress to an unwashed colored hair tress which indicates the degree of color remanence using the Color Remanence Scoring Values described below.

Color Removal Procedure
1. Apply 2 gram of color removal composition to 1 gram of colored hair tress.
2. The color removal composition is worked into the colored hair tress in the for approximately between 30 sec to 1 minute with fingers or a comb of manipulation instrument by using stroking motion into the hair.
3. Leave the color removal composition onto the colored hair tress for approximately 5 min unless stated differently.
5. Remove excess color removal composition with fingers first and then remove further remains with an absorbent tissue material.
6. Apply 0.1 g of "Wella Professional Brilliance Shampoo for fine and normal hair" without water dilution and work into the colored hair tress for 30 sec with fingers by using stroking motion into the hair.
7. The shampooed colored hair tress is rinsed with water.
8. The rinsed colored hair tress is then dried using a hot blow dryer until uniformly dry.

Film performance. This procedure was used to study the bulk film properties of the material formed when combining the first and second components. A film of the mixture of the two compounds was allowed to cure for 1 day prior to measurement for Shore OO hardness.

Procedure Details:
1. In a cylindrical aluminum weighing tray (radius ~3.5 cm) 10 gram of the mixture of the first and second compounds was dispensed and then mixed. The ratio of the first and second compounds in wt. % was adjusted to replicate the ratio of wt. % mixtures studied with the coloring compositions when mixed together. No other materials were added to the mixed first and second compound system.
2. The weigh boats were then placed in a 105 C oven for 60 minutes and then left overnight in a fume hood to cure for a further 24 hours before being measured.
3. The film was assessed with a plastic pipette to sec if the material had cured to form a film. If the mixture was still liquid, it was not measured for Shore Hardness to prevent damaging the measurement device. Instead a value of 0 was recorded, to represent a very soft material. Films that were measured were assessed for Shore OO using a HT-6510 OO Shore hardness tester (Guangzhou Landtek Instruments Co. Ltd). At least ten repeat measurements were performed on each sample and the average reported.

Examples as Tables: Multicomponent Coloring Composition with a First Component Containing a First Compound and a Second Component Containing Second Compound.

The following tables describe components, ingredients and procedures for preparation of exemplary compositions according to the invention. Following the Tables are descriptions of procedures and results.

TABLE 1

First Components containing first compound having olefinoyloxy groups and medium

| Material | Name | Supplier | 1B | 2B | 3B | 4B | 5B | 6B | 7B | 8B | 9B | 10B |
|---|---|---|---|---|---|---|---|---|---|---|---|---|
| First Compound | | | | | | | | | | | | |
| ACR silicone | Silmer OH ACR Di400 | Siltech | | | | | | 6% | | | | |
| ACR silicone | Silmer OH ACR Di50 | Siltech | | | | | | | | | | |
| ACR silicone | Silmer OH ACR C50 | Siltech | | | | | | | | | | |
| ACR silicone | Silmer OH ACR Di10 | Siltech | 4% | 2% | 2% | 4% | | 10% | 8% | 6% | 5% | 4% |
| Medium | | | | | | | | | | | | |
| Isododecane | 2,2,4,6,6-Pentamethylheptane | Brenntag | Qs 100% | Qs 100% | Qs 100% | Qs 100% | Qs 100% | Qs 100% | Qs 100% | Qs 100% | Qs 100% | Qs 100% |

| Material | Name | Supplier | 11B | 12B | 13B | 14B | 15B | 16B | 17B | 18B | 19B | 20B |
|---|---|---|---|---|---|---|---|---|---|---|---|---|
| First Compound | | | | | | | | | | 4% | | |
| ACR silicone | Silmer OH ACR Di400 | Siltech | | | | | | | | | | 4% |
| ACR silicone | Silmer OH ACR Di50 | Siltech | | | | | | | | | 4% | |
| ACR silicone | Silmer OH ACR C50 | Siltech | | | | | | | | | | |
| ACR silicone | Silmer OH ACR Di10 | Siltech | 2% | | 4% | 2% | 4% | 2% | 8% | | | |
| Medium | | | | | | | | | | | | |
| Isododecane | 2,2,4,6,6-Pentamethylheptane | Brenntag | Qs 100% | Qs 100% | Qs 100% | Qs 100% | Qs 100% | Qs 100% | Qs 100% | Qs 100% | Qs 100% | Qs 100% |

| Material | Name | Supplier | 21B | 22B | 23B | 24B | 25B | 26B | 27B | 28B | 29B | 30B |
|---|---|---|---|---|---|---|---|---|---|---|---|---|
| First Compound | | | | | | | | | | | | |
| ACR silicone | Silmer OH ACR Di400 | Siltech | | | | 2% | | 4% | | | | |
| ACR silicone | Silmer OH ACR Di50 | Siltech | | | | | | | 4% | | | 4% |
| ACR silicone | Silmer OH ACR C50 | Siltech | | | | | 5% | | | | | |
| ACR silicone | Silmer OH ACR Di25 | Siltech | 4% | | | | | | | | | |
| ACR silicone | Silmer OH ACR Di A15 | Siltech | | 4% | | | | | | 4% | | |
| ACR silicone | Silmer OH ACR Di10 | Siltech | | | 4% | | | | | | 2% | |
| Medium | | | | | | | | | | | | |
| Isododecane | 2,2,4,6,6-Pentamethylheptane | Brenntag | Qs 100% | Qs 100% | Qs 100% | Qs 100% | Qs 100% | Qs 100% | Qs 100% | Qs 100% | Qs 100% | Qs 100% |

| Material | Name | Supplier | 31B | 32B | 33B | 34B | 35B | 36B | 37B | 38B | 39B | 40B |
|---|---|---|---|---|---|---|---|---|---|---|---|---|
| First Compound | | | | | | | | | | | | |
| ACR silicone | Silmer OH ACR Di400 | Siltech | | | | | | | | | | |
| ACR silicone | Silmer OH ACR Di50 | Siltech | | | | | | | | | | |
| ACR silicone | Silmer OH ACR C50 | Siltech | 5% | | 5% | | | | | | | |
| ACR silicone | Silmer OH ACR Di25 | Siltech | | | | | | | | | | |
| ACR silicone | Silmer OH ACR Di A15 | Siltech | | | | | | | | | | |
| ACR silicone | Silmer OH ACR Di10 | Siltech | | 2% | | 4% | 4% | 4% | 4% | 4% | 4% | 4% |
| Medium | | | | | | | | | | | | |
| Isododecane | 2,2,4,6,6-Pentamethylheptane | Brenntag | Qs 100% | Qs 100% | Qs 100% | Qs 100% | Qs 100% | Qs 100% | Qs 100% | Qs 100% | Qs 100% | Qs 100% |

| Material | Name | Supplier | 41B | 42B | 43B | 44B | 45B | 46B | 47B | 48B | 49B | 50B |
|---|---|---|---|---|---|---|---|---|---|---|---|---|
| Pigment Red 122 | Hostaperm Pink E M250 | Clariant | | | | | | | | | 1% | |
| First Compound | | | | | | | | | | | | |
| ACR silicone | Silmer OH ACR Di400 | Siltech | | | | | | | | | | 8% |
| ACR silicone | Silmer OH ACR Di50 | Siltech | 4% | 4% | | 4% | | | | | | |
| ACR silicone | Silmer OH ACR C50 | Siltech | | | | | 5% | 6% | | | | |
| ACR silicone | Silmer OH ACR Di25 | Siltech | | | | | | | | | | |
| ACR silicone | Silmer OH ACR Di A15 | Siltech | | | | | | | | | | |
| ACR silicone | Silmer OH ACR Di10 | Siltech | | | 2% | | | | | | | |
| PETTA | Pentaerythritol Tetraacrylate | Sigma Aldrich | | | | | | | 2% | 2% | 1% | |
| Medium | | | | | | | | | | | | |
| Isododecane | 2,2,4,6,6-Pentamethylheptane | Brenntag | Qs 100% | Qs 100% | Qs 100% | Qs 100% | Qs 100% | Qs 100% | | 60% | | Qs 100% |
| Ethanol | | | | | | | | | Qs 100% | Qs 100% | Qs 100% | |
| Water | | | | | | | | | | 60% | | |

TABLE 2

Second Components containing second compound having amine groups and optional pigments(s) and medium

| Material | Name | Supplier | 1A | 2A | 3A | 4A | 5A | 6A | 7A | 8A | 9A | 10A |
|---|---|---|---|---|---|---|---|---|---|---|---|---|
| Pigments(s) | | | | | | | | | | | | |
| Pigment Red 122 | Hostaperm Pink E M250 | Clariant | | 2.0% | 2.0% | 2.0% | 2.0% | 2.0% | 2.0% | 2.0% | 2.0% | 2.0% |
| Second Compound | | | | | | | | | | | | |
| Aminosilicone | Silamine 2972 | Siltech | 6% | 8% | | | 4% | | 2% | 4% | 5% | 6% |
| Aminosilicone | Silamine MUE | Siltech | | | | | | | | | | |
| Aminosilicone | Silmer NH C50 | Siltech | | | | | | 6% | | | | |
| Aminosilicone | Silmer NH E47 | Siltech | | | | 8% | | | | | | |
| Medium | | | | | | | | | | | | |
| Isododecane | 2,2,4,6,6-Pentamethylheptane | Brenntag | Qs 100% | Qs 100% | Qs 100% | Qs 100% | Qs 100% | Qs 100% | Qs 100% | Qs 100% | Qs 100% | Qs 100% |

| Material | Name | Supplier | 11A | 12A | 13A | 14A | 15A | 16A | 17A | 18A | 19A | 20A |
|---|---|---|---|---|---|---|---|---|---|---|---|---|
| Pigments(s) | | | | | | | | | | | | |
| Pigment Red 122 | Hostaperm Pink E M250 | Clariant | | 2.0% | 2.0% | 2.0% | 2.0% | 2.0% | 2.0% | 2.0% | 2.0% | 2.0% |
| Second Compound | | | | | | | | | | | | |
| Aminosilicone | Silamine 2972 | Siltech | 8% | 10% | 6% | | | | | 6% | 6% | 6% |
| Aminosilicone | Silamine MUE | Siltech | | | | | | 6% | | | | |
| Aminosilicone | Silmer NH C50 | Siltech | | | | | | | 8% | | | |
| Aminosilicone | Silmer NH E47 | Siltech | | | | | 8% | | | | | |
| Aminosilicone | Silmer NH Di8 | Siltech | | | | | | | 2% | | | |
| Medium | | | | | | | | | | | | |
| Isododecane | 2,2,4,6,6-Pentamethylheptane | Brenntag | Qs 100% | Qs 100% | Qs 100% | Qs 100% | Qs 100% | Qs 100% | Qs 100% | Qs 100% | Os 100% | Qs 100% |

| Material | Name | Supplier | 21A | 22A | 23A | 24A | 25A | 26A | 27A | 28A | 29A | 30A |
|---|---|---|---|---|---|---|---|---|---|---|---|---|
| Pigments(s) | | | | | | | | | | | | |
| Pigment Red 122 | Hostaperm Pink E M250 | Clariant | | 2.0% | 2.0% | 2.0% | 2.0% | 2.0% | 2.0% | 2.0% | 2.0% | 2.0% |
| Second Compound | | | | | | | | | | | | |
| Aminosilicone | Silamine 2972 | Siltech | 6% | 6% | 6% | | | 6% | | 6% | 8% | 6% |
| Aminosilicone | Silamine MUE | Siltech | | | | | | | 6% | | | |
| Aminosilicone | Silmer NH C50 | Siltech | | | | | 5% | | | | | |
| Aminosilicone | Silmer NH E47 | Siltech | | | | 8% | | | | | | |
| Aminosilicone | Silmer NH Di8 | Siltech | | | | | | | | | | |
| Medium | | | | | | | | | | | | |
| Isododecane | 2,2,4,6,6-Pentamethylheptane | Brenntag | Qs 100% | Qs 100% | Qs 100% | Qs 100% | Qs 100% | Qs 100% | Qs 100% | Qs 100% | Qs 100% | Qs 100% |

| Material | Name | Supplier | 31A | 32A | 33A | 34A | 35A | 36A | 37A | 38A | 39A | 40A |
|---|---|---|---|---|---|---|---|---|---|---|---|---|
| Pigments(s) | | | | | | | | | | | | |
| Pigment Red 122 | Hostaperm Pink E M250 | Clariant | 2.0% | 2.0% | 2.0% | 2.0% | | | | | | 2.0% |
| Pigment Red 112 | Permanent Red FGR M250 | Clariant | | | | | | | 0.42% | | | |
| Pigment Yellow 83 | Novoperm Yellow HR 70 M250 | Clariant | | | | | 2% | | 1.36% | | | |
| Pigment Green 36 | Heliogen Green L 9362 | BASF | | | | | | 3% | | | | |
| Pigment Black 7 | Midnight Black carbon black | Geotech | | | | | | | 0.22% | 2% | | |
| Second Compound | | | | | | | | | | | | |
| Aminosilicone | Silamine 2972 | Siltech | | | | | 6% | 6% | 6% | 6% | 6% | 6% |
| Aminosilicone | Silamine MUE | Siltech | | 8% | | | | | | | | |
| Aminosilicone | Silmer NH C50 | Siltech | 5% | | 5% | | | | | | | |
| Aminosilicone | Silmer NH E47 | Siltech | | | | | | | | | | |
| Aminosilicone | Silmer NH Di8 | Siltech | | | | | | | | | | |
| Medium | | | | | | | | | | | | |
| Isododecane | 2,2,4,6,6-Pentamethylheptane | Brenntag | Qs 100% | Qs 100% | Qs 100% | Qs 100% | Qs 100% | Qs 100% | Qs 100% | Qs 100% | Qs 100% | Qs 100% |

TABLE 2-continued

Second Components containing second compound having amine groups and optional pigments(s) and medium

| Material | Name | Supplier | 41A | 42A | 43A | 44A | 45A | 46A | 47A | 48A | 49A | 50A |
|---|---|---|---|---|---|---|---|---|---|---|---|---|
| Pigments(s) | | | | | | | | | | | | |
| Pigment Red 122 | Hostaperm Pink E M250 | Clariant | 2.0% | 2.0% | 2.0% | 2.0% | 2.0% | 2.0% | 2.0% | 2.0% | | 2% |
| Second Compound | | | | | | | | | | | | |
| Aminosilicone | Silamine 2972 | Siltech | 6% | | | | | | 4% | 5% | | |
| Aminosilicone | Silamine MUE | Siltech | | | | | 6% | | | | | |
| Aminosilicone | Silmer NH C50 | Siltech | | | 6% | 8% | | 5% | | | | |
| Aminosilicone | Silmer NH E47 | Siltech | | | | | | | | | | 2% |
| Aminosilicone | Silmer NH Di8 | Siltech | | | | | | | | | | |
| Chitosan | Koyo Chitosan (Flonac Grade) | Koyo Chemical Co | | | | | | | | 5% | | |
| Formic acid | 98+% Formic acid | Sigma Aldrich | | | | | | | | 2.5% | | |
| Medium | | | | | | | | | | | | |
| Isododecane | 2,2,4,6,6-Pentamethylheptane | Brenntag | Qs 100% | Qs 100% | Qs 100% | Qs 100% | Qs 100% | Qs 100% | | Qs 100% | Qs 100% | Qs 100% |
| Ethanol? | | | | | | | | | | | | |
| Water | | | | | | | | | | Qs 100% | | |

TABLE 3

Third Components containing base compound and medium

| Material | Name | Supplier | 1C | 2C | 3C | 4C |
|---|---|---|---|---|---|---|
| Al flakes | EMRS D710 Glass coated | Toyal | | | 5% | |
| Base Compound | | | | | | |
| Aminosilane | (3-Aminopropyl)triethoxysilane | Aldrich | | 1.0% | | |
| Polyethyleneimine | Epomin P-1050 | Nippon Shukobai | 1.0% | | 1.0% | 2.0% |
| Medium | | | | | | |
| Water | DI Water | Lab source | QS 100% | Qs 100% | Qs 100% | Qs 100% |

TABLE 4

Compositions for color removal

| Material | Name | Supplier | 1D | 2D | 3D | 4D | 5D | 6D | 7D | 8D |
|---|---|---|---|---|---|---|---|---|---|---|
| Medium | | | | | | | | | | |
| Solvent | Isododecane | Brenntag | Qs 100% | Qs 100% | | | 15% | 10% | | |
| Solvent | n-Octylpyrolidone | Aldrich | | | Qs 100% | Qs 100% | | | | |
| Solvent | DI Water | Lab sourced | | | | | 1.5% | 1.5% | 50% | 95% |
| Solvent | i-Propanol | | | | | | 10% | 10% | | |
| Oil Phase | Liquid petroleum jelly, Marcol 82 | ExxonMobil | | | | | 55% | 55% | | |
| Surfactant | Octyldodecanol, Eutanol G | BASF | | | | | 10% | 10% | | |
| Clay | Distearyldimethylammonium-modified hectorite, FGEL 200 | FCC Inc | | | | | 1.5% | 1.5% | | |
| Surfactant | Oleyl alcohol 10 OE | Croda | | | | | 5% | 5% | | |
| Solvent | Propylene carbonate | Sigma Aldrich | | | | | 0.5% | 0.5% | | |
| Agent | | | | | | | | | | |
| Acid | Dodecyl benzene sulfonic acid (70% in 2-Propanol) | Sigma Aldrich | 5.7% | | | | 1.43% | 1.43% | | |
| Fluoride source | 75% TBAF in water | Sigma Aldrich | | | 1.33% | | | | | |
| Abrasive | Zeodent 103 Silicon Dioxide | Evonik | | | | | | 5% | | |
| Carbonate | Sodium Carbonate | Sigma Aldrich | | | | | | | 50% | |
| Acid | Citric Acid | Sigma Aldrich | | | | | | | | 5% |

Example 1: Long Lasting Hair Conditioning

In a first series of experiments, the ability of the multicomponent composition to provide long lasting hair conditioning performance was investigated. On dark hair which had been previously bleached twice, using the method described above for highly bleached hair, an initial pre-treatment of 1C was applied, and the hair subsequently dried. A multicomponent composition comprising one part of formula 1A was mixed with one part of formula 1B, and the resulting mixture was then applied to the hair tress according to the protocol above. After drying, the hair fibers were assessed to be individualized and free flowing and were felt to be in better condition versus the previously twice bleached hair prior to application of the pre-treatment and multicomponent composition. FIG. 1 shows the silicone remanence before application of the multicomponent composition, after initial application of the multicomponent composition and again after 15 wash cycles performed using the method described above. Silicone levels were assessed using an ATR FT-R method. A Bruker Tensor 2 FT-IR spectrometer was used, fitted with ATR cell with a diamond crystal Platinum (Bruker). The software for normalization and integration used was Opus (Bruker). The measurement assesses silicone on the hair surface via integration of the Si—CH$_3$ signal at 1260 cm-1. After the standard background checks were performed an infrared spectrum of the hair sample was acquired using 64 scans, 4 cm-1 resolution and a spectral range of 600-4000 cm-1. For each sample point, a min-max normalization was performed in the spectral region 1425-1475 cm-1 followed by integration in the wavenumber region 1240-1280 cm-1. This result is a relative peak intensity in arbitrary units of the Si—CH3 band. This was performed on three points on each hair tress and on two hair tresses for each sample.

Results showed that the silicone on hair was remanent with a high level remaining after 15 washes, about 60% of the level after initial application. Further when assessed after the 15 wash cycles, the hair was still felt to be in better condition versus the hair prior to application of the multicomponent composition. This experiment demonstrated the remanence of the hair conditioning performance of the multicomponent composition on bleached hair.

Example 2: Color Remanence with and without Pre-Treatment

Figure 2:
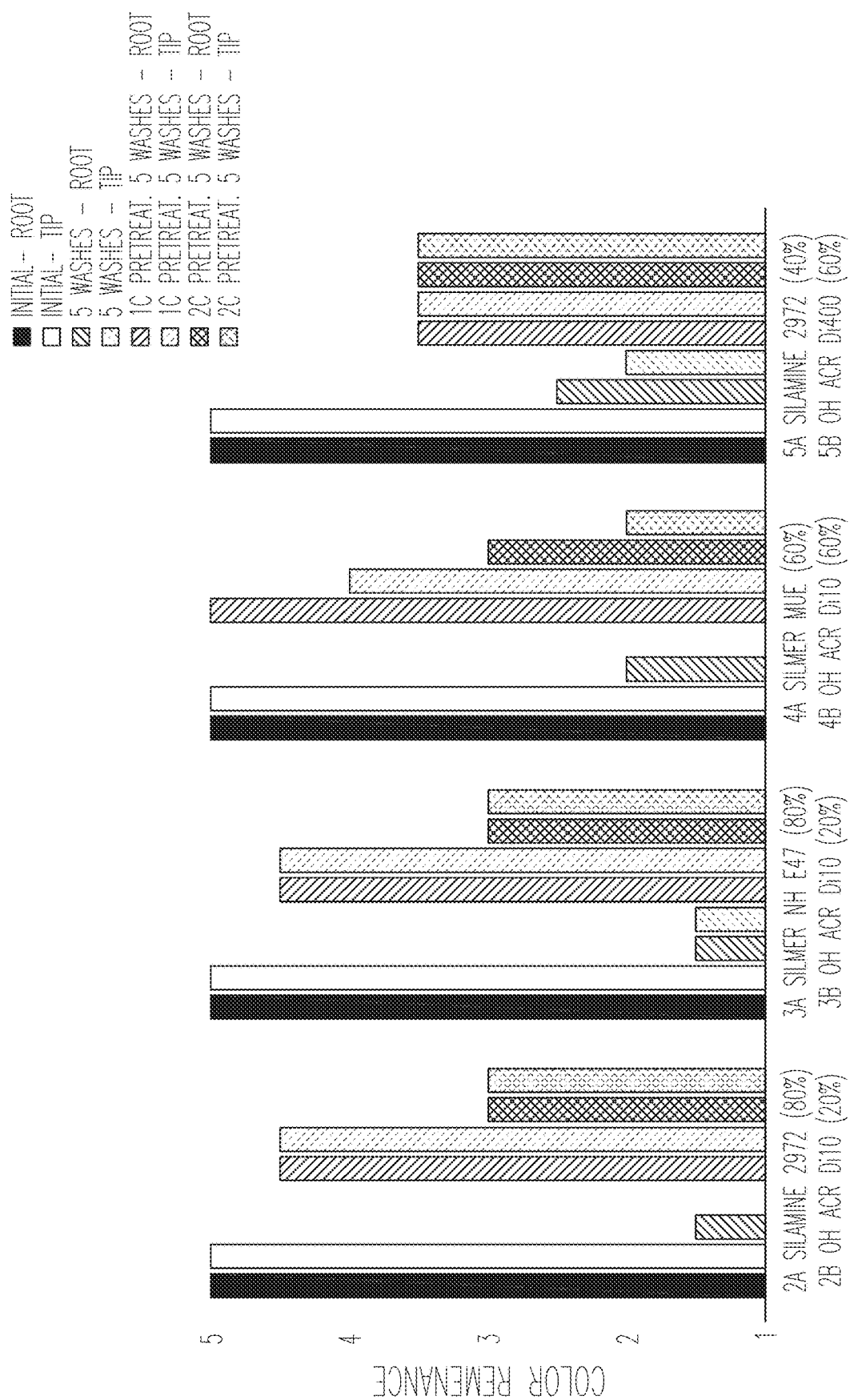
FIG. 2. Chart showing the color remanence after 5 wash cycles of a series of multicomponent compositions with and without pre-treatments 1C and 2C.

A second series of studies was performed using multicomponent compositions further comprising a pigment and different ratios of different silicones with first functional groups and different silicones with second functional groups. In the following four experiments a part of the A formula was mixed with a part of the B formula before application to the hair tress. Prior to application of the multicomponent composition the hair was optionally pre-treated with either 1C or 2C using the protocol described above with the hair dried using a hair drier. The values in parenthesis are relative proportions of each silicone within the silicone mixture, with the total silicone level maintained at a constant level of 5%. FIG. 2 shows the color remanence as assessed by the color remanence grading scale after initial application and after 15 washes on root and tip hair tresses.

Results show that both of the pre-treatments 1C and 2C increased the color remanence across the root and tip hairs. The pre-treatment 1C performed even more strongly than the pre-treatment 2C. The use of a pretreatment can therefore be used to alter the level of color remanence.

Example 3: Color Remanence Versus First and Second Component Ratios

Figure 3:
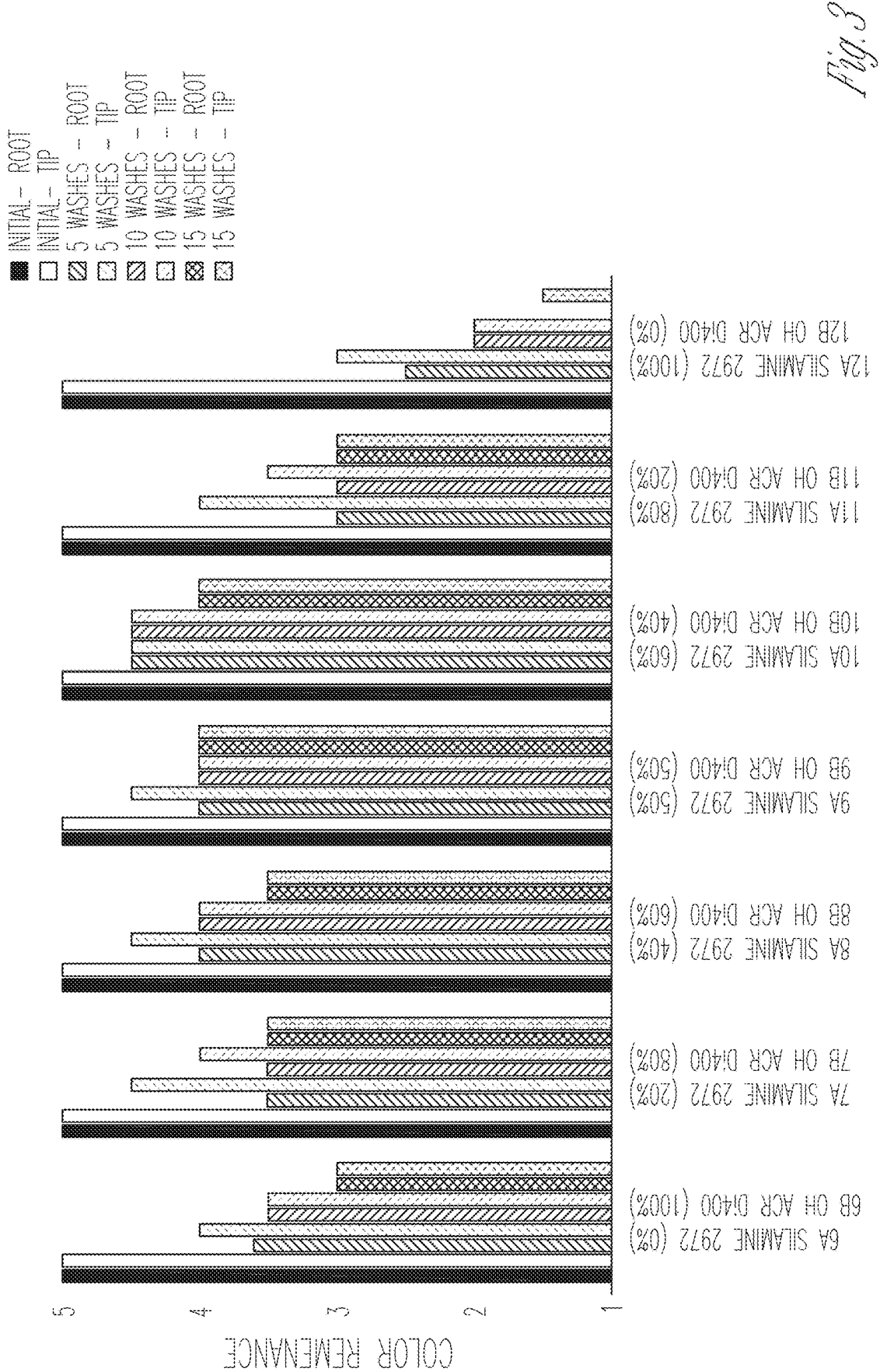
FIG. 3. Plot of color remanence of a series of multicomponent compositions with different ratios of the first and second compounds.

Results from a third series of studies performed using multicomponent compositions with different ratios of silicones with first functional groups and silicones with second functional groups are now described. In the following seven experiments a part of the A formula, was mixed with a part of the B formula before application to the hair tress. The values in parenthesis are relative proportions of each silicone within the silicone mixture, with the total silicone level maintained at a constant level of 5%. FIG. 3 shows the color remanence as assessed by the color remanence grading scale after initial application, and after 5, 10 and 15 washes on root and tip hair tresses. In all cases, a pre-treatment using 1C had been performed on the hair tresses prior to application of the multicomponent composition.

The results from these experiments show that there is a marked relationship between color remanence and mix ratio of the two different silicones. When the aminosilicone is used alone, the color remanence is very low, however for systems using a mixture of the two polymers, the performance is strong with a considerable amount of color remaining of both hair types after 15 hair washes. Surprisingly the performance of the olefinoyloxy silicone alone is still strong. Whilst not wishing to be bound by any particular theory, it's believed that this material is able to form a strong film in combination with the pre-treatment polymer used within 1C, and this resulting material is able to hold the pigments onto the hair. These results show the benefit of the mixed silicone system, and the combination of the olefinoyloxy silicone in combination with an amine containing base compound polymer. The pretreatment 1C, together with compositions 10A and 10B mixed 1 to 1 were applied using the methods described above on sections of human hair directly on a person. The results also showed that the color remained remanent on the persons hair over multiple washes.

Example 4: Color Remanence Performance of Different Aminosilicones

Figure 4:
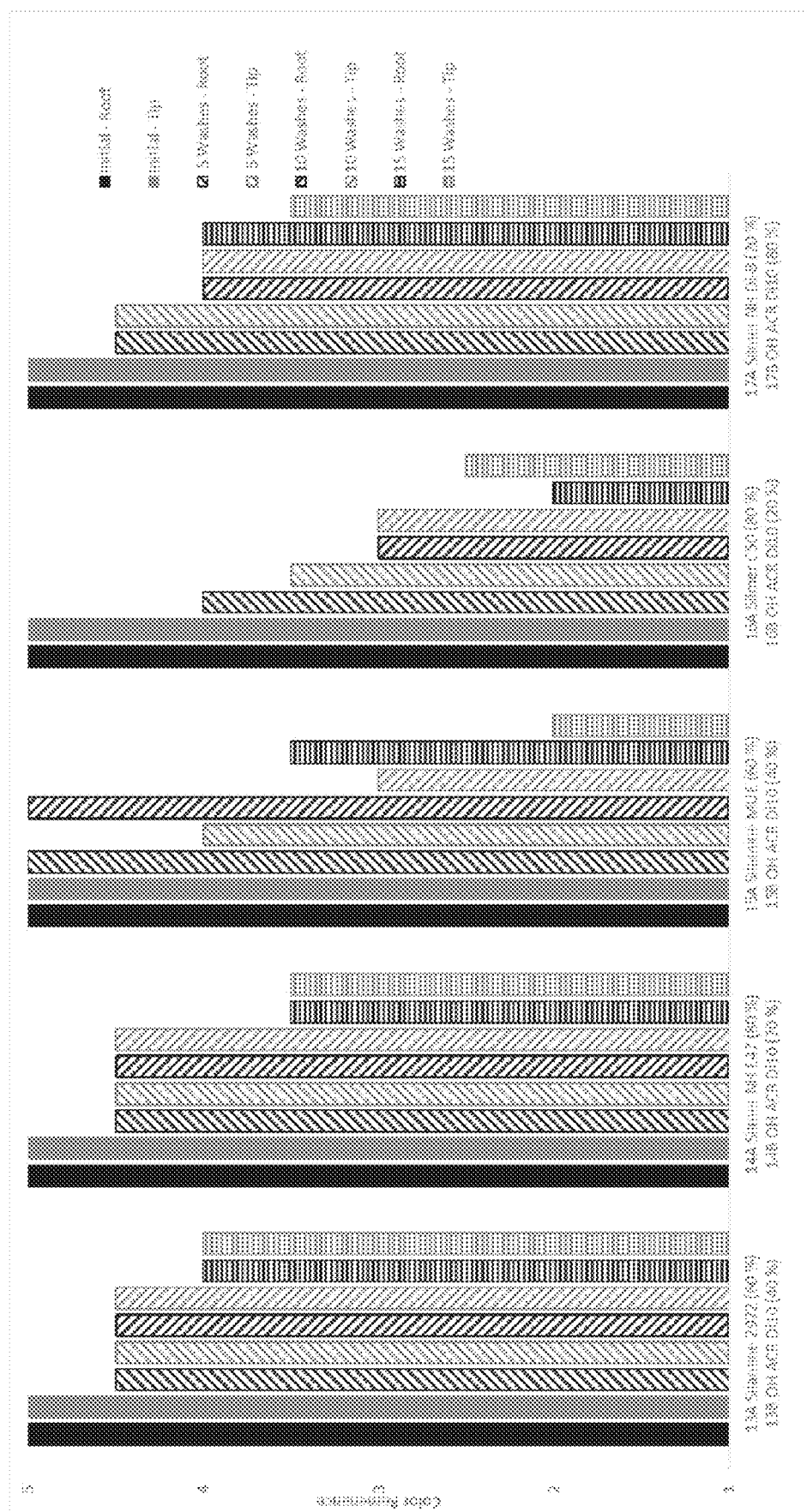
FIG. 4. Color remanence of a series of multicomponent compositions using different second compounds.

The results from a fourth series of studies are shown using multicomponent compositions comprising a pigment and different ratios of silicones with first functional groups and different silicones with second functional groups. In the following five experiments a pan of the A formula was mixed with a part of the B formula before application to the hair tress. The values in parenthesis are relative proportions of each silicone within the silicone mixture, with the total silicone level maintained at a constant level of 5%. FIG. 4 shows the color remanence as assessed by the color remanence grading scale after initial application, and after 5, 10 and 15 washes on root and tip hair tresses where 1C had already been applied as a pretreatment.

These results show for the different multicomponent compositions there are varying degrees of color remanence. The condensation curable, graft aminosilicones (Silamine 2972 and Silamine MUE) provide reasonable performance, as do the non condensation curable, graft aminosilicones (Silmer NH E47 and Silmer C50) and the terminal aminosilicone NH Di-8.

Example 5: Color Remanence Performance of Different Olefinoyloxy Silicones

Figure 5:
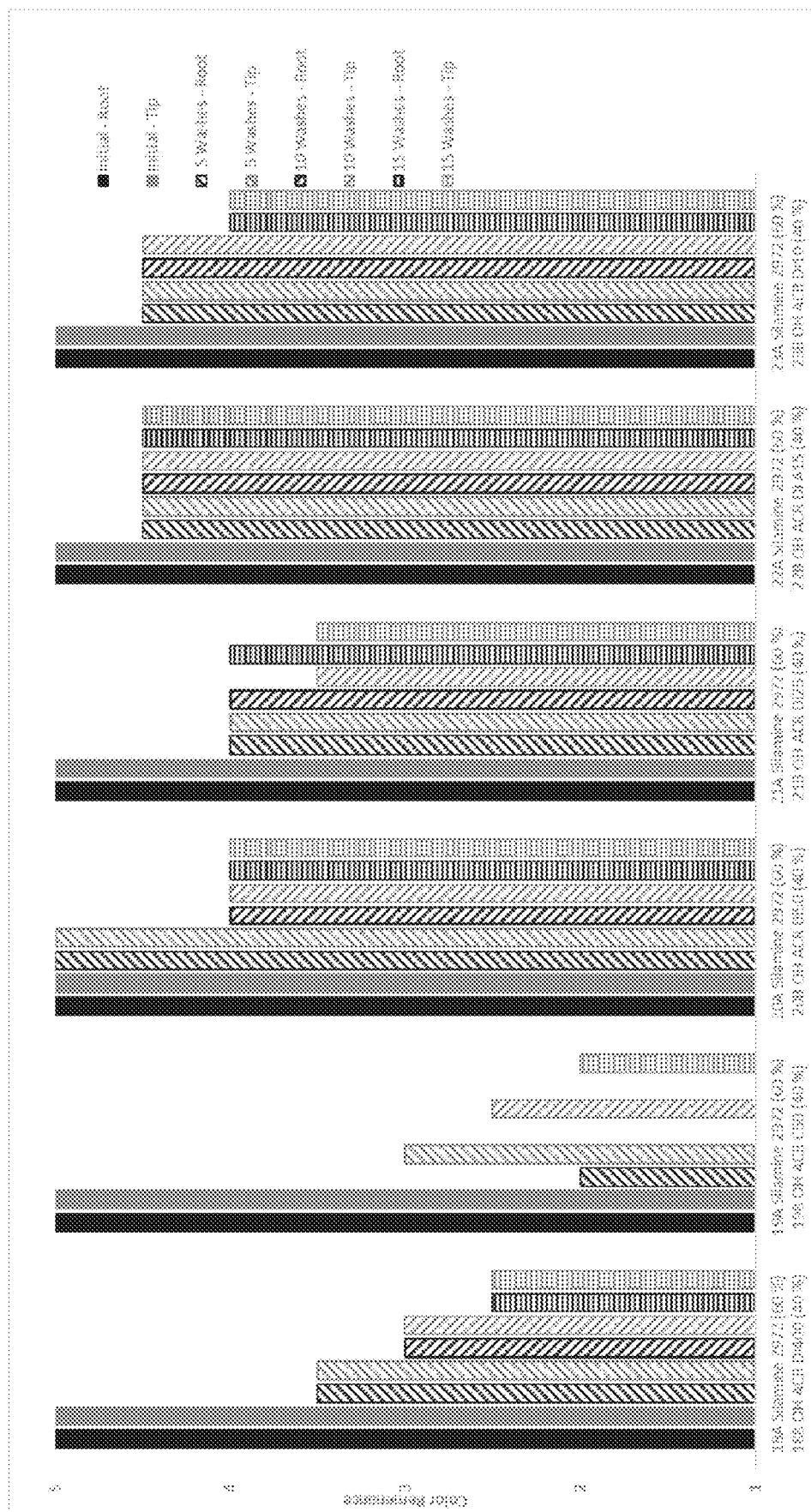
FIG. 5. Results for color remanence of a series of multicomponent compositions using different first compounds.

Results from a fifth series of studies performed using multicomponent compositions comprising a pigment and 4different ratios of different silicones with first functional groups and silicones with second functional groups. In the following six experiments a part of the A formula was mixed with a part of the B formula before application to the hair tress. The value, in parenthesis are relative proportions of each silicone within the silicone mixture, with the total silicone level maintained at a constant level of 5%. FIG. 5 shows the color remanence as assessed by the color remanence grading scale after initial application, and after 5, 10 and 15 washes on wet and tip hair tresses where 1C was used as a pretreatment.

These results show that for each and every combination of the first and second components there was a degree of color remanence, and that the amount of remanence could had some dependency on the choice of the olefinoyloxy silicone used. As the level of functionality increases, the remanence is increased.

Example 6: Color Remanence Performance to Sebum Test

Figure 6:
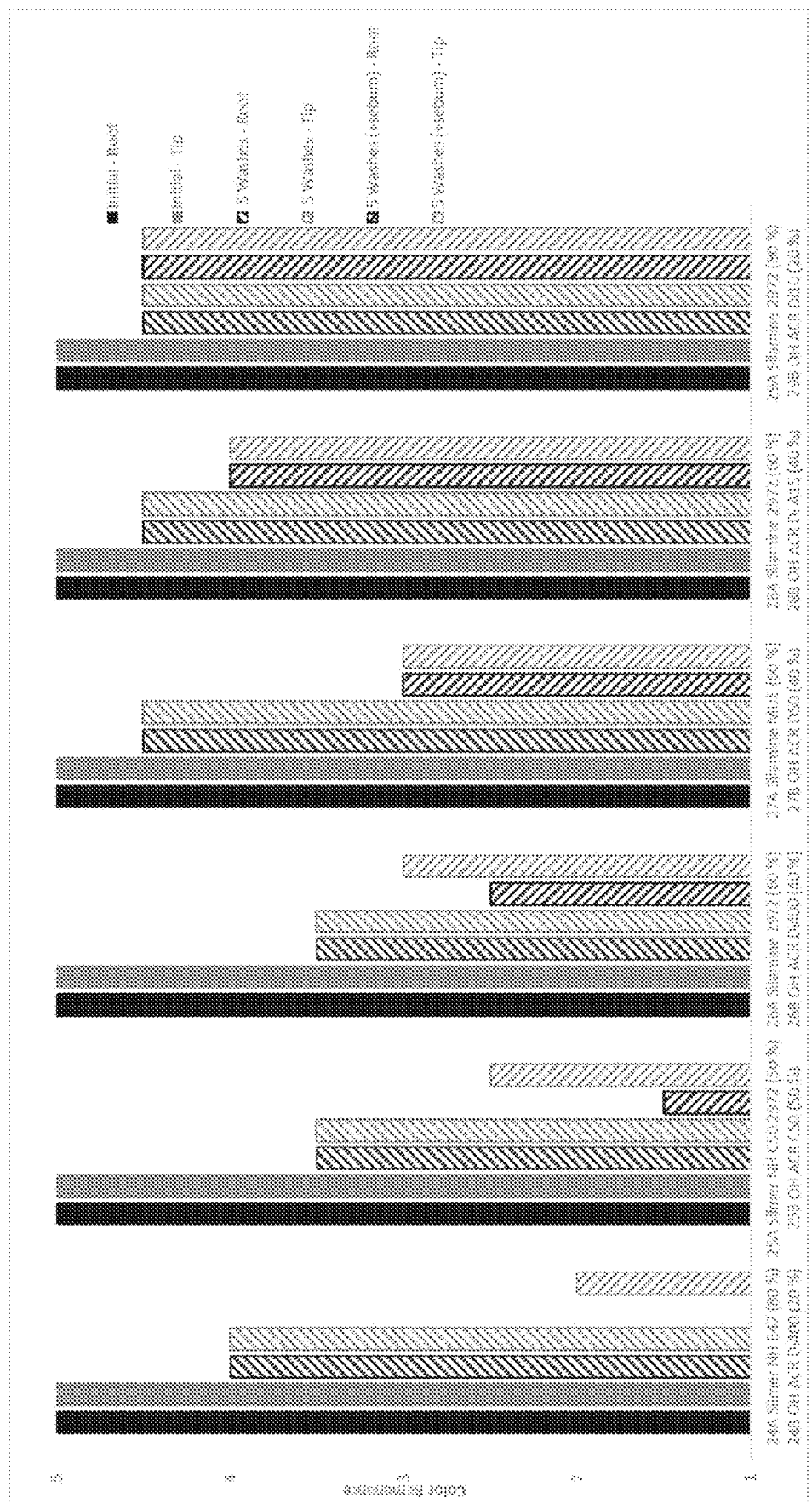
FIG. 6. Chart showing the color remanence after 5 sebum wash cycles of a series of multicomponent compositions.

Results from a sixth series of studies performed using multicomponent compositions comprising a pigment and different ratios of different silicones with first functional groups and different silicones with second functional groups. In the following six experiments a part of the A formula was mixed with a part of the B formula before application to the hair tress. The values in parenthesis are relative proportions of each silicone within the silicone mixture, with the total silicone level maintained at a constant level of 5%. FIG. 6 shows the color remanence as assessed by the color remanence grading scale after initial application where 1C was used as a pretreatment, and after 5 washes on root and tip hair tresses using the sebum test wash protocol described above.

These results show that the level of remanence in the presence of sebum can be controlled by the selection of the first and second compounds and their relative ratio. Multicomponent compositions can be created which are temporary, lasting only a few washers, up to those which can last many hair washes.

Example 7: Influence of Curing Protocol on Color Remanence

Figure 7:
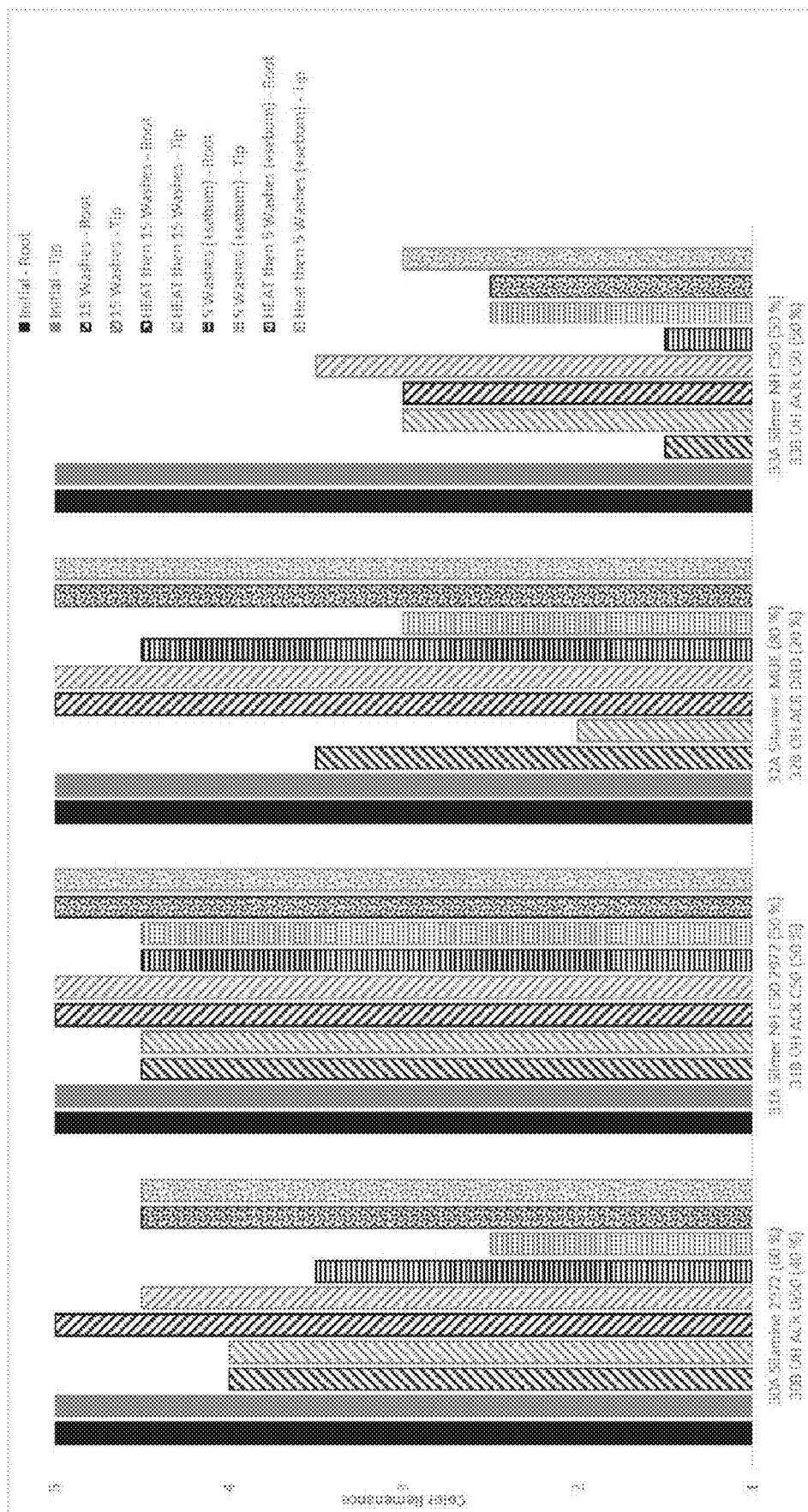
FIG. 7. Figure showing the impact of an additional heating step to enhance the remanence of the colored layer on hair.

Results from a seventh series of studies performed using multicomponent compositions comprising a pigment and different ratios of different silicones with first functional groups and different silicones with second functional groups. Within these experiments the hair was either blow dried as per the method described above, or received an additional heat treatment via a straightening iron as per the protocol described above. In the following four experiments a part of the A formula was mixed with a part of the B formula before application to the hair tress. The values in parenthesis are relative proportions of each silicone within the silicone mixture, with the total silicone level maintained at a constant level of 5%. FIG. 7 shows the color remanence as assessed by the color remanence grading scale after initial application, and after 15 washes on root and tip hair tresses where 1C was used as a pretreatment and when S washes were performed using the sebum wash protocol described above. Within the legend of the graph, HEAT refers to tresses prepared with the additional straightening iron step described above.

These results show on the multicomponent compositions tested, that the remanence could be enhanced by the application of beat to the hair. Whilst not wishing to be bound by theory, it believed that this could accelerate the cross linking within the layer on the hair, which helps it to resist shampooing more.

Example 8: Different Pigments Tested in the Multicomponent Composition

Figure 8:
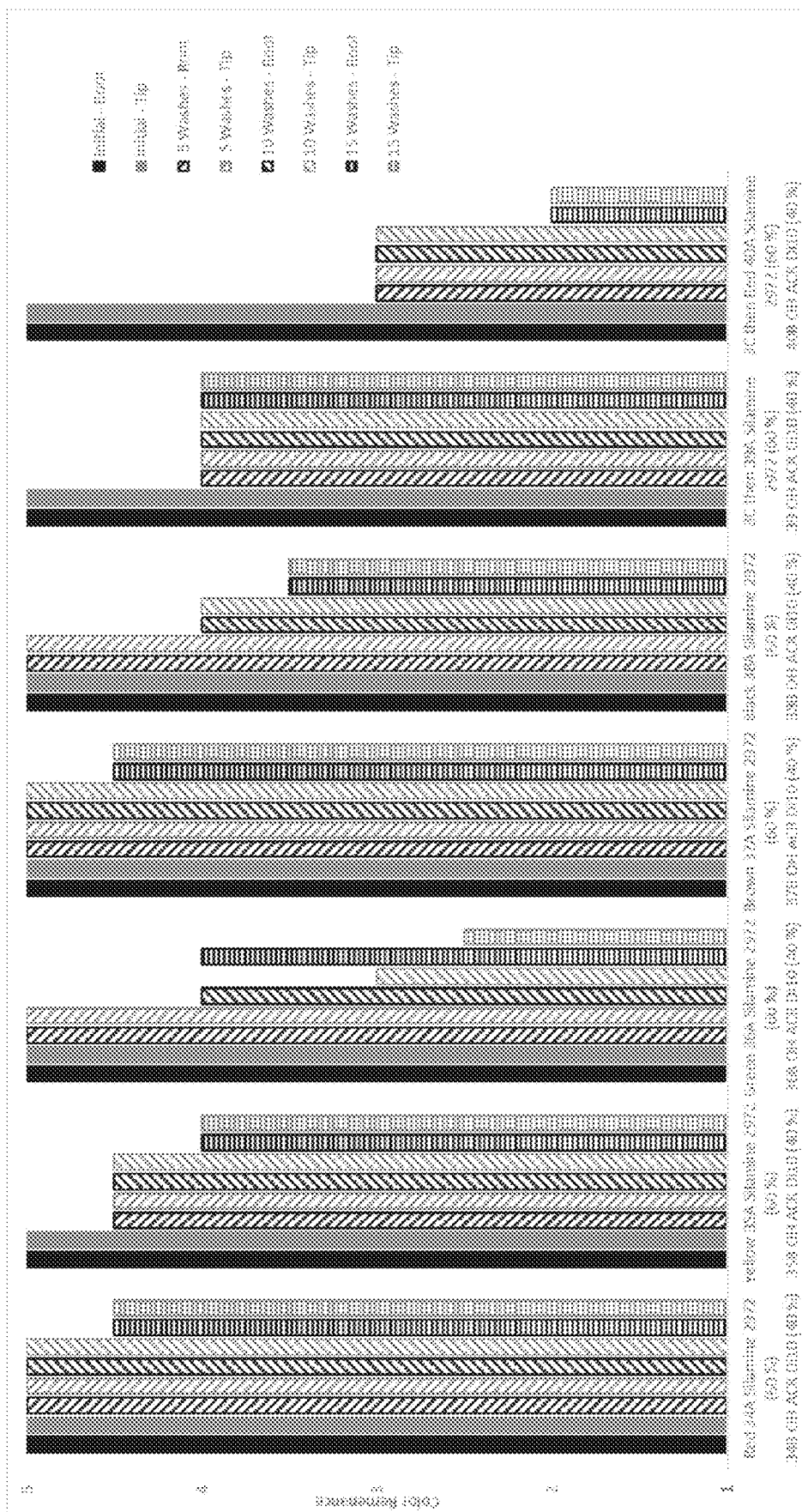
FIG. 8. Color remanence results for a series of different colored multicomponent compositions.

In the next series of experiments, different pigments, and combinations of pigment were studied using multicomponent compositions comprising a series of different pigments and mixtures of pigments with silicones with first functional groups and silicones with second functional groups. In the following six experiments a part of the A formula was mixed with a part of the B formula before application to the hair tress. The values in parenthesis are relative proportions of each silicone within the silicone mixture, with the total silicone level maintained at a constant level of 5%, except for the penultimate experiments where the level was tested at a higher level, at 15%. In the final two experiments, a different pre-treatment was used, where the pigment, in this case aluminum flakes were added into the pre-treatment 3C and applied to the hair and dried before application of the multicomponent composition, FIG. 8 shows the color remanence as assessed by the color remanence grading scale after initial application, and after 5, 10 and 15 washes on root and tip hair tresses. For all experiments apart from the last, two, 1C was used as a pretreatment.

In the first experiment, the natural white hair was colored a bright red color, and the color result was highly remanent to washing. When the yellow pigment was used, the hair was colored a chromatic yellow shade, and again the color was highly remanent. The green pigment changed the hair to an intense green color, which was remanent to washing. The brown product used, a combination of pigments to obtain an initial color on white hair which was a neutral brown. This color remained brown over extended washing, showing that each of the pigments showed similar remanence. The white hair was also turned black using pigment black, this effect was remanent to washing. In the final two experiments, the starting hair color was dark. When aluminum flakes were used alone within the pro-treatment and scaled with the multicomponent composition, the hair looked mirror like, and the effect was long lasting. In the final experiment, red colored pigments were added to the multicomponent composition, and the resulting color was a red colored metallic look, which had some remanence.

Figure 9:
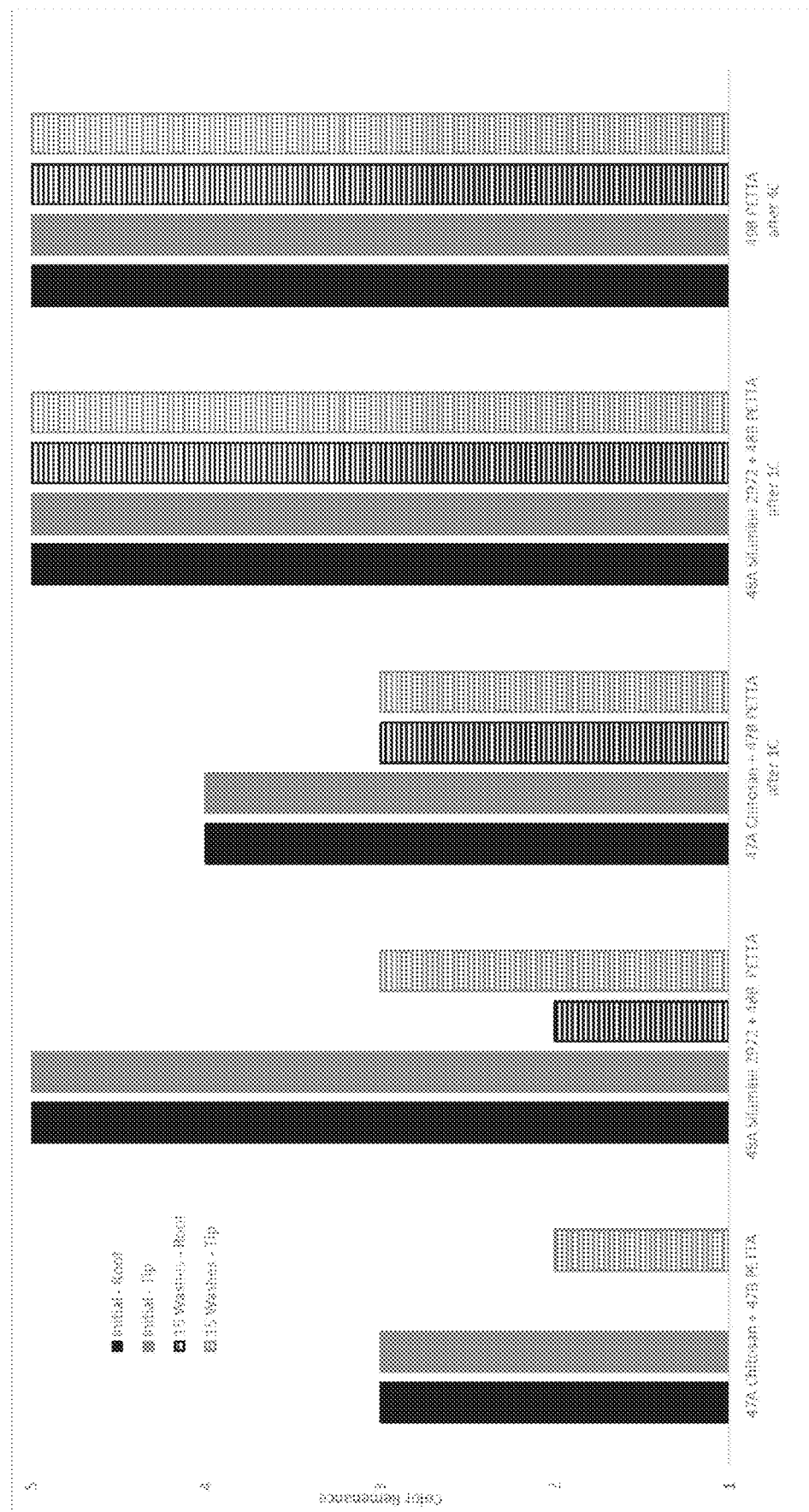
FIG. 9. Organic compound systems and mixed organic/silicone compound systems performance.

Example 9: Color Remanence of Combined Coloring Composition Comprising Organic and Mixed Organic/Silicone The following examples highlight the potential for the multicomponent system to be prepared using olefinoyloxy organic compounds. Different systems were studied using multicomponent compositions comprising a series of different first and second components. In the following experiments a part of the A formula was mixed with a part of the B formula before application to the hair tress, except for experiment 49, which will be explained later. The first two experiments had no pretreatment, the second two used 1C as a pretreatment and finally the last experiment used 4C as a pretreatment. FIG. 9 shows the color remanence as assessed by the color remanence grading scale after initial application, and after 15 washes on root and tip hair tresses.

Results show that in the organic/organic system, the performance was improved with the addition of the pre-treatment 1C. Likewise, for the mixed organic/silicone system, the remanence was further increased with the addition of the pretreatment 1C. Finally, in example 49, the PETTA was applied directly on top of the hair which had been treated with pretreatment 4C. This example shows that the steps of application of the two components of the multi-component system can be split into separate steps.

Example 10. Remanence Versus the Shore OO Hardness of the Film

Figure 10:
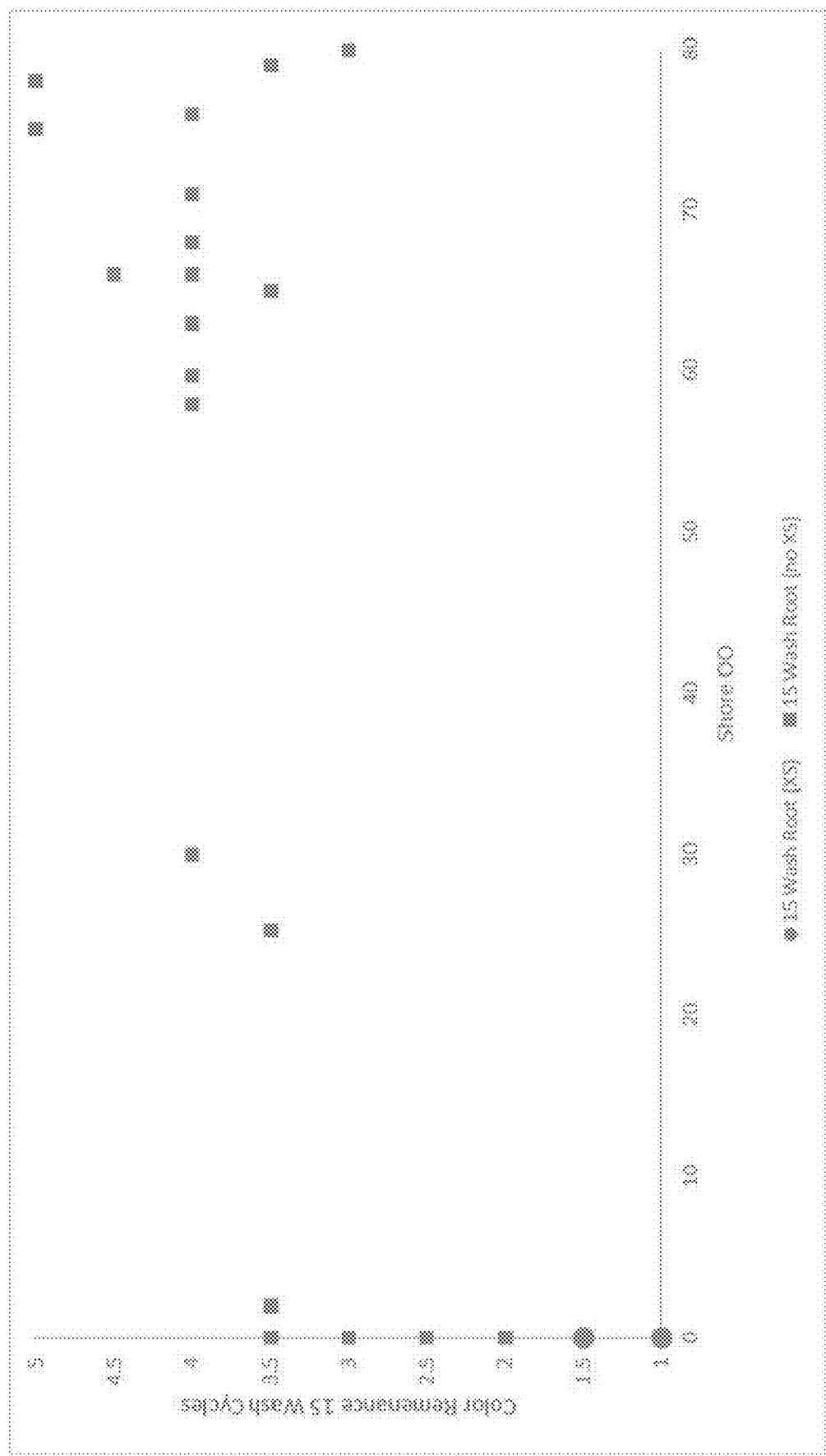
FIGS. 10 and 11. The impact of Shore OO versus the color remanence on hair after 15 wash cycles on root and tip hair.
Figure 11:
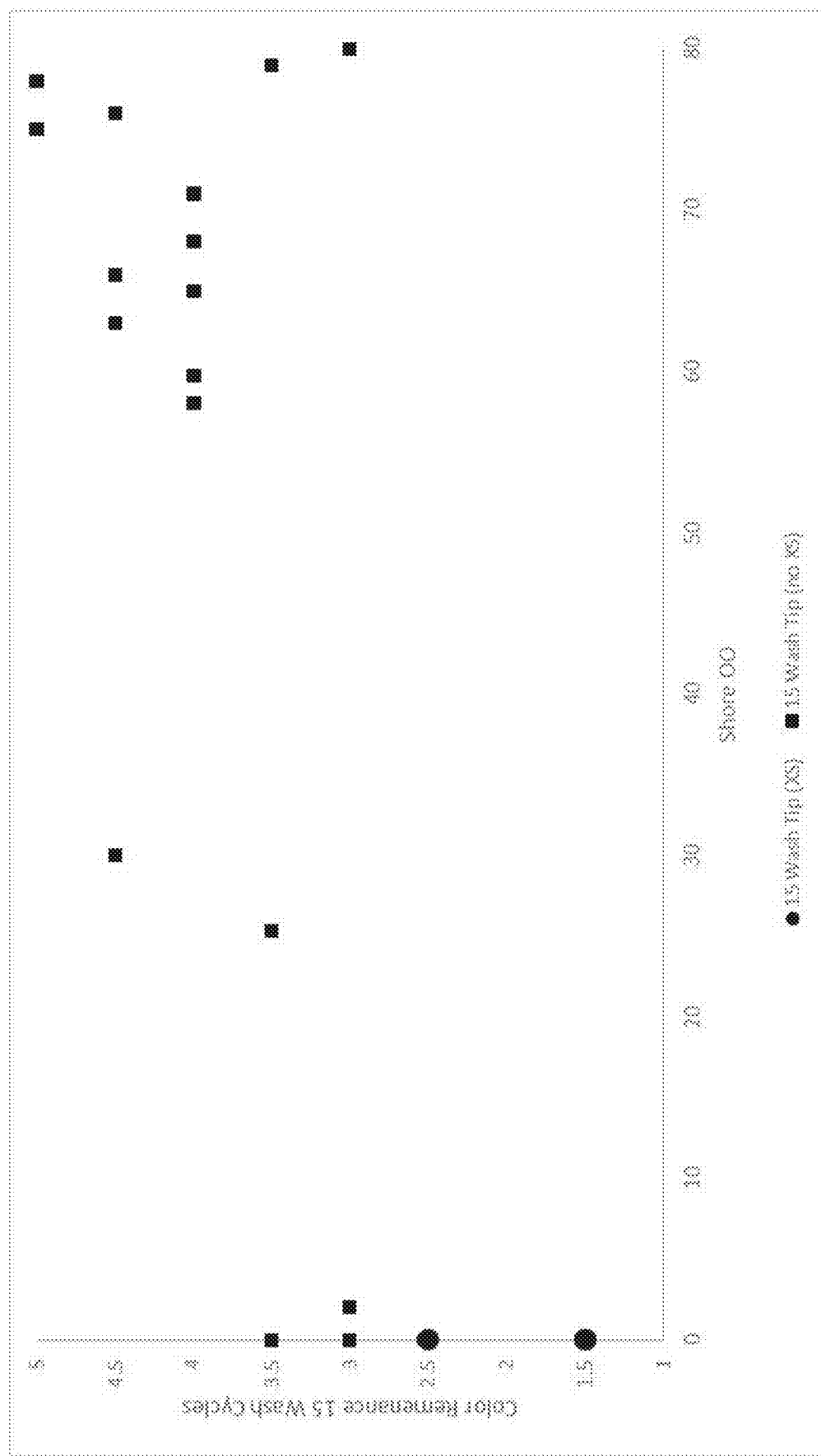

For many of the systems tested above, the Shore 00 was also measured using the method described above for the mixture of the two compounds at the same mix ratio as used in the product test. These results are plotted versus the assessed levels of color remanence after 15 wash cycles on root hair; FIG. 10, and on tip hair, FIG. 11. In all cases the hair has previously been treated with 1C as a pre-treatment composition.

The results in both cases show similar results. Generally there is a trend that materials with higher Shore 00 values deliver higher levels of remanence. For example, when the Shore OO is greater than 20, more preferable more than 55. On both graphs, the results are further subdivided into those where there was an excess of olefinoyloxy groups (labelled as XS), and those where this was not the case (labelled as no XS). Whilst not wishing to be bound to any particular theory, it believed that where there is an XS of olefinoyloxy groups, these may further react with the polymer on the hair as a result of the application of 1C as a pre-treatment. If this were to occur, the resulting cross linked system including 1C may be expected to have a higher effective Shore 00 than the one measured here.

Example 11: Color Removal Performance

Figure 12:
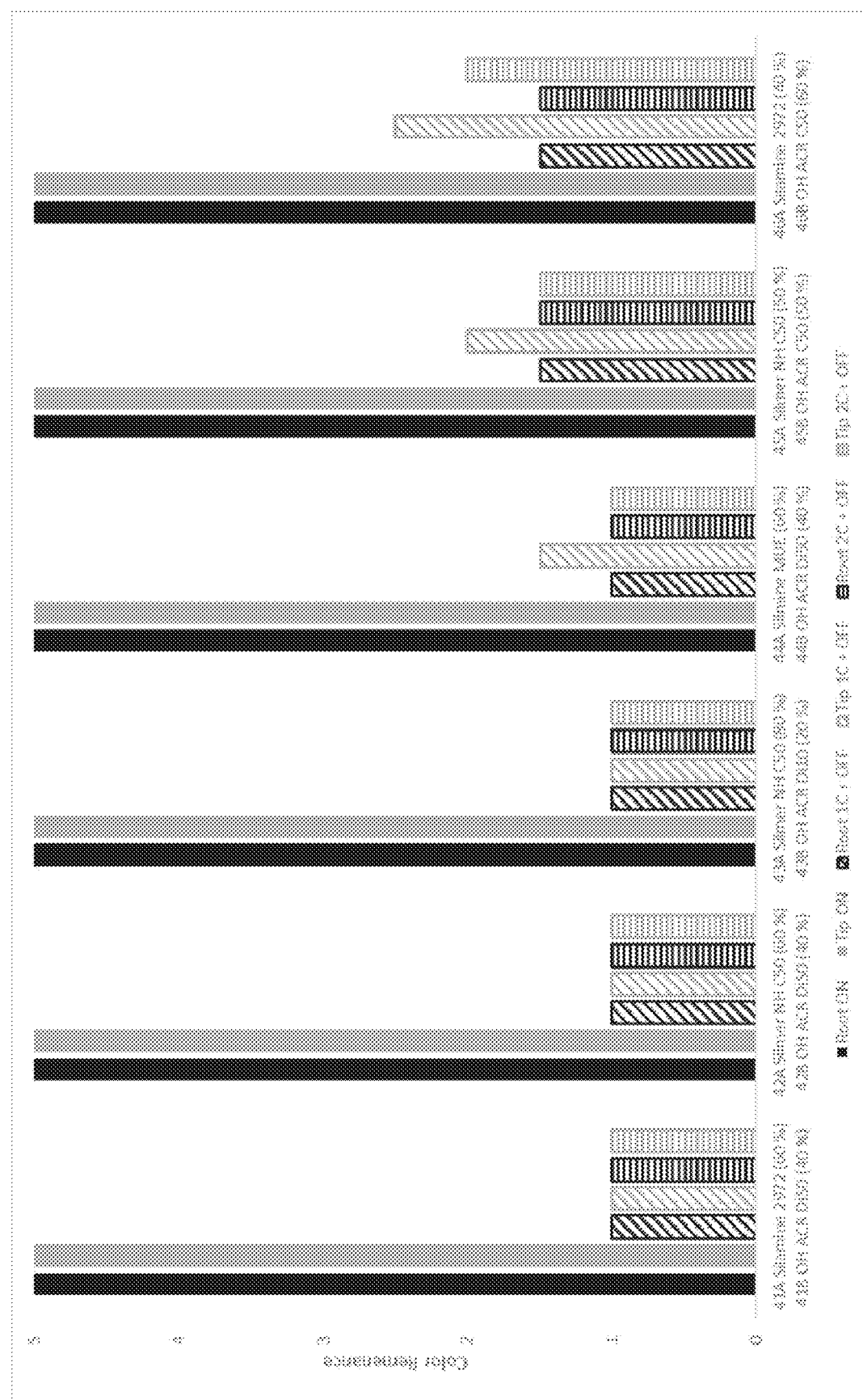
FIG. 12. Removal of the color from a series of different multicomponent compositions using the same removal formulation.

The results from a series of experiments using different ratios and different silicones with first functional groups and silicones with second functional groups are now described. FIG. 12 shows the color remanence as assessed by the color remanence grading scale after the color removal procedure, has been used on a series of different ratios of the multi-component coloring compositions, where 1C was used as a pretreatment wherein the third component contained a polyethylenimine as the base compound, and a final series were 2C was used as a pretreatment wherein the third component contained an aminosilane as a base compound. The ON performance is also shown to make the scale clear, with 5 equal to the initial color and 1 equal to no color remaining.

For all of the systems tested, all, or at least most of the color was removed when the off treatment was used.

Example 12: Impact of Removal Formulation and Method of Application

Figure 13:
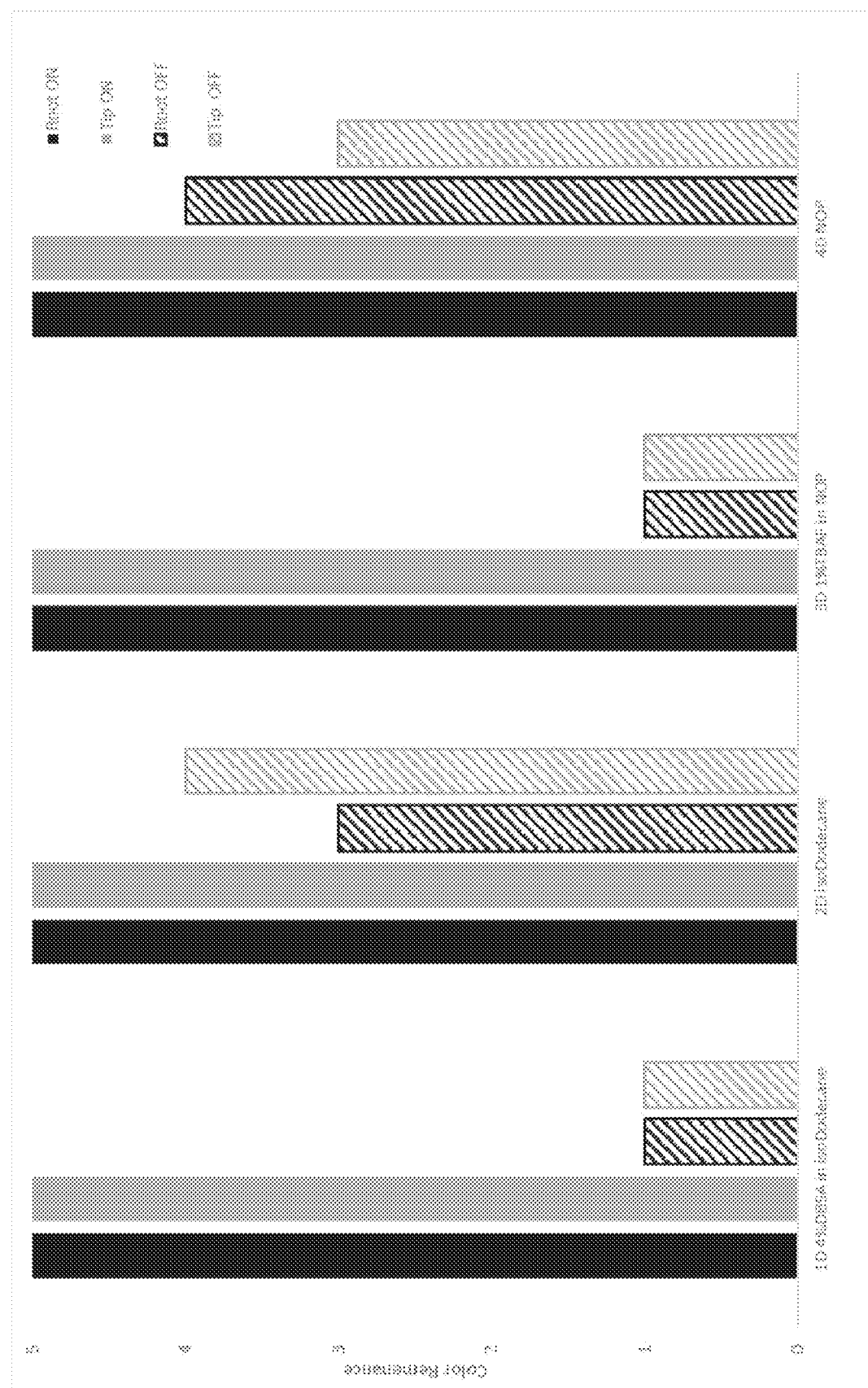
FIG. 13. Showing the impact of addition of an active to a solvent system to remove the color coating from the hair.
Figure 14:
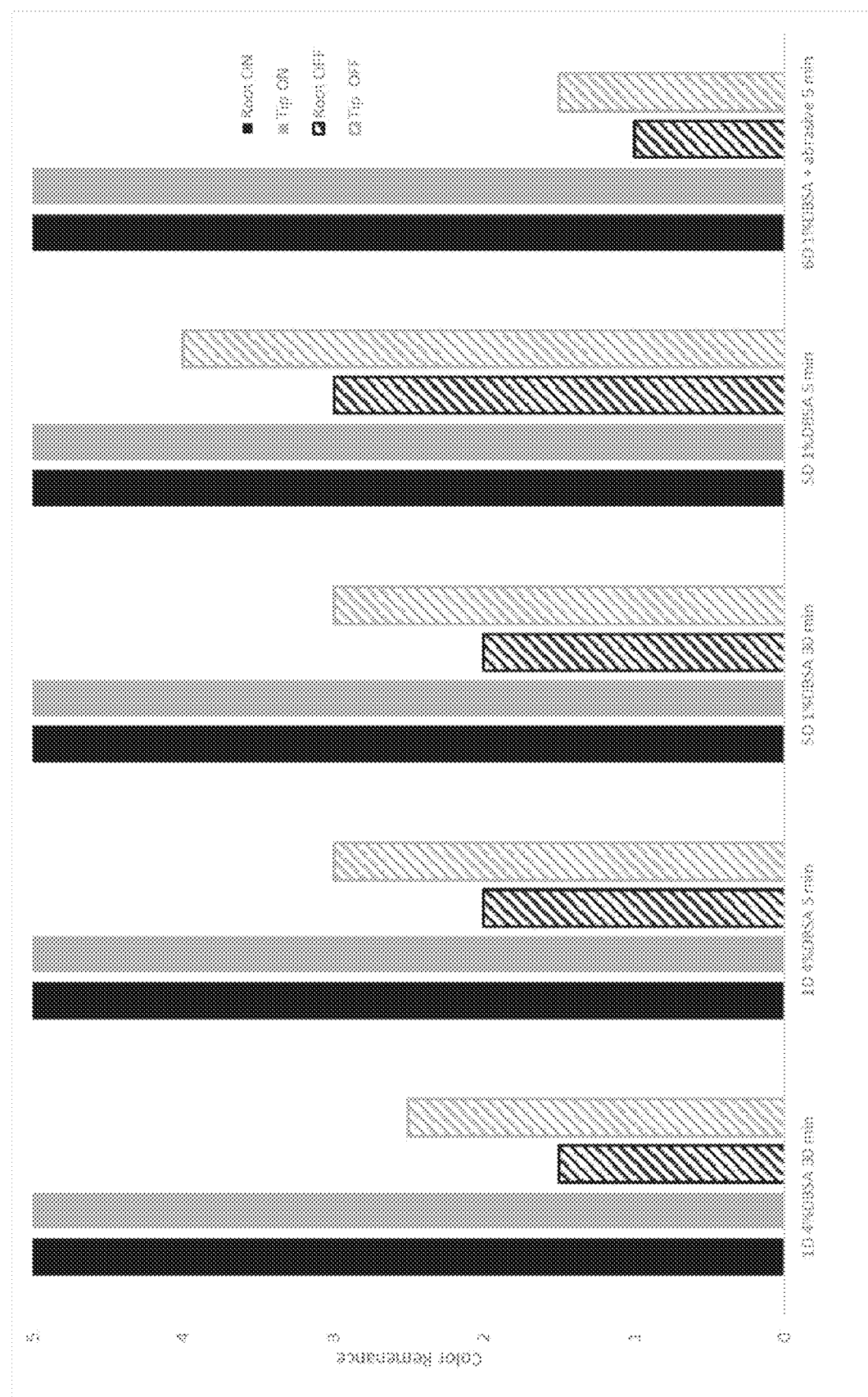
FIG. 14. The impact of concentration, processing time and rubbing on color removal.
Figure 15:
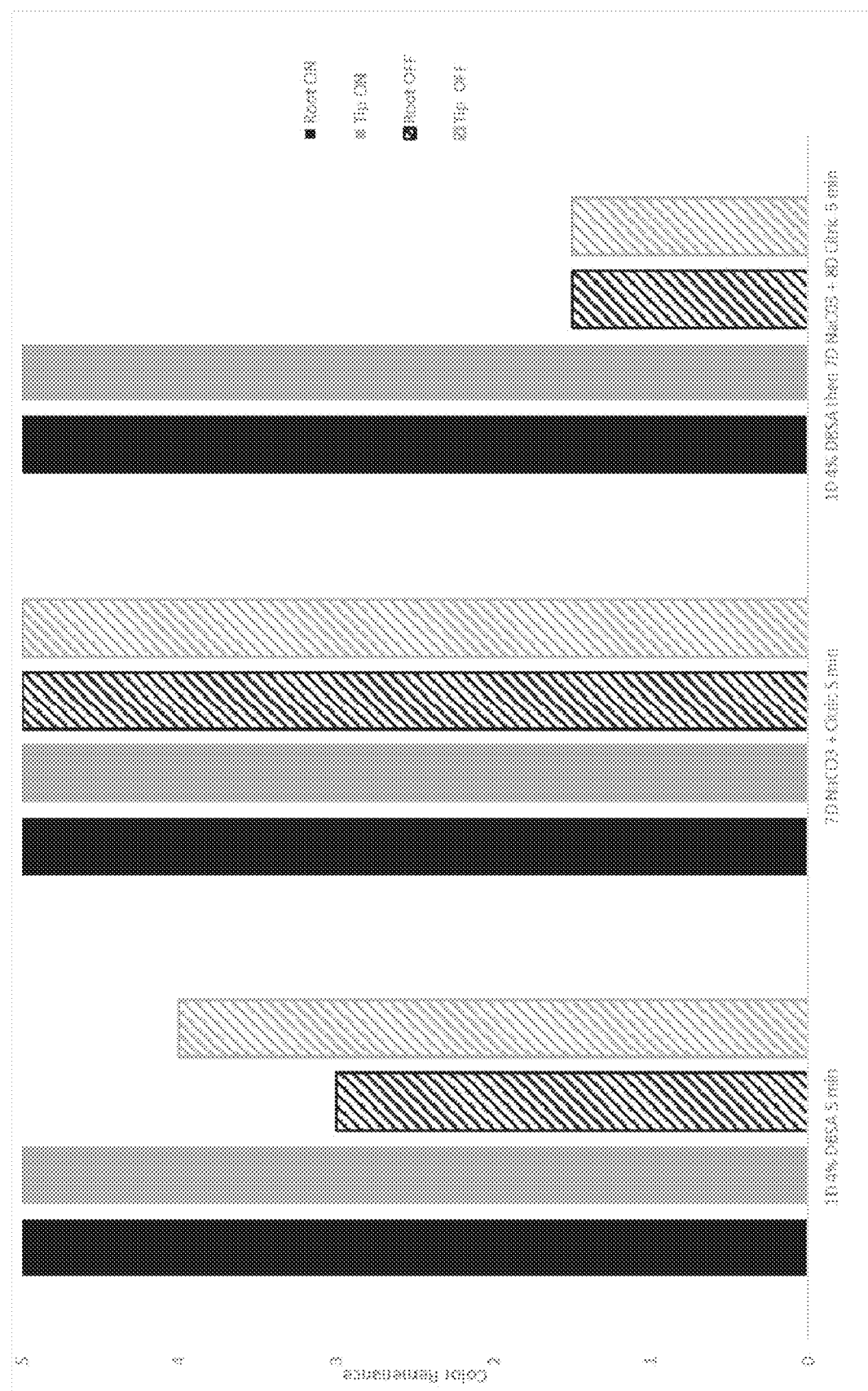
FIG. 15. Color removal through the addition of latent mechanical action provided by bubbling within the product.

In a final series of experiments, studies were performed to assess different removal formulations and method of their application to the hair. In one series a single multicomponent composition comprising one part of 50A with one part of 50B was applied to series of mot and tip hair tresses previously pre-treated with formula 1C according to the methods described above. To this colored hair various approached were then tested to remove the color from the hair, using a solvent alone or the combination of solvent and an active agent to remove the color. In all of these experiments the application time of the removal composition was 5 minutes, and the formulation was gently rubbed into the hair tress during this time period prior to rinsing the color from the hair. Results are shown in FIG. 13. A second series of removal experiments were performed to understand the impact of the length of application, and the impact of rubbing the hair tresses during the treatment process. A single multicomponent composition comprising one part of 10A with one pan of 10B was applied to a series of root and tip hair tresses previously pre-treated with formula 1C according to the methods described above. These were then tested with a series of formulations and application protocols. Removal formulation 1D was applied to the hair for either 30 or 5 minutes with no rubbing during the processing time. Alternatively, formula 5D was applied for either 30 or 5 minutes, again with no rubbing during the processing time. Finally, formulation 6D was applied for 5 minutes and the product was gently rubbed into the hair during the 5 minutes of processing time. The insights are captured within FIG. 14. In another series of experiments an alternative approach to deliver the rubbing effect was investigated. All of the products were applied without rubbing during the processing time, to hair tresses prepared pre-treated with 1C as before using 10A and 10B in a one to one mix ratio, the hair was treated with 1D for 5 minutes, or with 7D mixed with 8D an alternative system containing actives selected to degrade and cause bubbling when mixed. The last test combined both of these approach, with 1D applied for 5 minutes, and then 7D mixed one to one with 8D and applied directly on top of 1D and left, for a further 5 min. Results are shown within FIG. 15. A further alternative off approach was demonstrated within FIG. 16, where either an alkali, using commercial Wella Illumina 10/0 or oxidative treatments using Wella Welloxon Perfect 9% developer or a one to one mixture of the alkali and oxidative formulations were used as removal formulations without rubbing for 30 min on a series of multicomponent compositions applied to hair prepared after a pretreatment of 1C with the formulations described within FIG. 16.

Figure 16:
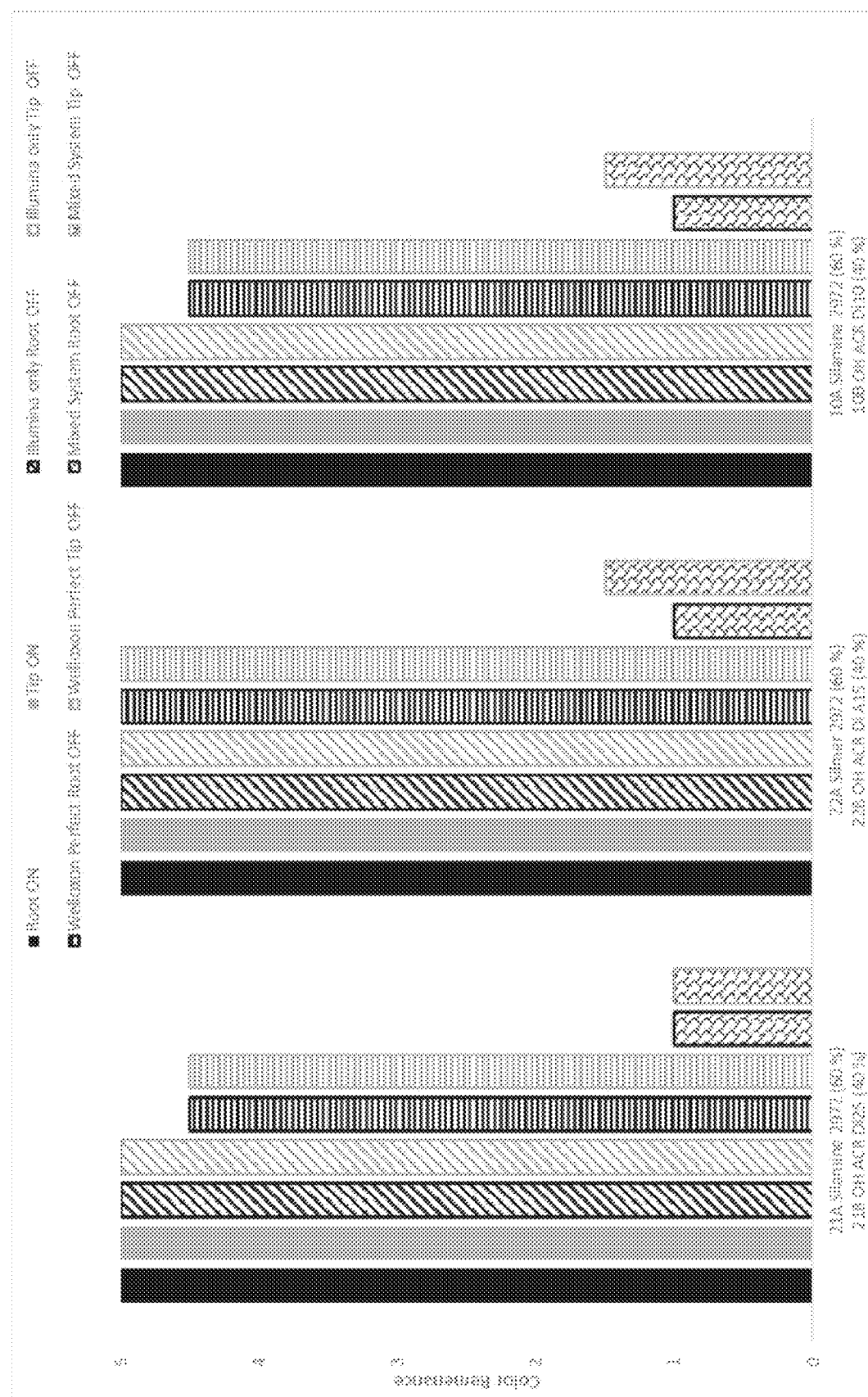
FIG. 16. Removal of color using alkali and or oxidative formulations.

FIG. 13 shows the series comparing the effect of the solvent alone compares to when the agent is added into the system. When the active is present in 1D the removal performance is much higher than when the solvent is used alone, 2D. Likewise, when the active is present, within 3D the removal is again much more than when the solvent is used alone, 4D. The impact of mechanical movement of the product into the hair and additional abrasive particles are shown in in FIG. 14. The first two sets of data show that removal formulation 1D is able to remove a substantial amount of color after 0.30 or five minutes of processing time, with, the 30 minutes working slightly better. When the active level was dropped to 0.1% in 5D versus the 4% level in 1D, there was still a reasonable level of color removal. Again, slightly more color was removed with 30 minutes of treatment. Finally, when the hair is rubbed during processing and an abrasive its added within 6D, the removal after 5 minutes is better than 1D using four times the level of active after 30 minutes of processing time. These results show that different times and level of active can be used to deliver varying degrees of color removal, and that the use of rubbing and an abrasion enhances the removal performance. Within FIG. 15 results are shown which provide an alternative means to help remove the color without the need to rub the hair during processing or add an abrasive. The formula 1D alone can remove some of the color after 5 minutes without rubbing, whereas 7D mixed with 8D cannot alone remove any of the color. When used sequentially 1D followed by direct application of a mixture of 7D and 8D a high level of color is removed. Whilst not wishing to be bound to any particular theory, its believed that the bubbling effect caused by 7D mixed with 8D helps to dislodge weakened pieces of colored film, thereby helping to remove the color from the hair. The study with alkali and oxidative treatments shown in FIG. 16 shows that the use of alkali and or oxidative formulations alone does not remove a significant level of color from the hair. However, when these are combined, the color is effectively removed from the hair. This procedure demonstrates that the combination of both the alkali composition and the presence of an oxidant can remove the colored coating.

What is claimed is:
1. A method for treating keratin material, comprising:
   pre-applying to the keratin material a polyamine in water to form a pretreated keratin material;
   and then applying to the pretreated keratin material
      a first component comprising a medium and a first compound according to Formula I; and
      a second component comprising a medium and a second compound according to Formula II;
   wherein the first and second components are applied sequentially or simultaneously to the pretreated keratin material;
   wherein

Formula I is

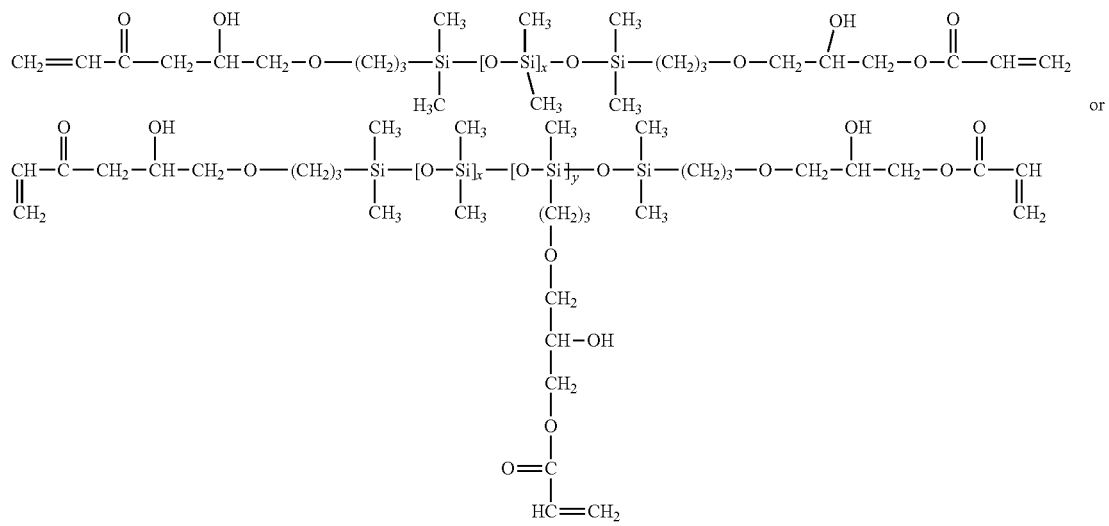

or

Me₃Si—O—(SiMe₂-O)ₓ—SiMe(—(CH₂)₃—O—CH₂—CHOH—CH₂—O—CO—CH=CH₂)—O)ᵧ—(SiMe₂-O)_z—(SiMe(—CH₂)₃—O—CH₂—CHOH—CH₂—O—CO—CH=CH₂)—O)ᵧ—(SiMe₂-O)ₓ—SiMe₃;

wherein the —(SiMe(—(CH₂)₃—O—CH₂—CHOH—CH₂—O—CO—CH=CH₂)—O)ᵧ—, (SiMe₂-O)_z and —(SiMe₂-O)ₓ groups are arranged to intersperse the —(SiMe(—(CH₂)₃—O—CH₂—CHOH—CH₂—O—CO—CH=CH₂)—O)ᵧ groups along the silicone backbone;

x is an integer of from about 5 to about 500, x' is an integer of from about 5 to about 500, z is an integer of from about 2 to 50 and y is an integer of from about 1 to about 100;

Formula II is

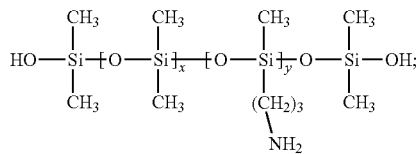

or
Me₃SiO—(SiMe₂-O)ₓ—(Si(MeAM)-O)ᵧ—(SiMe₂-O)_z—(Si(Me)(AKO)-O)ᵧ—(SiMe₂-O)ₓ—SiMe₃;
or
HO(Me₂)SiO—(SiMe₂-O)ₓ—(Si(MeAM)-O)ᵧ—(SiMe₂-O)_z—(Si(Me)(AKO)-O)ᵧ—(SiMe₂-O)ₓ—Si(Me₂)OH;
or
Me₃SiO—(SiMe₂-O)ₓ—(Si(MeAM)-O)ᵧ—SiMe₃;
or
AM-Me₂SiO—(SiMe₂-O)ₓ—(Si(MeAM)-O)ᵧ—(SiMe₂-O)ₓ—SiMe₂-AM;

wherein
AM is $R^{4a}$—NH₂;
AKO is alkyl of 3 to 20 carbons with optional oxygen in the carbon chain and optionally terminated by hydroxyl;

y is at least 2, y' is zero or 1 to 3; the sum of x and x' is about 5 to about 10,000; z is 0 or at least 1; a is zero or at least 2;

wherein $R^{4a}$ is a divalent organic group bonded to Si and NH₂ and is alkylenyl of 1 to 3 carbons or a di-alkyenyl amine group of 3 carbons in each alkyenyl group; and each of the aminosiloxane units is spaced apart on average from other aminsiloxane units by from about 5 to about 100 siloxane units; and, the polyamine is a) a linear polyethyleneimine of the formula:

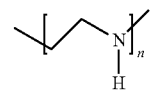

in which n is an integer representing the degree of polymerization, wherein n ranges from 50 to 20,000;

or b) a branched polyethyleneimine of the formula

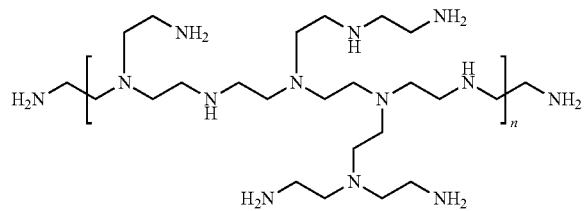

in which n is an integer representing the degree of polymerization, wherein n ranges from 5 to 4,000;

or c) a polyallylamine hydrochloride of the formula:

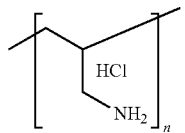

in which n is an integer representing the degree of polymerization, wherein n ranges from 50 to 20,000;
or
d) a polydiallyldimethylammonium chloride of the formula:

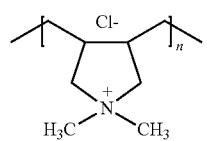

in which n is an integer representing the degree of polymerization, wherein n ranges from 10 to 20,000;
or the polyamine is an aminosilane selected from the group consisting of $Me_3Si-O-SiMe_2-O-SiMe_2NH_2$, $(CH_3O)_3Si(CH_2)_3NH_2$, $(CH_3CH_2O)_3Si(CH_2)_3NH_2$, $(CH_3O)_3Si(CH_2)_3NH(CH_2)_2NH_2$, $(CH_3CH_2O)_3Si(CH_2)_3NH(CH_2)_2NH_2$, $(CH_3CH(CH_3)CH_2O)_3Si(CH_2)_3NH(CH_2)_2NH_2$, $(CH_3)_2CHO)_3Si(CH_2)_3NH(CH_2)_2NH_2$, $(CH_3CH_2O)_3Si(CH_2)_4NH(CH_2)_2NH_2$, $(CH_3CH(CH_3)CH_2O)_3Si(CH_2)_4NH(CH_2)_2NH_2$, $((CH_3)_2CHO)_3Si(CH_2)_4NH(CH_2)_2NH_2$, and $(CH_3O)_3Si(CH_2)_4NH(CH_2)_2NH_2$.

2. The method according to claim 1 wherein Formula I is

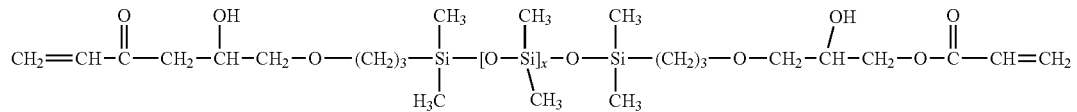

or

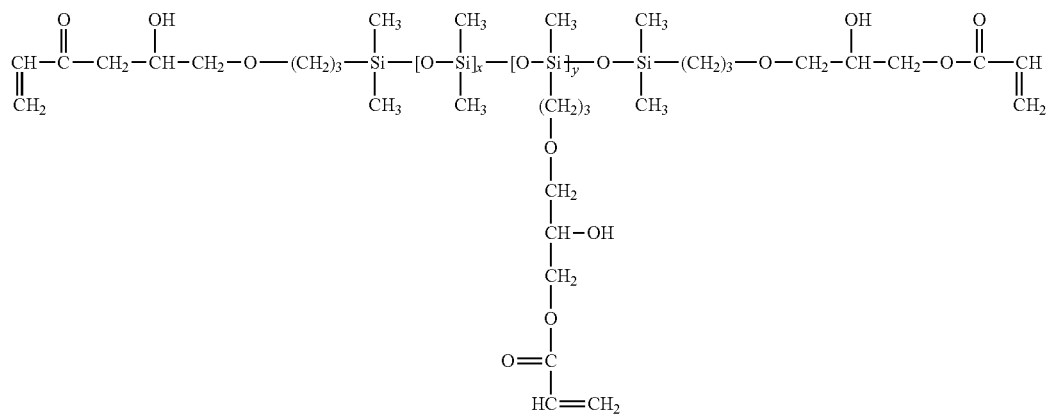

Formula II is

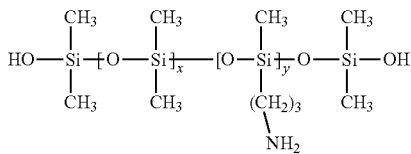

or
$Me_3SiO-(SiMe_2-O)_x-(Si(MeAM)-O)_y-(SiMe_2-O)_z-(Si(Me)(AKO)-O)_{y'}-(SiMe_2-O)_{x'}-SiMe_3$
or
$AM-Me_2SiO-(SiMe_2-O)_x-(Si(MeAM)-O)_y-(SiMe_2-O)_{x'}-SiMe_2-AM$; and
the polyamine is $(CH_3CH_2O)_3Si(CH_2)_3NH_2$ or a linear polyethyleneimine of the formula:

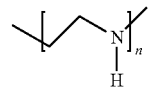

in which n is an integer representing the degree of polymerization, wherein n ranges from 50 to 20,000.

3. The method according to claim 1 wherein the medium for the first and second components is a protic or aprotic organic solvent or combinations thereof.

4. The method according to claim 1 wherein the wt percent concentration of each of the first and second compounds relative to the total weight of the combination of the first and second components and polyamine comprises a range of from 0.25 wt % to about 20 wt % and the wt percent of the combination of the first and second compounds relative to the total weight of the first and second components and polyamine comprises a range of from about 0.5 wt % to about 35 wt %.

5. The method according to claim 1 wherein the keratin material is human scalp hair and the treatment is hair styling or hair care.

6. The method according to claim 1 wherein the first and/or second component further comprises pigment microparticles and the keratin material is human scalp hair.

7. The method according to claim 6 wherein the pigment microparticles are combined with one or more dispersants.

8. A coating on human scalp hair produced according to the method of claim 5.

9. A colored coating on human scalp hair produced according to the method of claim 6.

10. The method of claim 1 wherein the polyamine is a linear or branched polyethylene imine.

\* \* \* \* \*